United States Patent
Wang et al.

(10) Patent No.: US 11,655,260 B2
(45) Date of Patent: May 23, 2023

(54) HETEROCYCLIC COMPOUNDS AS ARGINASE INHIBITORS

(71) Applicant: Guangdong Newopp Biopharmaceuticals Co., Ltd., Guangzhou (CN)

(72) Inventors: Zhaoyin Wang, Guangzhou (CN); Nanxin Li, Guangzhou (CN); Jianbin Ma, Guangzhou (CN); Yanqiang Shao, Guangzhou (CN)

(73) Assignee: GUANGDONG NEWOPP BIOPHARMACEUTICALS CO., LTD., Guangzhou (CN)

( * ) Notice: Subject to any disclaimer, the term of this patent is extended or adjusted under 35 U.S.C. 154(b) by 199 days.

(21) Appl. No.: 16/956,693

(22) PCT Filed: Dec. 21, 2018

(86) PCT No.: PCT/CN2018/122815
§ 371 (c)(1),
(2) Date: Jun. 22, 2020

(87) PCT Pub. No.: WO2019/120296
PCT Pub. Date: Jun. 27, 2019

(65) Prior Publication Data
US 2020/0325161 A1    Oct. 15, 2020

Related U.S. Application Data

(60) Provisional application No. 62/708,773, filed on Dec. 22, 2017.

(51) Int. Cl.
*C07F 5/02* (2006.01)
*A61K 45/06* (2006.01)

(52) U.S. Cl.
CPC .............. *C07F 5/025* (2013.01); *A61K 45/06* (2013.01)

(58) Field of Classification Search
CPC ......... C07F 5/025; A61K 45/06; A61K 31/69; A61P 13/12; A61P 27/02; A61P 31/00; A61P 35/00; A61P 37/02
USPC ............................................. 514/64; 544/229
See application file for complete search history.

(56) References Cited

FOREIGN PATENT DOCUMENTS

| WO | 2012058065 A1 | 5/2012 |
| WO | 2013158262 A1 | 10/2013 |
| WO | 2016210106 A1 | 12/2016 |
| WO | 2017075363 A1 | 5/2017 |

OTHER PUBLICATIONS

Int'l. Search Report for PCT/CN2018/122815, dated Mar. 15, 2019.

*Primary Examiner* — Taylor V Oh
(74) *Attorney, Agent, or Firm* — MaxGoLaw PLLC

(57) ABSTRACT

Heterocyclic compounds are provided as arginase inhibitors, in particular to a compound represented by Formula (I), or a pharmaceutically acceptable salt, stereoisomer or tautomer, or prodrug thereof and a pharmaceutical composition including the compound.

6 Claims, No Drawings

HETEROCYCLIC COMPOUNDS AS ARGINASE INHIBITORS

BACKGROUND

Cancer immunotherapy is a therapeutic area focused on activating the body's own immune system to attack and kill tumors. The naturally occurring amino acid arginine is implicated in tumor immunology, as it is important for the activation, growth, and survival of cancer-fighting cytotoxic T-cells. However, levels of arginine are depleted in the tumor microenvironment by arginase, an enzyme produced and secreted by myeloid derived suppressor cells (MDSCs). In fact, elevated levels of arginase enzyme have been observed in the plasma of renal cell carcinoma, breast cancer, chronic myelogenous leukemia, esophageal cancer, prostate cancer, non-small cell lung cancer, glioblastoma, and acute myeloid leukemia patients. Therefore, there is a need to develop inhibitors of arginase that restore arginine levels in the tumor microenvironment, therefore promoting the tumor-killing activity of cytotoxic T-cells.

SUMMARY OF INVENTION

The present invention describes a novel series of inhibitors of arginase with novel cyclic structures. The present invention further describes pharmaceutical formulations that include an inhibitor of arginase.

In one aspect, the invention features a compound of Formula (I),

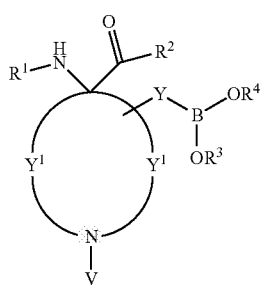

Formula (I)

or a pharmaceutically acceptable salt, stereoisomer, tautomer, or prodrug thereof.
wherein
$R^1$ is selected from H, straight or branched $(C_{1-6})$alkyl, $(C_{3-6})$cycloalkyl, $(C_{3-10})$ cycloalkyl-$(C_{1-6})$alkylene-, $(C_{5-10})$aryl-$(C_{1-12})$alkylene-, $(C_{1-10})$heteroaryl-$(C_{1-12})$alkylene-, $(C_{3-10})$heterocycloalkyl-$(C_{1-12})$alkylene- and $(C_{1-6})$alkyl-C(O)—;
$R^2$ is selected from $OR^a$, and $NR^bR^c$;
$R^a$, $R^b$, $R^c$ is selected from hydrogen, straight or branched $(C_{1-12})$ alkyl, $(C_{3-12})$ cycloalkyl, $(C_{3-10})$cycloalkyl-$(C_{1-12})$alkylene-, $(C_{5-10})$aryl-$(C_{1-12})$alkylene-, $(C_{1-10})$heteroaryl-$(C_{1-12})$alkylene-, $(C_{3-10})$heterocycloalkyl-$(C_{1-12})$alkylene-, $R^a$, $R^b$, $R^c$ is optionally substituted with $R^5$;
$R^3$ and $R^4$ are independently selected from hydrogen, straight or branched $(C_{1-6})$alkyl, $(C_{3-8})$cycloalkyl, $(C_{3-8})$ cycloalkyl$(C_{1-6})$alkylene, substituted $(C_{3-8})$cycloalkyl$(C_{1-6})$ alkylene, $(C_{5-12})$aryl; $R^3$ and $R^4$ can be connected with one or two bonds, when it is connected by two bonds, it form another ring other than the ring containing B and O;
Y, $Y^1$ and $Y^2$ is independently selected from substituted or unsubstituted alkylene, alkenylene, alkynylene, arylene, and cycloalkylene, wherein one or more —$CH_2$— groups in Y are optionally and independently replaced with a moiety Q that is selected from O, $NR^i$, S, S(O), S(O)$_2$, and $CR^5R^6$; or wherein any two adjacent —$CH_2$— groups optionally are replaced by a cycloalkylene group, provided that Y does not contain two adjacent Q moieties selected from O, $NR^i$, S, S(O), and S(O)$_2$;
$R^5$ and $R^6$ are independently chosen from halogen, $C_{1-12}$ alkyl, $C_{2-12}$ alkenyl, $C_{2-12}$ alkynyl, $C_{3-12}$ cycloalkyl, $C_{6-12}$ aryl, $C_{3-12}$ heterocyclyl, $C_{1-12}$ heteroaryl, —S(O)$_m$R$^7$, —S(O)$_2$NR$^j$R$^k$, —S(O)$_2$OR$^7$, —NO$_2$, —NR$^j$R$^k$, —(CR$^8$R$^9$)OR$^7$, —CN, —C(O)R$^7$, —OC(O)R$^7$, —O(CR$^8$R$^9$)$_n$R$^7$, —NR$^7$C(O)R$^{10}$, —(CR$^8$R$^9$)$_n$C(O)OR$^7$, —(CR$^8$R$^9$)$_n$C(O) NR$^j$R$^k$, —(CR$^8$R$^9$)$_n$NR$^j$R$^k$, —C(=NR$^j$)NR$^j$R$^k$, —NR$^7$C(O) NR$^j$R$^k$, —NR$^7$S(O)$_2$R$^1$ or SF$_5$, $R^i$, $R^j$ and $R^k$ are defined as the same as for $R^b$ and $R^c$ and each hydrogen in $R^5$ and $R^6$ may be unsubstituted or substituted by $R^{10}$, and wherein $R^5$ and $R^6$ on adjacent atoms are uncombined or combine to form a $C_{6-12}$ aryl, 5-12 membered heteroaryl, $C_{3-12}$ cycloalkyl or 3-12 membered heterocyclyl;
m is 0, 1 or 2;
n selected from 0 to 10;
$R^7$, $R^8$ and $R^9$ are independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heterocyclyl, 5-12 membered heteroaryl; $R^8$ and $R^9$ together with the carbon atom to which they are bound form a 3-, 4-, 5- or 6-membered ring that is fully saturated, or partially saturated and that optionally contains 1-3 additional heteroatom ring members selected from O, S, and $NR^j$, wherein the ring is optionally fused with a cycloalkyl, heterocyclic or aromatic ring; $R^7$, $R^8$ and $R^9$ are optionally substituted with $R^{10}$;
$R^{10}$ may be chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heterocyclic ring, 5-12 membered heteroaryl ring, —NH$_2$, —CN, —OH, —O—$C_{1-12}$alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heterocyclyl) or —O—(CH$_2$)$_n$(5-12 membered heteroaryl); and each hydrogen in $R^1$ may be unsubstituted or substituted by $R^{11}$;
$R^{11}$ may be chosen from halogen, $C_{1-12}$ alkyl, $C_{1-12}$ alkoxy, $C_{3-12}$ cycloalkyl, $C_{6-12}$ aryl, 3-12 membered heterocyclyl, 5-12 membered heteroaryl, —O—$C_{1-12}$ alkyl, —O—(CH$_2$)$_n$C$_{3-12}$ cycloalkyl, —O—(CH$_2$)$_n$C$_{6-12}$ aryl, —O—(CH$_2$)$_n$(3-12 membered heterocyclyl), —O—(CH$_2$)$_n$(5-12 membered heteroaryl) or —CN, and each hydrogen in $R^{11}$ may be unsubstituted or substituted by halogen, —OH, —CN, —$C_{1-12}$ alkyl which may be unsubstituted, or partially halogenated or fully halogenated, —O—$C_{1-12}$ alkyl which may be unsubstituted or partially halogenated or fully halogenated, or substituted with —C(O) R$^a$;
V is selected from —S(O)$_2$NR$^j$R$^k$, —S(O)$_2$OR$^7$ or

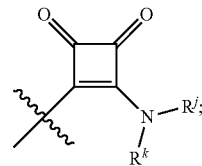

$R^7$, $R^i$, $R^j$ and $R^k$ are defined as the same as for $R^b$ and $R^c$ and each hydrogen in $R^7$ may be unsubstituted or substituted by $R^{10}$;

In one embodiment, the invention features a compound of Formula (II), or a pharmaceutically acceptable salt thereof:

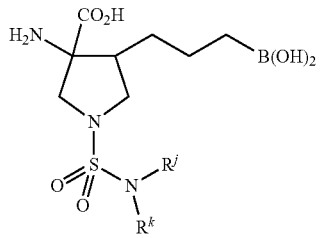
(II)

$R^j$ and $R^k$ are defined as above;

In another embodiment, the invention features a compound of Formula (III), or a pharmaceutically acceptable salt thereof:

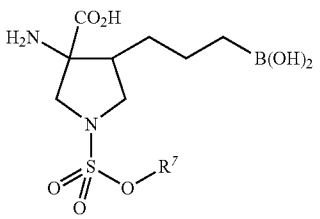
(III)

$R^7$ is defined as above;

In yet another embodiment, the invention features a compound of Formula (IV), or a pharmaceutically acceptable salt thereof:

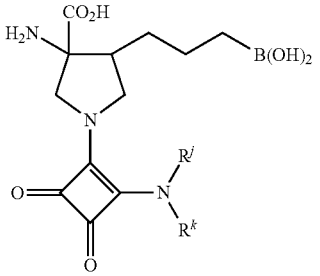
(IV)

$R^j$ and $R^k$ are defined as above.

In yet another aspect of the present invention, the invention features a prodrug of compounds in Formula (I) represented by Formula (V) to (XII):

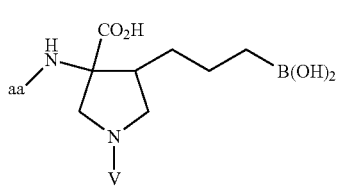
Formula (V)

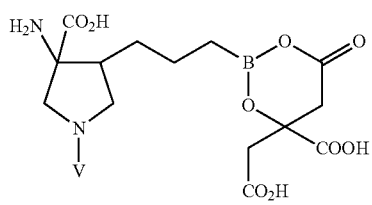
Formula (VI)

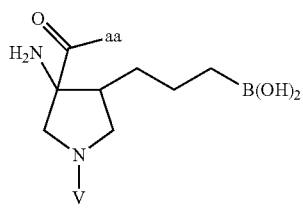
Formula (VII)

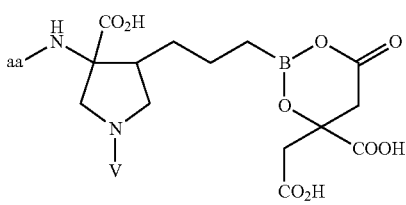
Formula (VIII)

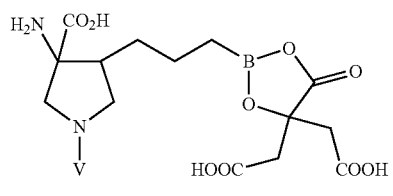
Formula (IX)

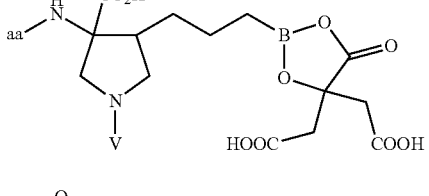
Formula (X)

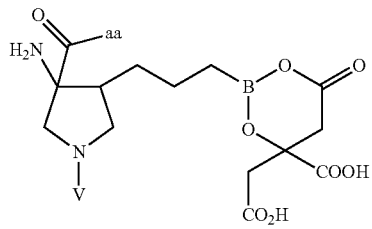
Formula (XI)

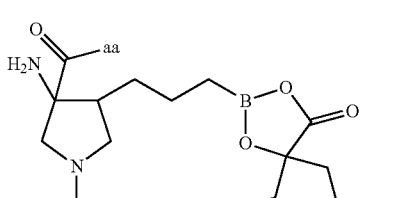
Formula (XII)

aa is a natural or unnatural amino acid such as, but not limited to, Ala, Val or Phe; aa may also be a dipeptide comprised of any two natural or unnatural amino acids. V is defined as above.

In certain embodiments, the invention provides a compound of the following structure:
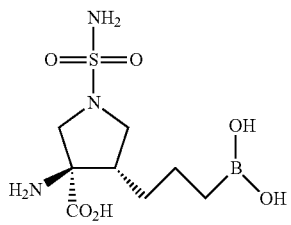
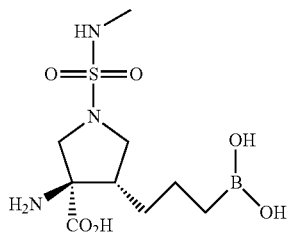
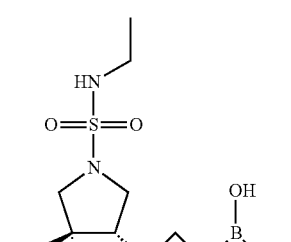
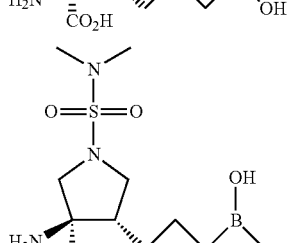
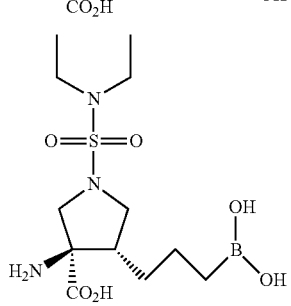
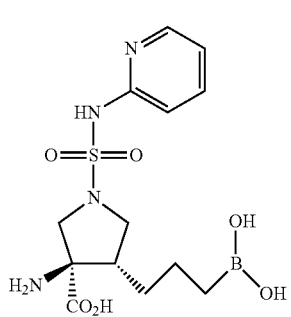
-continued
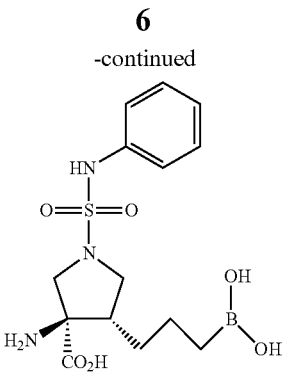
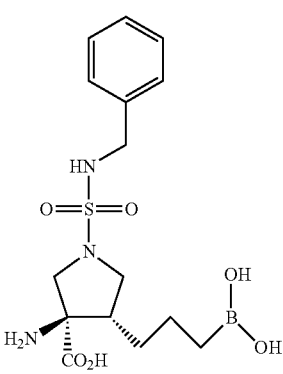
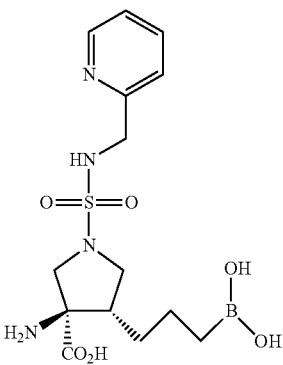
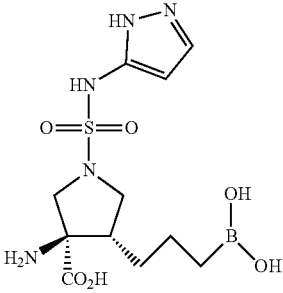
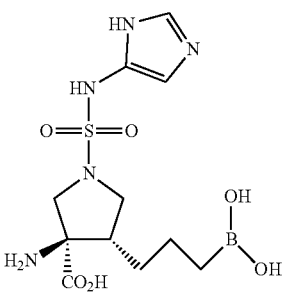

-continued
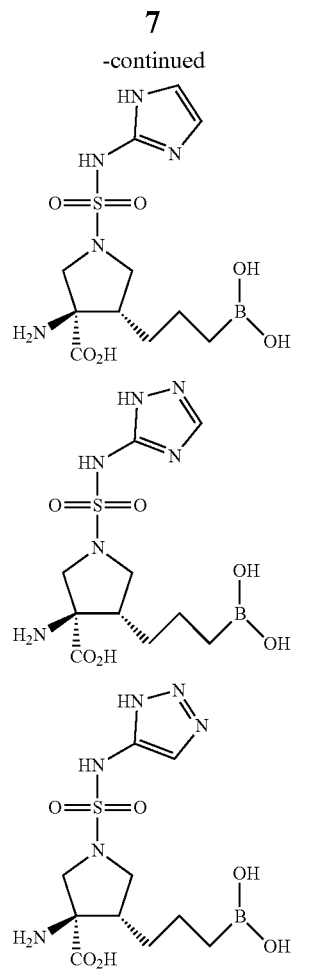
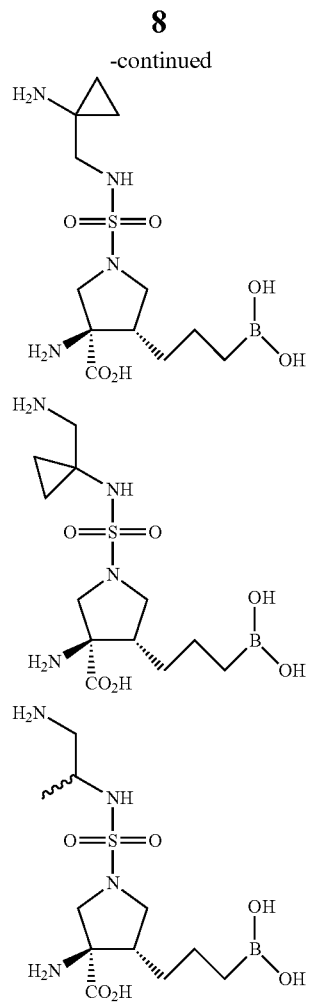
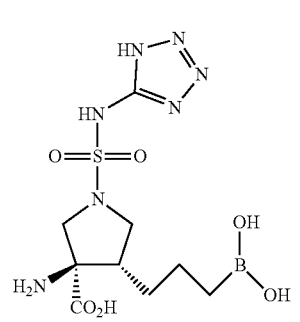
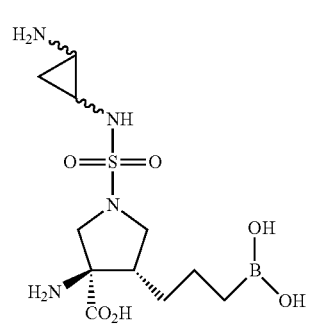
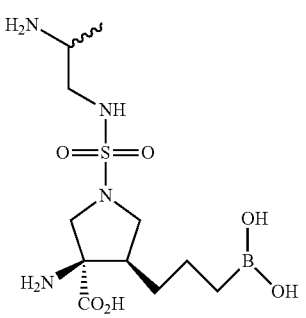
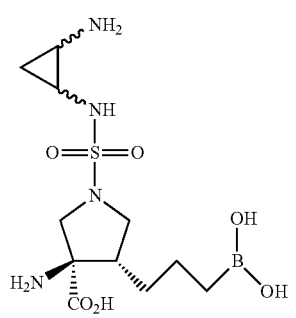

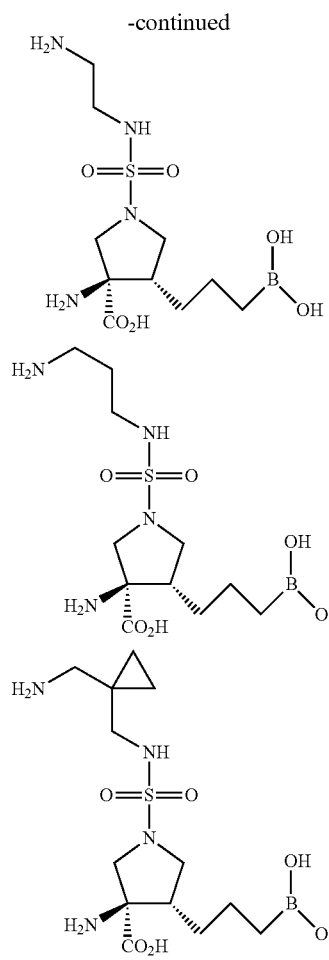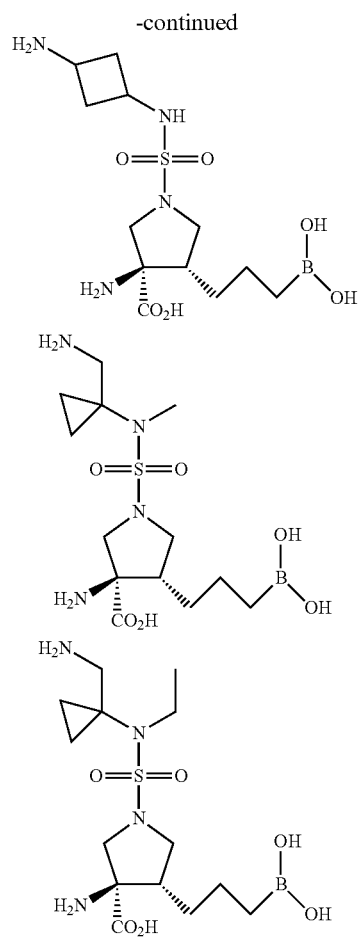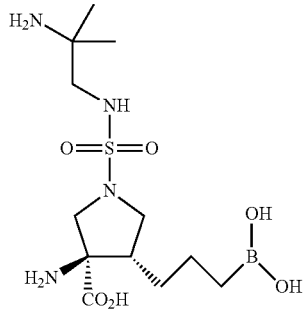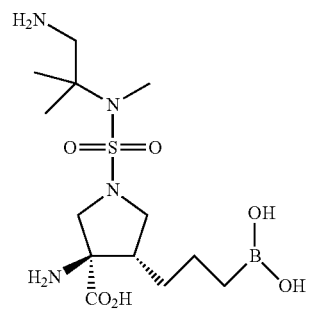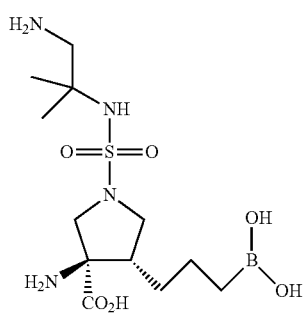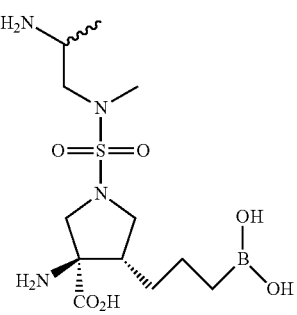

-continued
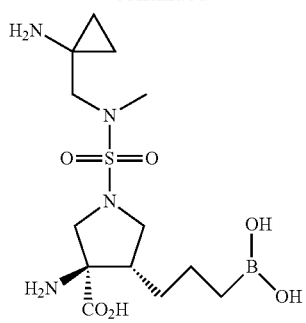
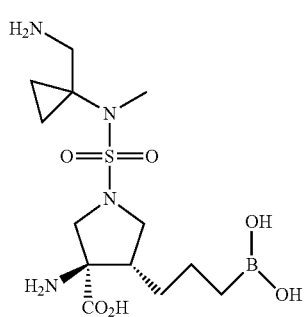
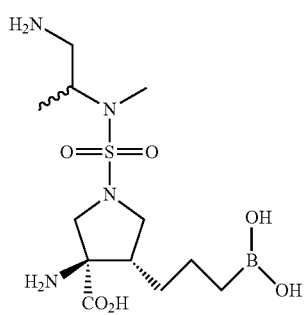
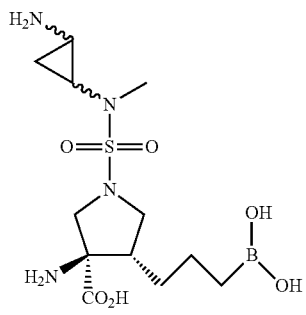
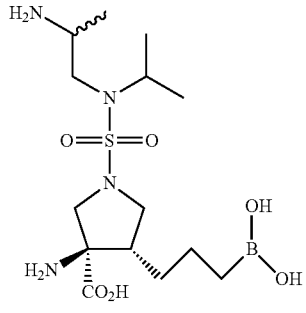
-continued
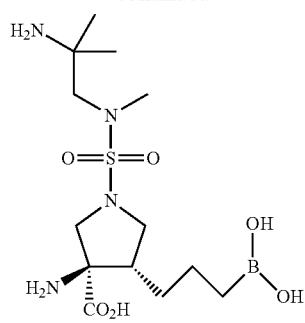
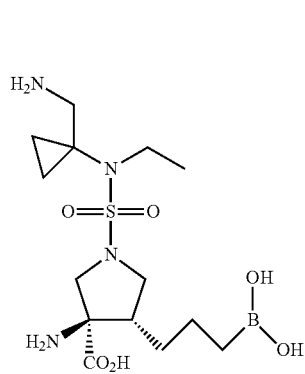
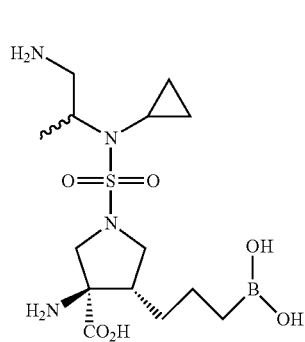
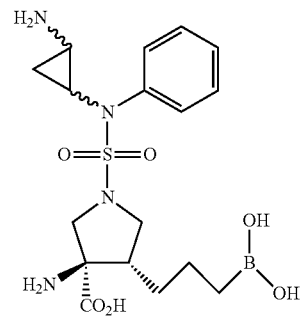
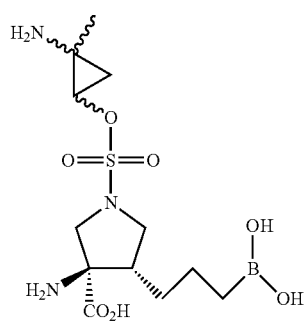

13
-continued
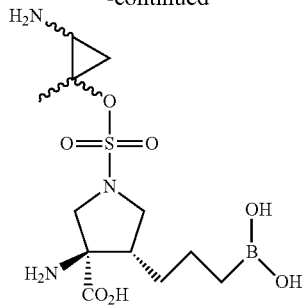
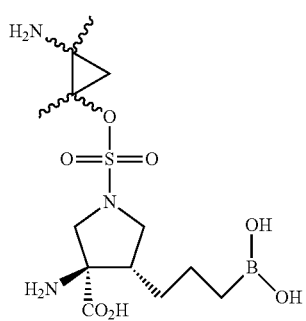
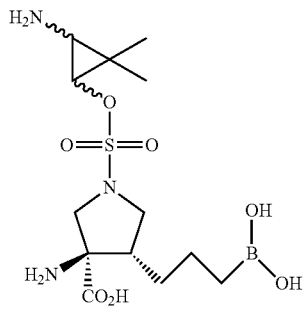
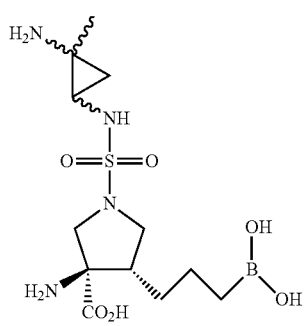
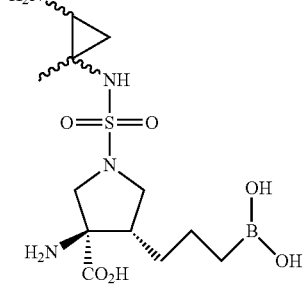
14
-continued
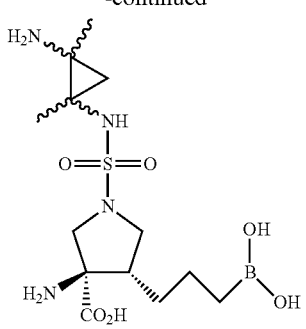
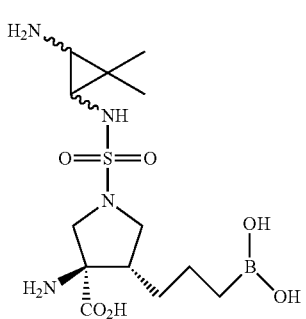
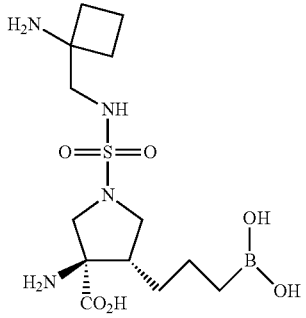
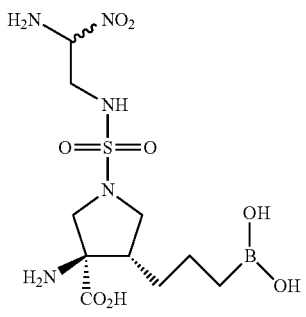
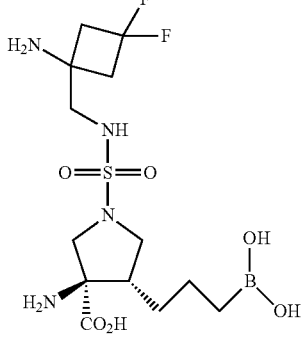

-continued
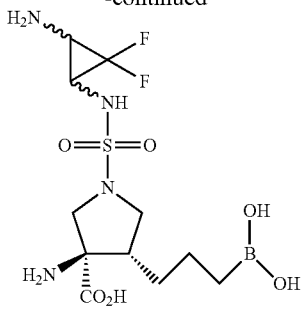
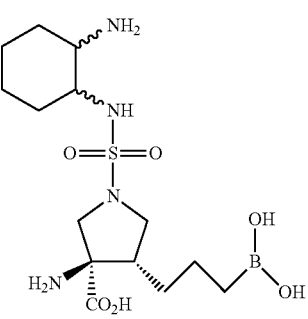
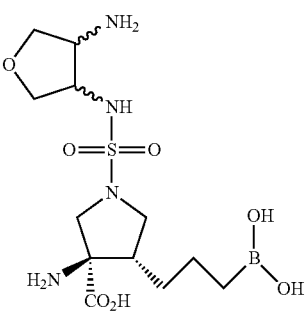
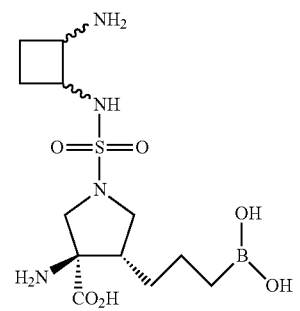
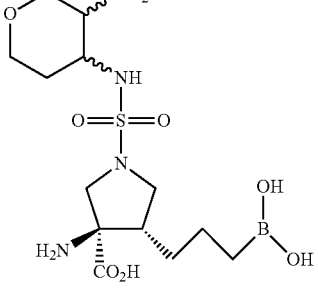
-continued
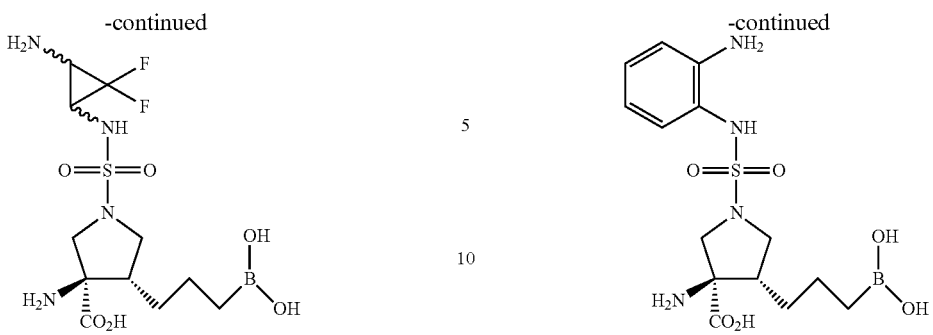
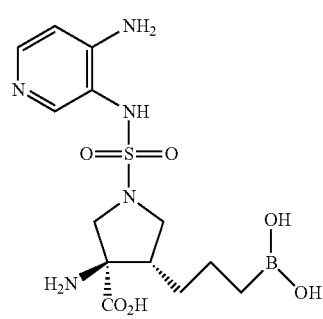
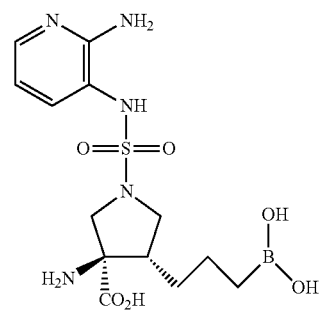
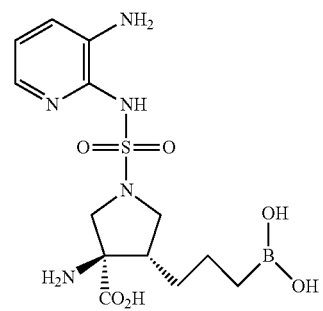
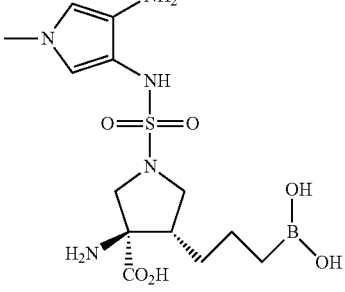

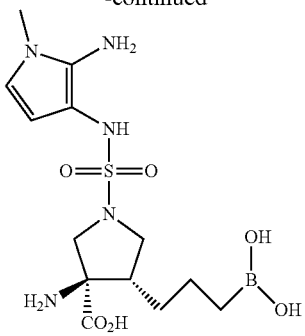
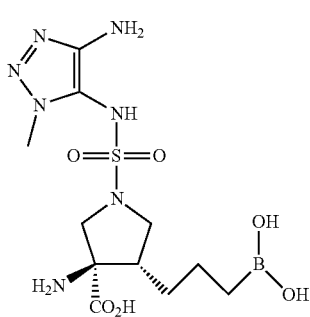
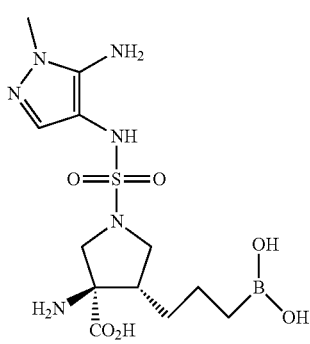
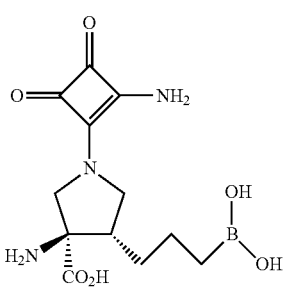
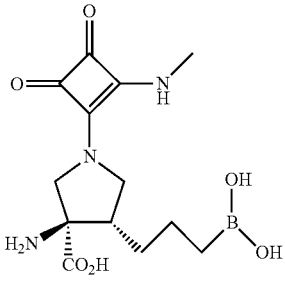
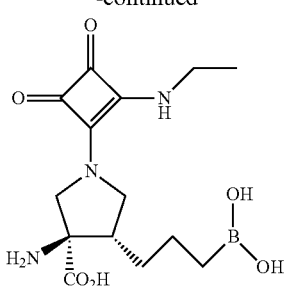
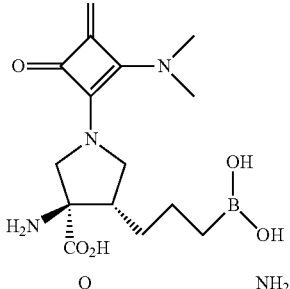
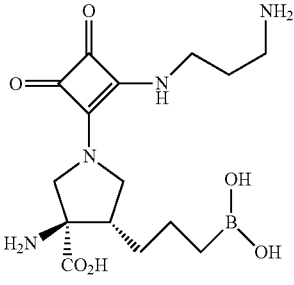
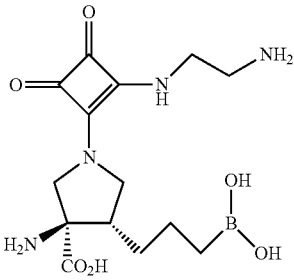
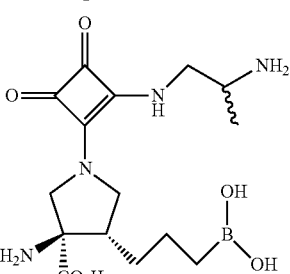
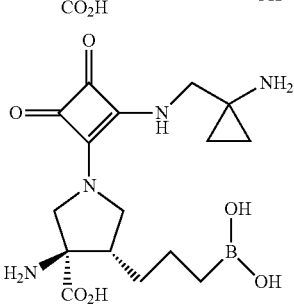

-continued
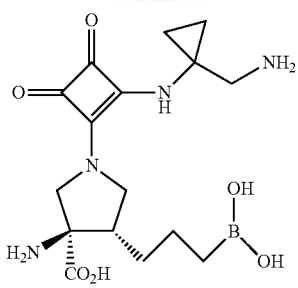
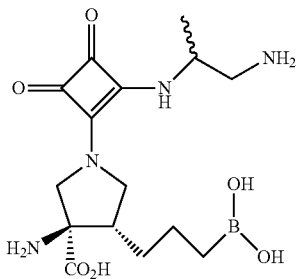
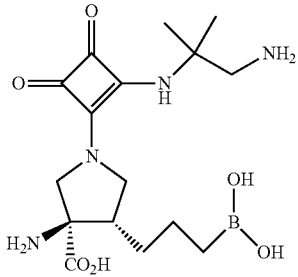
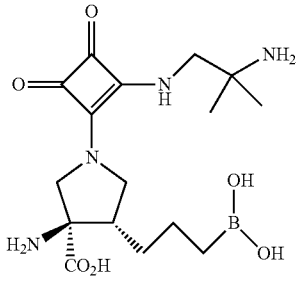
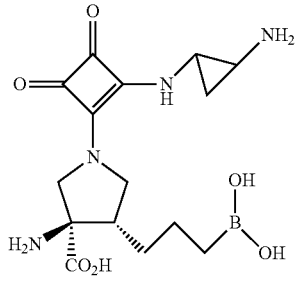
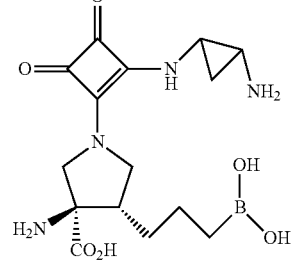
-continued
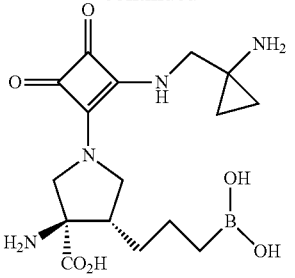
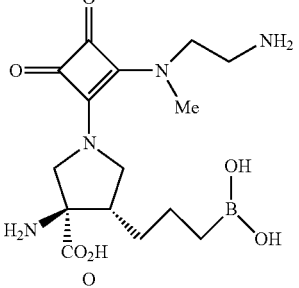
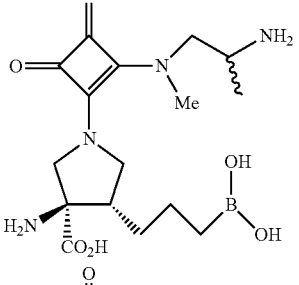
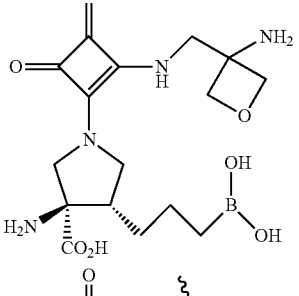
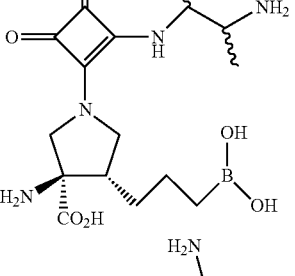
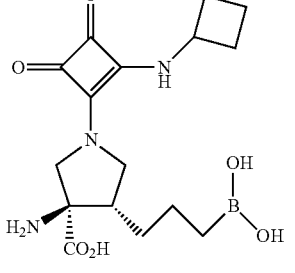

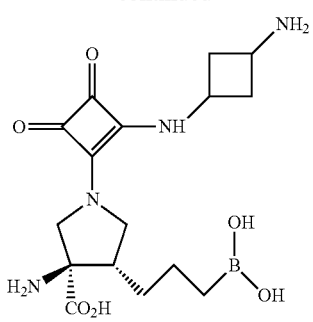
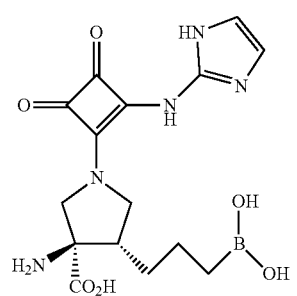
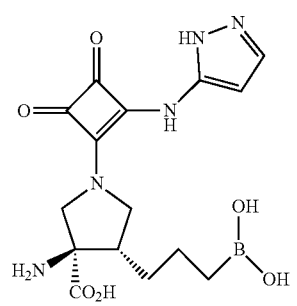
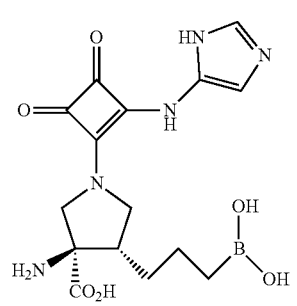
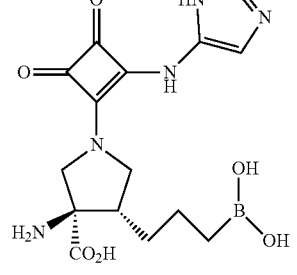
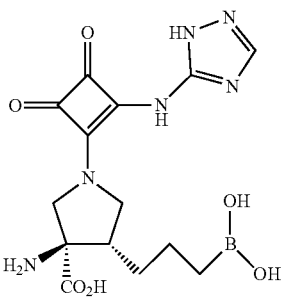
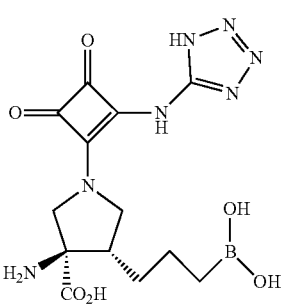
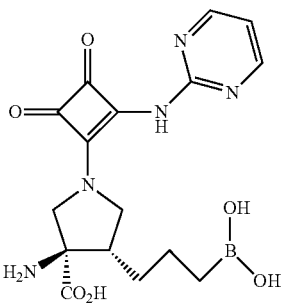
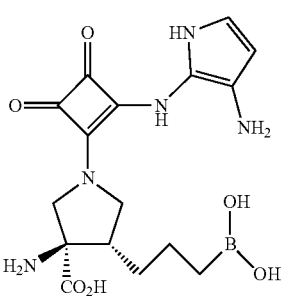
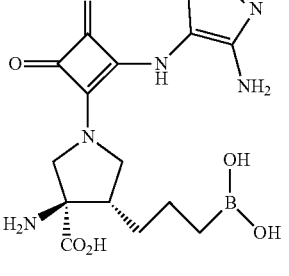

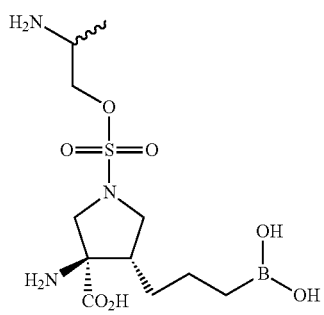
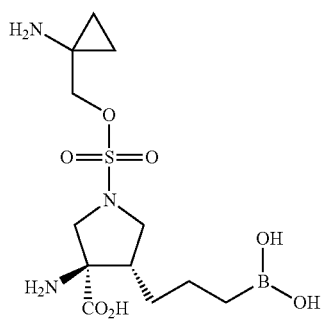
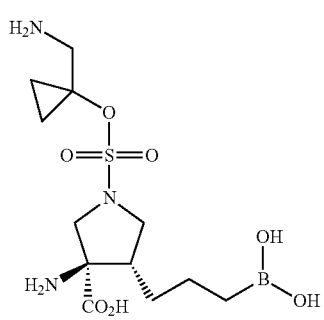
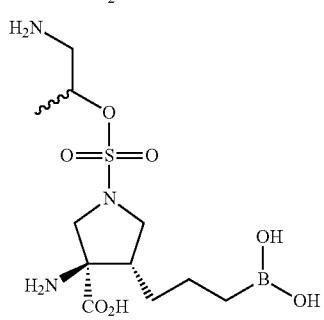
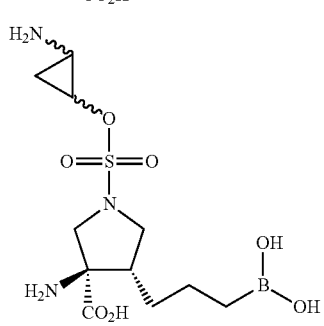
-continued
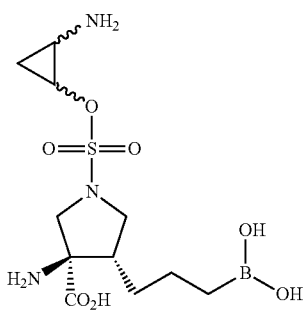
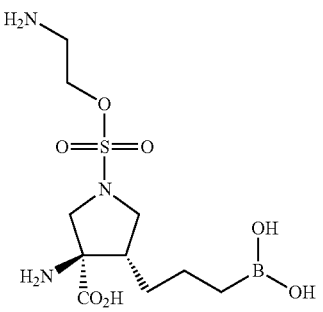
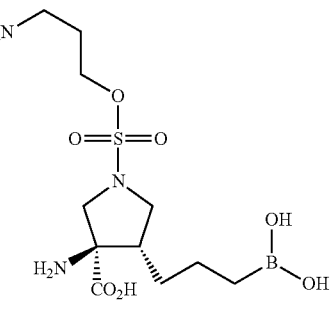
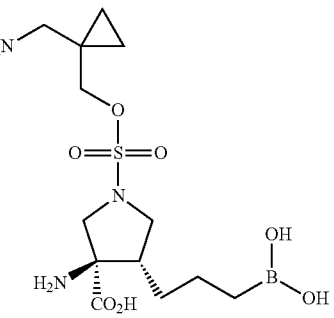
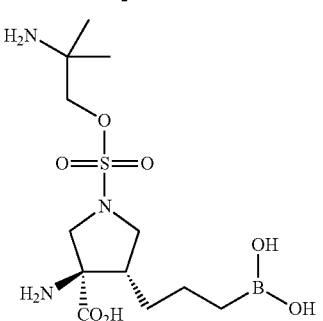

25
-continued
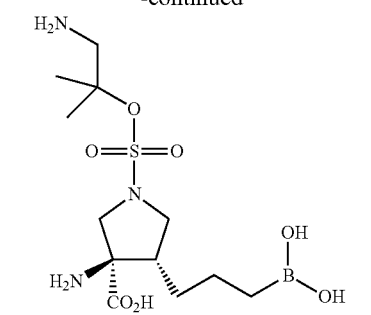
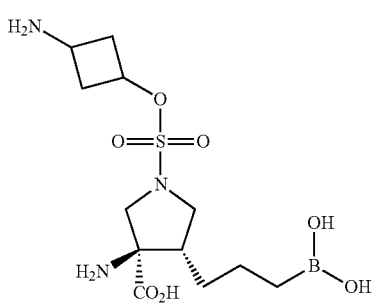
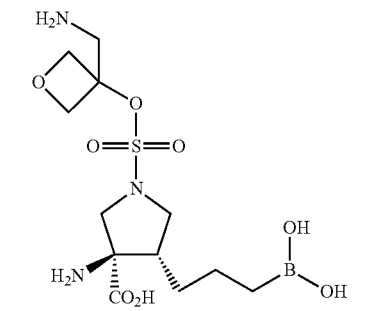
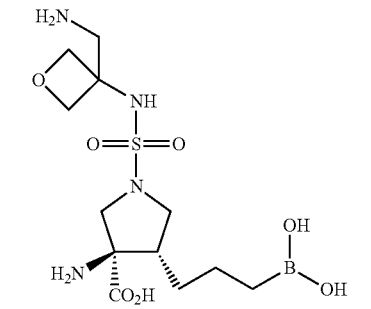
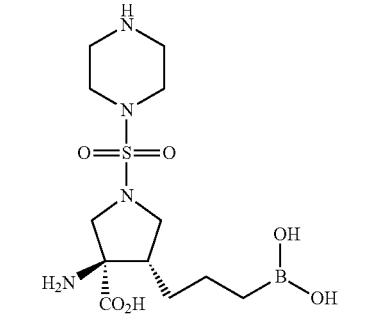
26
-continued
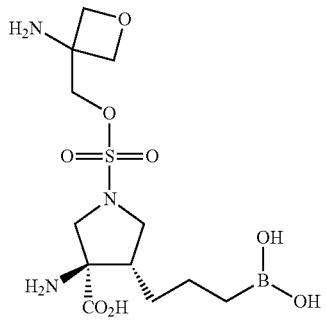
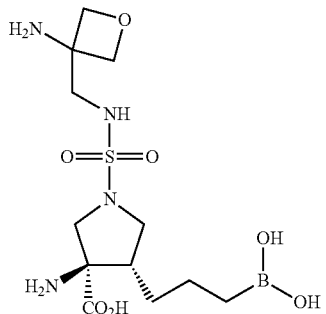
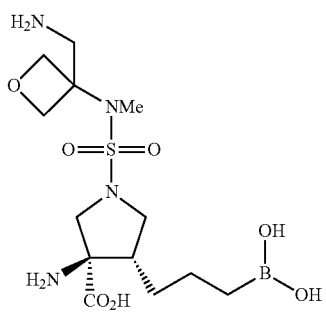
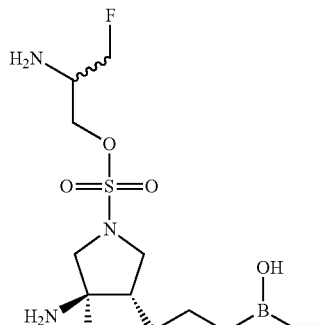
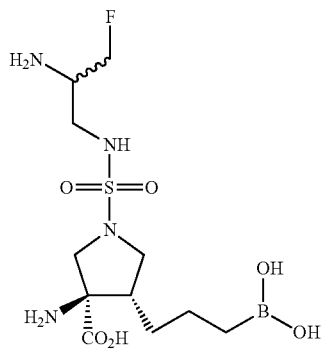

27
-continued
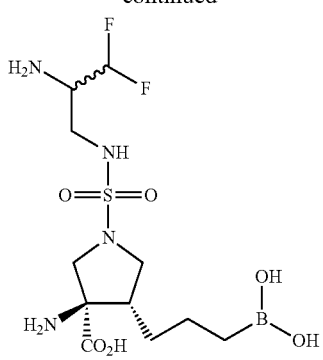
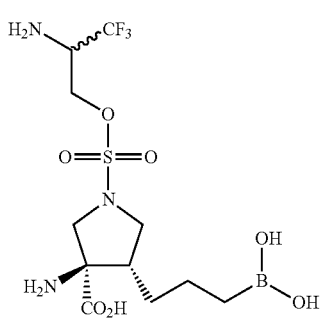
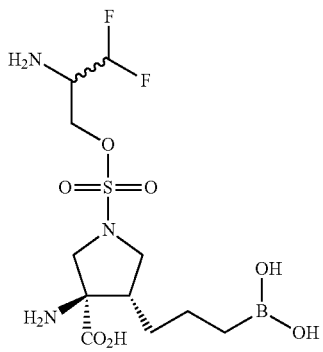
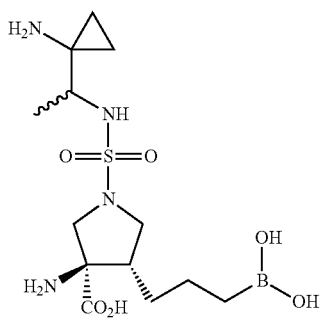
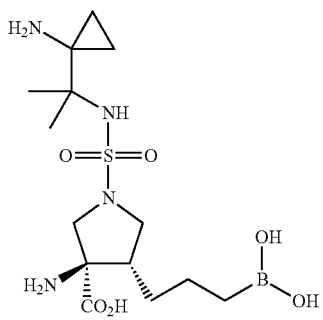
28
-continued
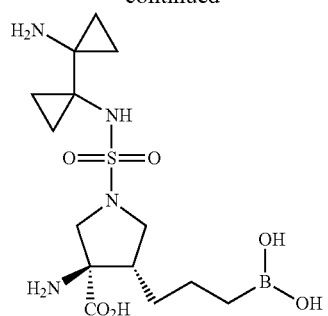
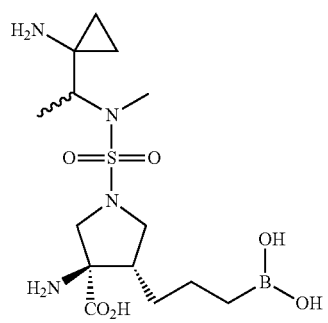
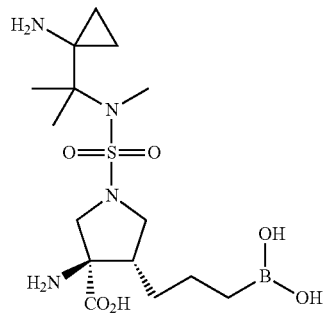
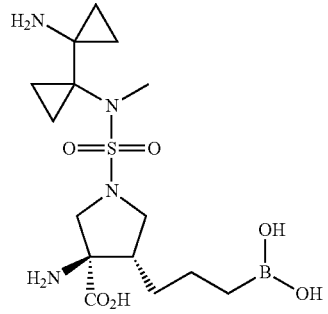
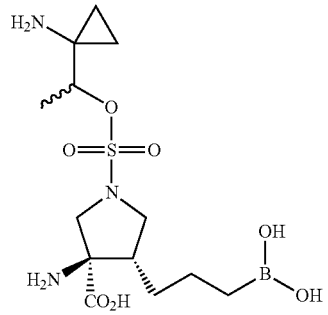

29
-continued
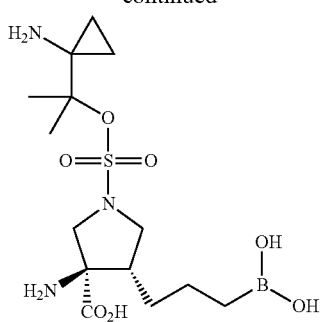
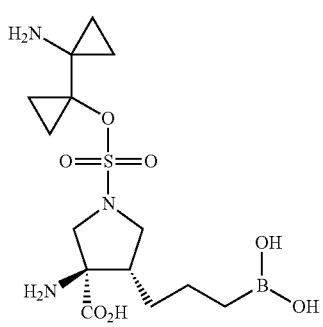
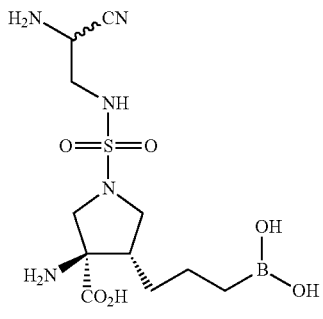
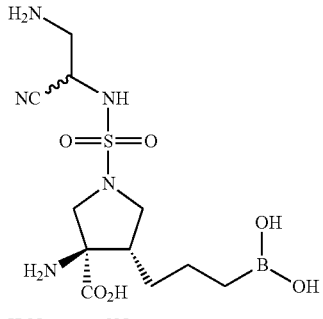
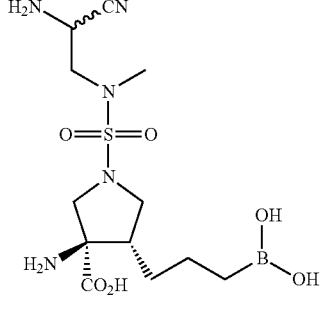
30
-continued
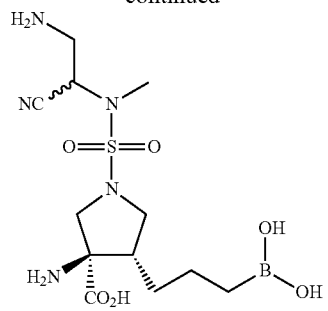
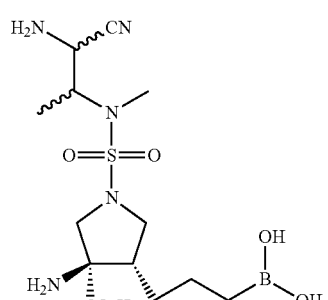
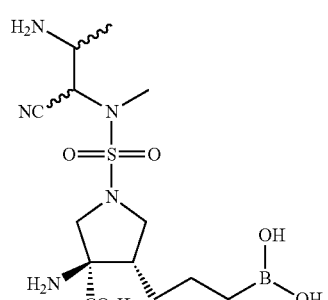
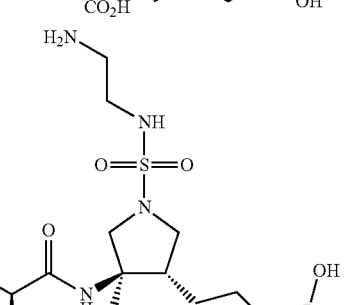
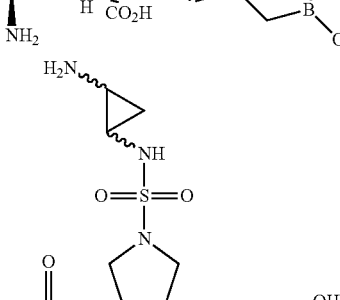

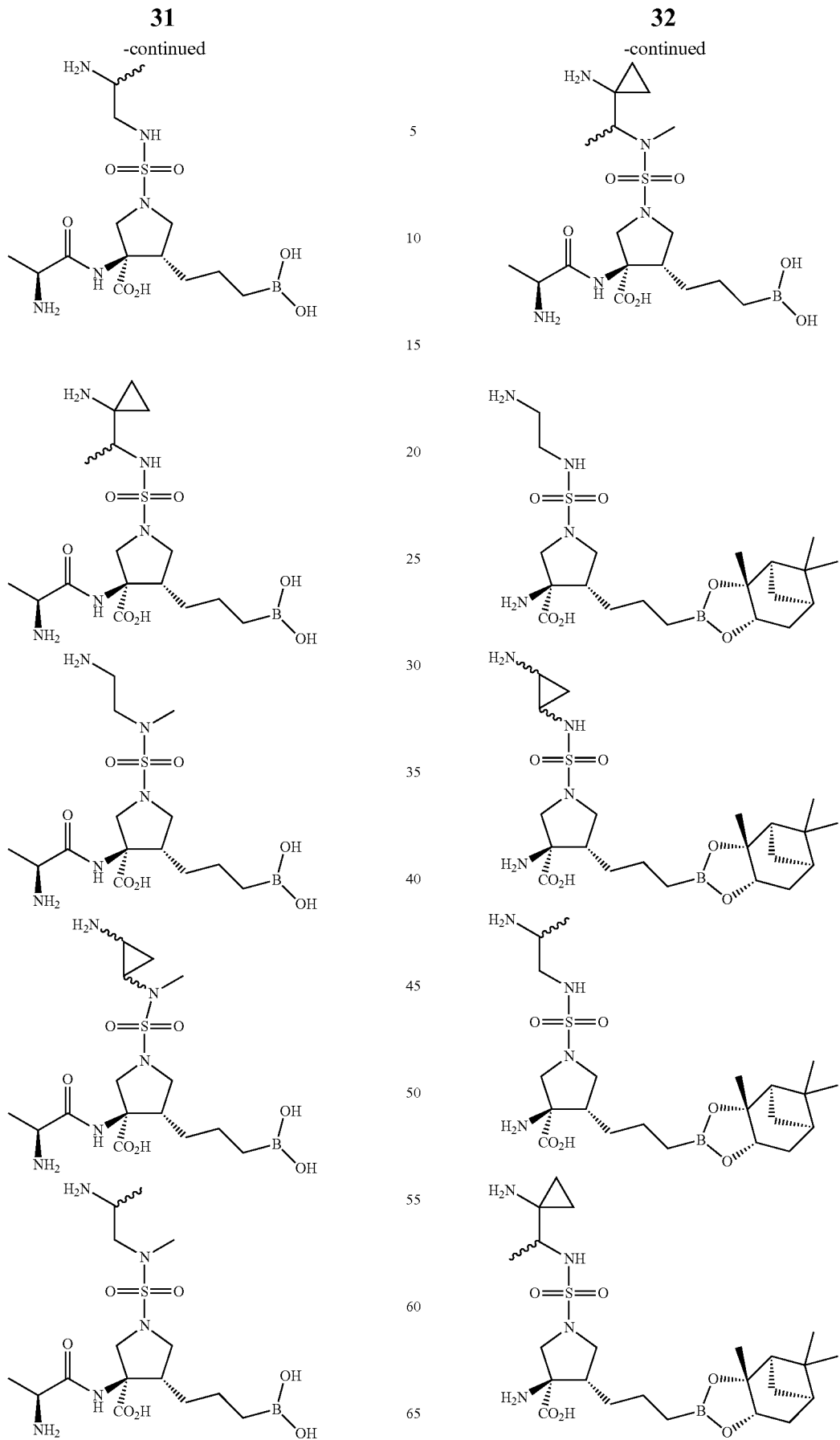

33
-continued
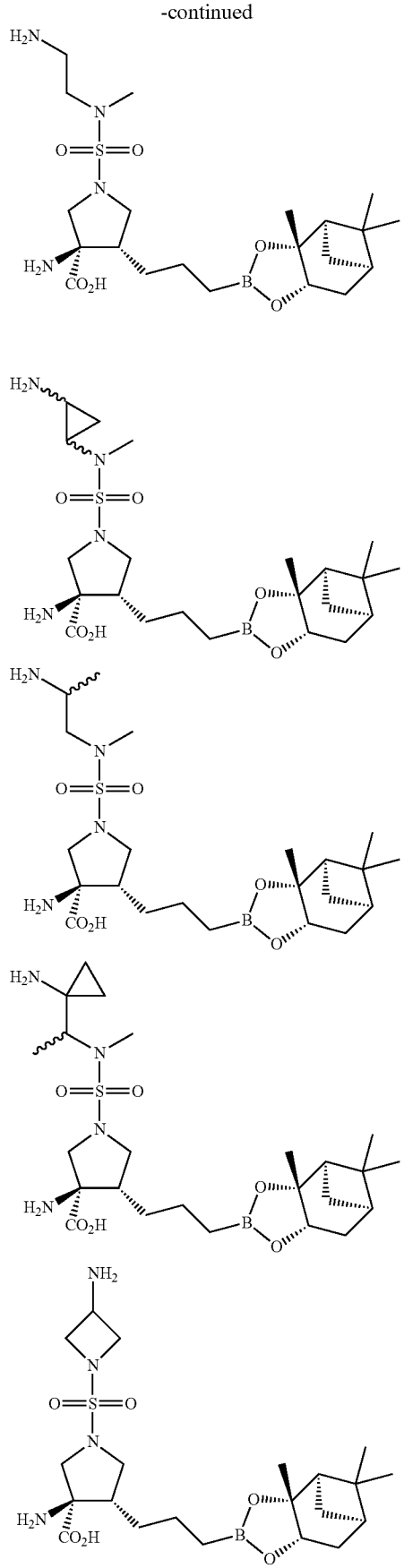
34
-continued
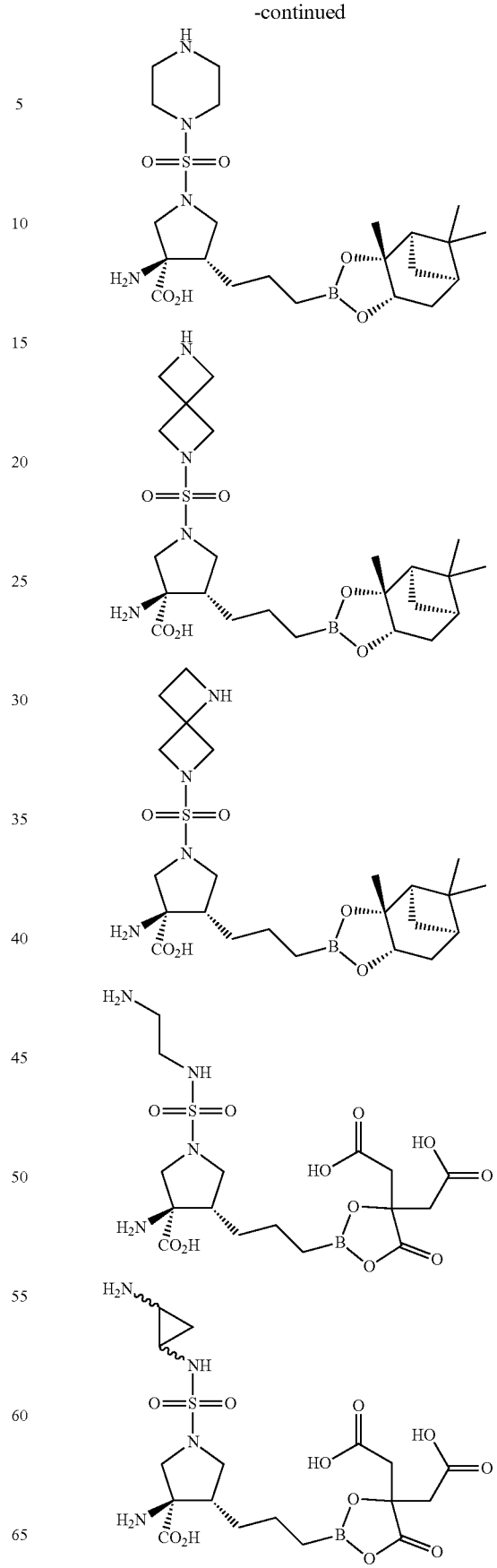

-continued
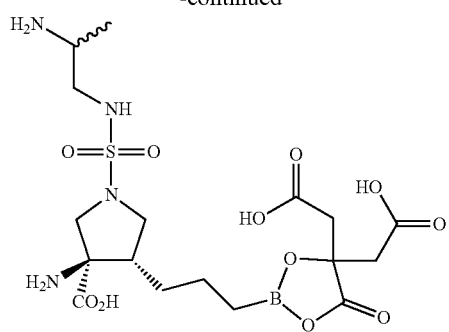
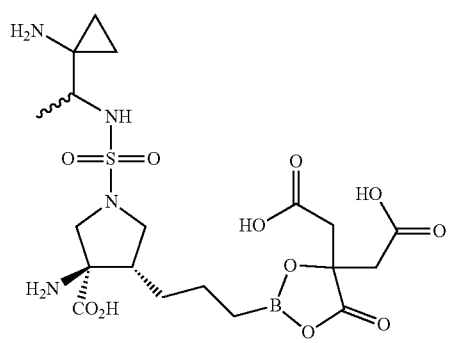
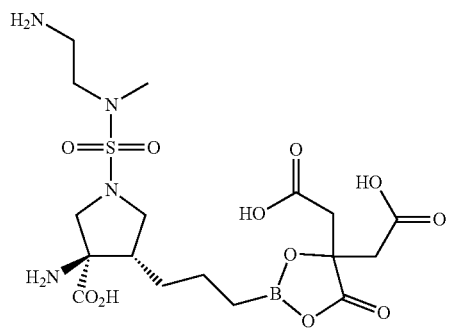
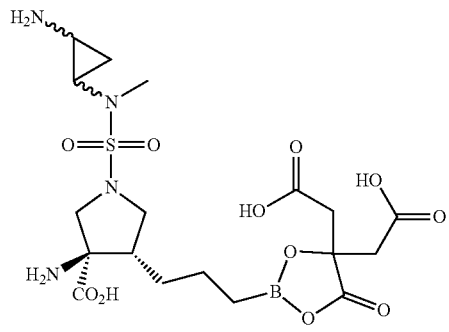
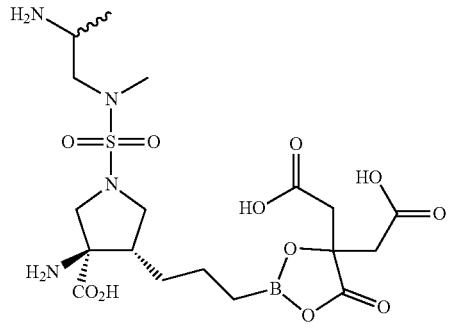
-continued
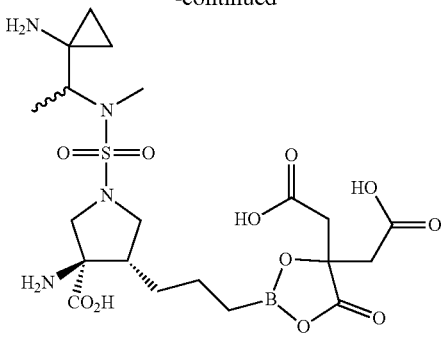
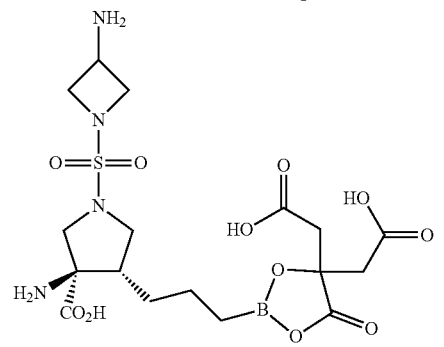
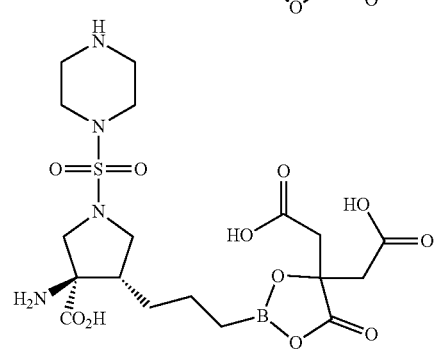
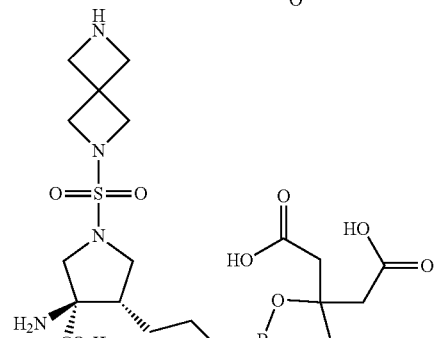
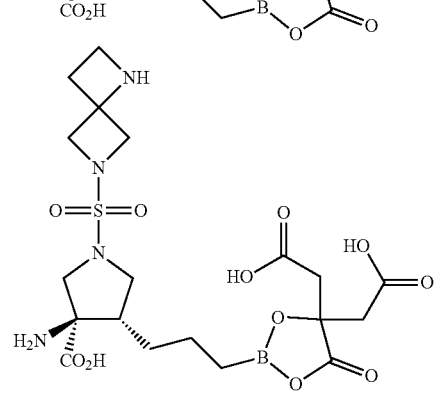

-continued

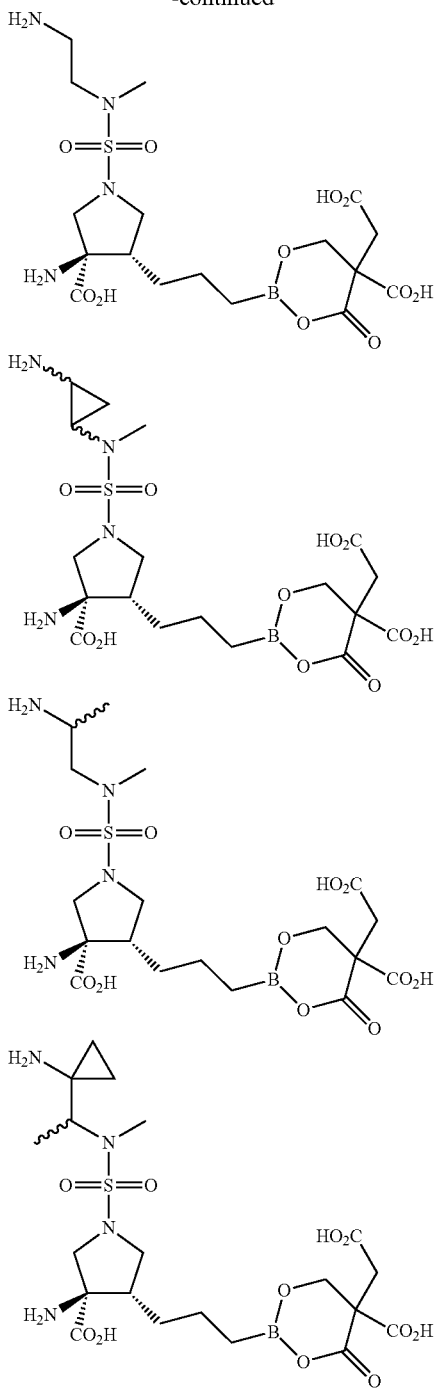

In another preferred embodiment, the compound is a racemate.

In another preferred embodiment, the compound is an enantiomer.

In another preferred embodiment, the pharmaceutically acceptable salt is selected from the group consisting of: sodium, potassium, calcium, ammonium, hydrochloride, hydrobromide, sulfates, phosphates, methanesulfonates, benzenesulfonates, p-toluenesulfonates, 1-naphthalenesulfonate, 2-naphthalenesulfonate, acetate, malate, tartrate, citrate, lactate, oxalate, succinate, fumarate, maleate, benzoate, salicylate, phenylacetate, mandelate.

In another embodiment, a pharmaceutical composition comprising a compound of the present invention and a pharmaceutically acceptable carrier are provided.

In one aspect of the present invention, a use of the compound of Formula (I) according to the first aspect is provided, wherein the use is for:

(i) the preparation of an arginase inhibitor;

(ii) the preparation of a medicament for the prevention and/or treatment of arginase-mediated diseases.

In another preferred embodiment, said arginase-mediated diseases are diseases characterized by the pathologic characteristics of arginase-mediated arginine metabolic pathways.

In another preferred embodiment, said arginase-mediated diseases are cancer, eye diseases, kidney diseases, inflammatory disorders, and autoimmune diseases.

In another preferred embodiment, said cancer includes, but is not limited to: colon cancer, breast cancer, stomach cancer, lung cancer, colorectal cancer, pancreatic cancer, ovarian cancer, prostate cancer, bladder cancer, kidney cancer, liver cancer, esophageal cancer, head and neck cancer, brain cancer, melanoma, multiple myeloma, chronic myeloid leukemia, blood tumor, lymphoid tumor, including metastatic lesions in other tissues or organs that are away from the primary site of tumor.

In another aspect of the present invention, a method for preparing the compound of Formula (I) according to the following schemes is provided:

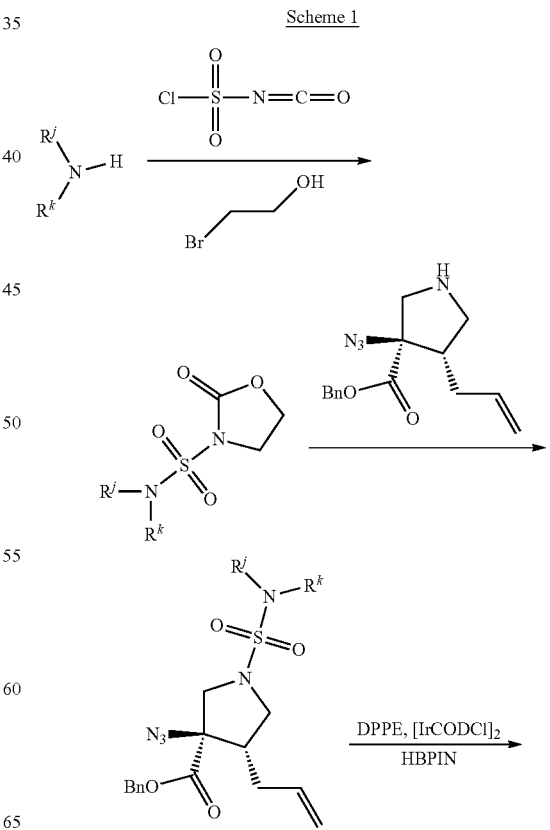

Scheme 1

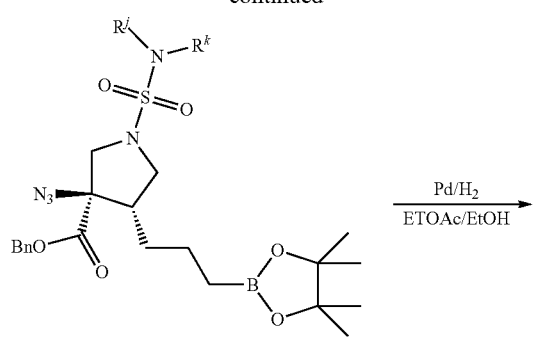
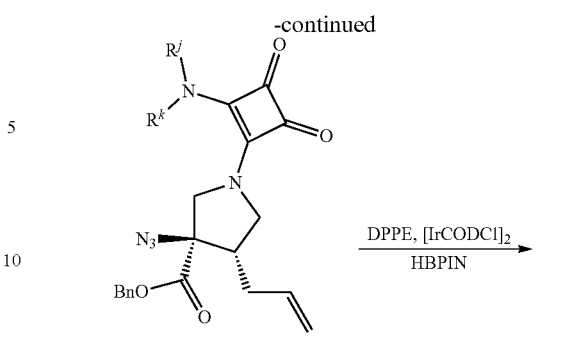
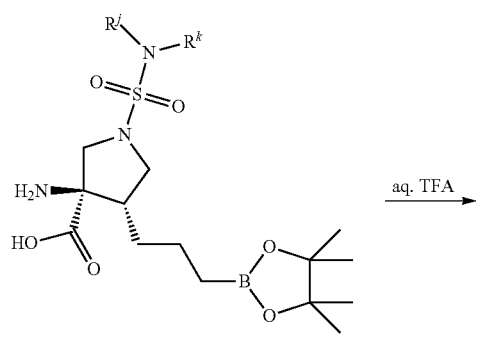
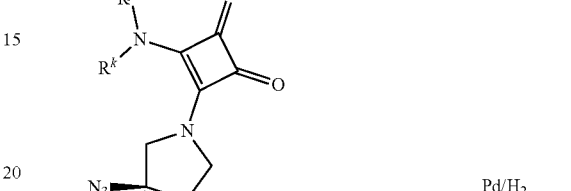
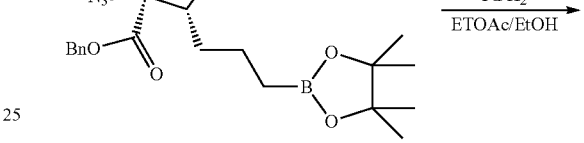
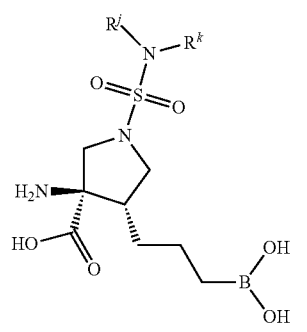
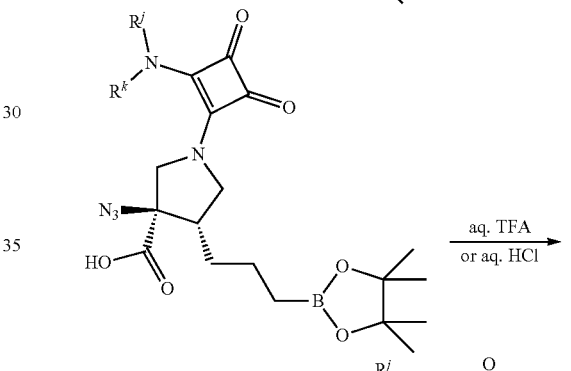

Scheme 2

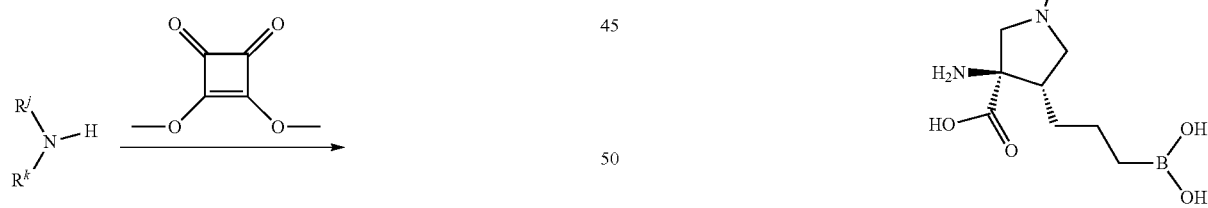

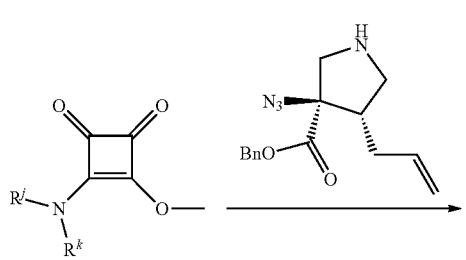

In yet another aspect of the present invention, a combination pharmaceutical composition is provided, wherein the pharmaceutical composition comprises: the compound represented by Formula (I), or its pharmaceutically acceptable salt, stereoisomer or tautomer, or prodrug; and an antineoplastic agent.

In another preferred embodiment, the antineoplastic agent includes, but is not limited to, immunotherapeutic drugs for cancer: PD-1 antibody, CTLA-4 antibody, PD-L1 antibody, PD-L2 antibody, adoptive cell transfer immunotherapy, cancer vaccines, IDO inhibitor, TDO inhibitor, IDO/TDO dual inhibitor, EP4 antagonist, HDAC inhibitor, STING agonist, kinase inhibitor, any other chemotherapeutic agent or targeted therapy agent, radiation therapy.

DEFINITION

Abbreviations used herein have their conventional meaning within the chemical and biological arts.

alkylgroup, means a straight-chain (i.e., unbranched), or branched hydrocarbon chain that is completely saturated. Examples of alkyl include, but are not limited to, groups such as methyl, ethyl, n-propyl, isopropyl, n-butyl, t-butyl, isobutyl, sec-butyl, n-pentyl, n-hexyl, n-heptyl, n-octyl, and the like.

alkenyl refers to a straight-chain (i.e., unbranched), or branched hydrocarbon chain that has one or more double bonds. Examples of alkenyl include, but are not limited to, groups such as vinyl, 2-propenyl, crotyl, 2-isopentenyl, 2-0(butadienyl), 2,4-pentadienyl, 3-(1,4, pentadienyl), alkynyl refers to a straight-chain (i.e., unbranched), or branched hydrocarbon chain that has one or more triple bonds. Examples of alkynyl include, but are not limited to, groups such as ethynyl, 1- and 3-propynyl, 3-butynyl, aryl refer to an aromatic carbocyclic moiety having one or more closed rings. Examples include, without limitation, phenyl, naphthyl, anthracenyl, phenanthracenyl, biphenyl, and pyrenyl.

Halogen of halo refers to chloro (Cl), fluoro (F), bromo (Br) or iodo (I).

Haloalkyl or halogenated alkyl refer to one or more halo groups appended to the parent molecular moiety through an alkyl group. Examples include, but are not limited to, chloromethyl, fluoromethyl, trifluoromethyl, etc Alkoxy or alkylthio refers to an alkyl, alkenyl, or alkynyl group as previously defined, attached to the principal carbon chain through an oxygen ("alkoxy") or sulfur ("alkylthio") atom. Representative examples of "alkoxy" include, but are not limited to, methoxy, ethoxy, propoxy, phenoxy, 2-propoxy, butoxy, tert-butoxy, pentyloxy, hexyloxy and the like.

Cycloalkyl or Cyclyl or carbocycle refers to a saturated cyclic hydrocarbon group containing from 3 to 8 carbons or more. Representative examples of cycloalkyl include, but are not limited to, cyclopropyl, cyclobutyl, cyclopentyl, cyclohexyl, cycloheptyl, and cyclooctyl.

Cycloalkenyl refers to an unsaturated cyclic hydrocarbon group containing from 3 to 8 carbons or more having one or more double bonds The term "Cycloalkoxy" means cycloalkyl as defined above bonded to an oxygen atom, such as cyclopropyloxy.

The term "Halogenated alkoxy" means alkoxy as defined above wherein one or more hydrogen atoms have been replaced by halogen atoms.

Hydroxyl refers to an —OH group.

—OR refers to an R group appended to the parent molecular moiety through an oxy group, wherein R is alkyl, alkenyl, alkynyl, aryl, cycloalkyl, heterocyclyl, or heteroaryl. Representative examples of "—OR" include, but are not limited to, methoxy, ethoxy, propoxy, phenoxy, 2-propoxy, butoxy, tert-butoxy, pentyloxy, hexyloxy and the like.

Carbonyl is a group having a carbon atom double-bonded to an oxygen atom (C—O), often depicted in chemical formula as C(O).

Acetyl is a group —C(O)CH$_3$.

An "amine" or "amino" refers to a group NH$_2$, wherein none, one or two of the hydrogens may be replaced by a suitable substituent as described herein, such as alkyl, alkenyl, alkynyl, and the like.

An amide or amido refers to a group having a carbonyl bonded to a nitrogen atom, such as —C(O)NH$_2$, wherein none, one or two of the hydrogens may be replaced by a suitable substituent as described herein, such as alkyl, alkenyl, alkynyl, and the like.

"—SR" refers to an R group appended to the parent molecular moiety through a sulfur atom, wherein R is alkyl, alkenyl, alkynyl, aryl, cycloalkyl, heterocyclyl, or heteroaryl. Representative examples of "—SR" include, but are not limited to, ethanethiol, 3-methyl-1-butanethio, phenylthio and the like.

Heteroatom refers to O, S or N.

The term "heteroalkyl," by itself or in combination with another term, means, unless otherwise stated, a stable straight or branched chain, or cyclic hydrocarbon radical, or combinations thereof, saturated or unsaturated, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, heteroalkylene by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The term "heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

Heteroaryl refers to a cyclic moiety having one or more dosed rings, with one or more heteroatoms (oxygen, nitrogen or sulfur) in at least one of the rings, wherein at least one of the rings is aromatic, and wherein the ring or rings may independently be fused, and/or bridged. Examples include, without limitation, quinolinyl, isoquinolinyl, indolyl, furyl, thienyl, pyrazolyl, quinoxalinyl, pyrrolyl, indazolyl, thieno[2,3-c]pyrazolyl, benzofuryl, pyrazolo[1,5-a]pyridyl, thiophenylpyrazolyl, benzothienyl, benzothiazolyl, thiazolyl, 2-phenylthiazolyl, and isoxazolyl.

In the above heteroaryl and heterocyclyl the nitrogen or sulfur atoms can be optionally oxidized to various oxidation states.

The term Alkylene, alkenylene, alkynylene, arylene, heteroarylene, cycloalkylene, cylcoalkylene, heterocyclylene, by itself or as part of another substituent means a divalent radical derived from an alkyl, alkenyl, alkynyl, arenyl, heteroarenyl, cycloalkyl, heterocyclyl, as exemplified, but not limited, by —CH$_2$CH$_2$CH$_2$CH$_2$—, —CH$_2$CH=CHCH$_2$—, —CH$_2$C≡CCH$_2$—, —CH$_2$CH$_2$CH(CH$_2$CH$_2$CH$_3$)CH$_2$—.

For convenience, nitrogens, particularly, but not exclusively, those defined as annular aromatic nitrogens, are meant to include those corresponding N-oxide forms.

The said substituted means substituted by substituents selected from the group consisting of halogen atoms, alkyl groups having from 1 to 4 carbon atoms, alkoxy groups having from 1 to 4 carbon atoms, haloalkyl groups having from 1 to 4 carbon atoms, haloalkoxy groups having from 1 to 4 carbon atoms, cyano groups, alkynyl groups having from 2 to 6 carbon atoms, alkanoyl groups having from 1 to 5 carbon atoms, cycloalkyl groups having from 3 to 7 ring atoms, heteroaryl groups, aryl groups, aralkoxy groups having from 7 to 10 carbon atoms, arylcarbonyl groups, two adjacent-x groups are optionally joined together to form an alkylene or an alkenylene chain having 3 or 4 carbon atoms, aminocarbonyl groups, alkenyl groups having from 2 to 5 carbon atoms, alkylthio groups having from 1 to 4 carbon atoms, aminosulfinyl groups, aminosulfonyl groups, hydroxy groups, —SF$_5$, hydroxyalkyl groups having from 1 to 4 carbon atoms, nitro groups, amino groups, carboxy groups, alkoxycarbonyl groups having from 2 to 5 carbon atoms, alkoxyalkyl groups having from 1 to 4 carbon atoms, alkylsulfonyl groups having from 1 to 4 carbon atoms, alkanoylamino groups having from 1 to 4 carbon atoms, alkanoyl(alkyl)amino groups having from 1 to 6 carbon atoms, alkanoylaminoalkyl groups having from 1 to 6 carbon atoms in both the alkanoyl and alkyl part, alkanoyl (alkyl)aminoalkyl groups having from 1 to 6 carbon atoms in both the alkanoyl and each alkyl part, alkylsulfonylamino groups having from 1 to 4 carbon atoms, mono- or di-alkylaminocarbonyl groups having from 1 to 6 carbon atoms, mono- or di-alkylaminosulfinyl groups having from 1 to 6 carbon atoms, mono- or di alkylaminosulfonyl groups having from 1 to 6 carbon atoms, aminoalkyl groups having from 1 to 4 carbon atoms, mono- or di-alkylamino groups having from 1 to 6 carbon atoms, mono- or di-alkylaminoalkyl groups having from 1 to 6 carbon atoms in each alkyl part, aralkyl groups having from 7 to 10 carbon atoms, heteroarylalkyl groups having from 1 to 4 carbon atoms in the alkyl part, heteroarylalkoxy groups having from 1 to 4 carbon atoms in the alkoxy part and alkylsulfonylamino groups having from 1 to 4 carbon atoms;

Unless indicated otherwise, nomenclature used to describe chemical groups or moieties as used herein follow the convention where, reading the name from left to right, the point of attachment to the rest of the molecule is at the right-hand side of the name. For example, the groups "arylC$_{1-6}$alkyl" and NR$^{aa}$R$^{bb}$C$_{1-6}$alkyl" are each attached to the rest of the molecule at the alkyl end.

Unless indicated otherwise, where a chemical group is described by its chemical formula, including a terminal bond moiety indicated by it will be understood that the attachment is read from left to right. For example, —NR$^{aa}$C(O)CH=CH$_2$ is attached at the nitrogen.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Enantiomeric excess" (ee) of an enantiomer is [(the mole fraction of the major enantiomer) minus (the mole fraction of the minor enantiomer)]×100.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrugs may also have improved solubility in pharmaceutical compositions over the parent drug. An example, without limitation, of a prodrug would be a compound of any of Formula I-XIV, which is administered as an ester (the "prodrug") to facilitate transmittal across a cell membrane where water solubility is detrimental to mobility, but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Optical Isomers-Diastereomers-Geometric Isomers-Tautomers

Compounds of Formula I-XIV may contain one or more asymmetric centers and may thus occur as racemates and racemic mixtures, single enantiomers, diastereomeric mixtures and individual diastereomers. The present invention is meant to comprehend all such isomeric forms of the compounds of Formula I-XIV.

Some of the compounds described herein contain olefinic double bonds, and unless specified otherwise, are meant to include both E and Z geometric isomers.

Some of the compounds of Formula I-XIV may contain one or more than one cyclic ring systems and may thus exist in cis- and trans-isomers. The present invention is meant to include all such cis- and trans-isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I-XIV.

Compounds of the Formula I-XIV may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine or acid as a resolving agent or on a chiral HPLC column.

Alternatively, any enantiomer of a compound of the general Formula I-XIV may be obtained by stereospecific synthesis using optically pure starting materials or reagents of known configuration.

Stable Isotope-Labeled Analogs

One or more than one of the protons in compounds of Formula I-XIV can be replaced with deuterium atom(s), thus providing deuterated analogs that may have improved pharmacological activities.

Pharmaceutical Compositions

A pharmaceutical composition is also provided by the present invention, comprising an active ingredient within a safe and effective dosage, and a pharmaceutically acceptable carrier.

The "active ingredient" in the present invention refers to the compound of Formula (I)-(XII) or a pharmaceutically acceptable salt, stereoisomer or tautomer, prodrug thereof according to the present invention.

The "active ingredient" and pharmaceutical compositions in the present invention can be used as an arginase inhibitor. In another preferred embodiment, for the preparation of a medicament for the prevention and/or treatment of tumors. In another preferred embodiment, for the preparation of a medicament for the prevention and/or treatment of arginase-mediated diseases.

"a safe and effective dosage" means: the amount of the active ingredient is sufficient to significantly ameliorate the condition without causing serious side effects. Generally, the pharmaceutical composition contains 1-2000 mg of the active ingredient/dose, more preferably 10 to 200 mg of the active ingredient/dose. Preferably, the "one dose" is a tablet.

"Pharmaceutically acceptable carrier" refers to: one or more compatible solid or liquid fillers or gel materials that are suitable for human use and must have sufficient purity and sufficiently low toxicity. "Compatible" herein means that each component in the composition can be admixed with the active ingredients of the present invention and with each other without significantly reducing the efficacy of the active ingredients.

The compounds of the preferred embodiments of the present invention may be administered as a separate active agent or in combination with one or more other agents for the treatment of cancer. It is effective to use the compounds of the preferred embodiments of the present invention in combination with known therapeutic agents and anti-cancer agents, and combinations of currently known compounds and other anti-cancer agents or chemotherapeutic agents are within the scope of the preferred embodiments. Examples of such agents can be found in *Cancer Principles and Practice of Oncology* V. T. Devita and S. Hellman (editor), 6th edition (Feb. 15, 2001), published by Lippincott Williams &Wilkins. Based on the particular properties of the drugs and the cancer involved, the skilled in the art can identify effective pharmaceutical combinations. Such anti-cancer agents include, but are not limited to: estrogen receptor modulators, androgen receptor modulators, retinol receptor modulators, cytotoxic/cell growth inhibitors, antiproliferative agents, radiation therapy, isopentenyl protein transferase inhibitors, IDO inhibitors, TDO inhibitors, IDO/TDO dual inhibitors, EP4 antagonists, HDAC inhibitors and other angiogenesis inhibitors, cell proliferation and survival signal inhibitors, apoptosis inducers and agents that interfere with cell cycle checkpoint, antibody immunotherapies such as CTLA4 antibody, PD-1 antibody, PD-L1 antibody and the like, cancer vaccines, adoptive cell transfer immunotherapy. In general, the compounds of the preferred embodiments will be administered in a therapeutically effective amount by any of the acceptable modes for an agent having similar effects. The actual usage amounts of the compounds (i.e., the active ingredients) of the preferred embodiments are determined based on a number of factors such as the severity of the disease to be treated, the age and relative health of the patient, the potency of the compound to be used, the route and form of administration, and other factors. The medicament may be administered multiple times a day, preferably once or twice a day. All of these factors are within the scope of the attending physician's consideration.

For the purposes of the preferred embodiment, the therapeutically effective dosage may generally be a daily total dosage administered to a patient in a single or multiple application, for example, about 0.001 to 1000 mg/kg body weight per day, preferably about 1.0 to 30 mg/kg body weight. A dosage unit composition may contain a dose factor to form a daily dose. The choice of dosage form depends on various factors such as the mode of administration and the bioavailability of the drug substance. In general, the compounds of the preferred embodiments may be administered as a pharmaceutical composition by any of the administration routes selected from the group consisting of: oral administration, systemic administration (e.g., transdermal, intranasal or via suppositories), or parenteral administration (e.g., intramuscular, intravenous or subcutaneous). The preferred mode of administration is oral, and the convenient daily dose can be adjusted according to the degree of bitterness. The compositions may take the form of tablets, pills, capsules, semisolids, powders, sustained release formulations, solutions, suspensions, elixirs, aerosols or any other suitable compositions. Another preferred method of administering the compounds of the preferred embodiments is inhalation. This is an effective method for delivering therapeutic agents directly to the respiratory tract (see, e.g., U.S. Pat. No. 5,607,915).

Suitable pharmaceutically acceptable carriers or excipients include: for example, treatment agents and drug delivery modifiers and accelerators, such as calcium phosphate, magnesium stearate, talc, monosaccharides, disaccharides, starches, gelatin, cellulose, sodium methylcellulose, carboxymethylcellulose, glucose, hydroxypropyl-β-cyclodextrin, polyvinylpyrrolidone, low melting wax, ion exchange resin and the like, and combinations of any two or more thereof. Liquid and semi-solid excipients may be selected from glycerol, propylene glycol, water, ethanol and various oils including petroleum, animal oils, vegetable oils or synthetic sources such as peanut oil, soybean oil, mineral oil, sesame oil and the like. Preferred liquid carriers, particularly carriers for injectable solutions, include water, saline, glucose aqueous solution and ethylene glycol. Other suitable pharmaceutically acceptable excipients are described in Remington's Pharmaceutical Sciences, Mack Pub. Co., New Jersey (1991), which is incorporated herein by reference.

As used herein, the phrase "pharmaceutically acceptable salt" refers to a non-toxic acid or alkaline earth metal salt of the compound of formula I-IV. These salts can be prepared in situ at the final separation and purification of the compounds of formula I-IV, or by reacting a suitable organic or inorganic acid or alkali with an alkaline or acidic functional group, respectively. Representative salts include, but are not limited to: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucose heptylate, glycerophosphate, hemisulfate, heptanoate, hexanoate, fumarate, hydrochloride, hydrobromide, hydriodate, 2-hydroxyethanesulfonate, lactate, maleate, methanesulfonate, nicotinate, 2-naphthyl sulfonate, oxalate, pamoate, pectate, thiocyanate, 3-phenyl propionate, picrate, pivalate, propionate, succinate, sulfate, tartrate, thiocyanate, p-toluenesulfonate and undecanoate. In addition, the N-containing basic groups can be quaternized with the following reagents: alkyl halides such as chlorides, bromides and iodides of methyl, ethyl, propyl, butyl; dialkyl sulfate such as dimethyl, diethyl, dibutyl and dipentyl sulfates; long chain halides such as chlorides, bromides and iodides of decyl, lauryl, myristyl and stearyl; aromatic alkyl halides such as benzyl and benzene ethyl bromide and the like. A water-soluble or oil-soluble or dispersible product is thereby obtained. Examples of acids which may be used to form pharmaceutically acceptable acid addition salts include inorganic acids such as hydrochloric acid, sulfuric acid, phosphoric acid, and organic acids such as oxalic acid, maleic acid, methanesulfonic acid, succinic acid and citric acid. The alkali addition salts may be prepared in situ at the time of final separation and purification of the compounds of formula I, or by reacting the carboxylic acid moieties with a suitable alkali (such as a hydroxide, carbonate or bicarbonate of a pharmaceutically acceptable metal cation), or ammonia, or an organic primary, secondary or tertiary amine, respectively. Pharmaceutically acceptable salts include, but are not limited to, salts based on cations of alkali and alkaline earth metals, such as sodium, lithium, potassium, calcium, magnesium, aluminum and the like, and non-toxic ammonium, quaternary ammonium and amine cations, including but not limited to, ammonium, tetramethylammonium, tetraethylammonium, methylamine, dimethylamine, trimethylamine, triethylamine, ethylamine and the like. Other representative organic amines used to form the alkali addition salts include diethylamine, ethylenediamine, ethanolamine, diethanolamine, piperazine and the like.

As used herein, the term "pharmaceutically acceptable prodrugs" refer to the prodrugs of the compounds of the preferred embodiments, which are compounds rapidly converted in vivo into the parent compounds represented by the above general formulas, for example, by being hydrolyzed in the blood. Full discussion was provided in "T. Higuchi and V. Stella, Pro-drugs as Novel Delivery Systems, A.C.S., Vol. 14 of 15 Symposium Series" and "Edward B. Roche, eds., Bioreversible Carriers in Drug Design, American Pharmaceutical Association and Pergamon Press, 1987", both of which are incorporated herein by reference.

Arginase Inhibitory Activity Test

An enzymatic assay with recombinant human arginases 1 or 2 was used to measure inhibitory activity of the compounds. The assay is based on urea measurement, which is a product of L-arginine enzymatic degradation. (Baggio et al. J. Pharmacol. Exp. Ther. 1999, 290, 1409-1416).

Briefly, arginase and the substrate solution containing L-arginine were incubated in the absence or presence of varying concentrations of compounds at 37° C. for 120 min. For the background correction, only the substrate solution was added without arginase. The urea detection reagent from QuantiChrome TM Urea assay kit (BioAssay Systems, CA) was added to develop the color product. After 60 min at room temperature, the absorbance was measured at 450 nm with CLARIOstar (BMG LABTECH). Urea was used as the standard. The $IC_{50}$ values were calculated using MARS data analysis software (A: $IC_{50}$<0.1 μM; B: $IC_{50}$ between 0.1 μM and 1 μM; C: $IC_{50}$ between 1 μM and 101 μM; D: >101 μM; ND: not determined).

$IC_{50}$ of Examples in Arginase 1 and 2 Assays:

| Example No. | Arg 1 enzymatic potency | Arg 2 enzymatic potency |
|---|---|---|
| 1 | A | B |
| 2 | C | ND |
| 3 | B | B |
| 4 | B | B |
| 5 | A | A |
| 6 | B | B |
| 7 | C | ND |
| 8 | B | ND |
| 9 | B | ND |
| 10 | B | ND |
| 11 | C | ND |
| 12 | A | ND |
| 13 | B | ND |
| 14 | B | ND |
| 15 | A | ND |
| 16 | A | ND |
| 17 | A | ND |
| 18 | B | ND |
| 19 | B | ND |
| 20 | D | ND |
| 21 | B | ND |
| 22 | B | ND |
| 23 | B | ND |
| 24 | A | ND |
| 25 | A | A |
| 26 | A | A |

The following abbreviations have the meanings indicated. DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis(diphenylphosphino)ferrocene; dppm means 1,1'-bis(diphenylphosphino)methane; DIAD means diisopropylazodicarboxylate; EDCI means 1-(3-dimethylaminopropyl)-3-ethylcarbodiimide; HATU means 2-(7-Aza-1H-benzotriazole-1-yl)-1,1,3,3-tetramethyluronium hexafluorophosphate; HMPA means hexamethylphosphoramide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA means tris(2-(2-methoxyethoxy)ethyl)amine; DCM means dichloromethame; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine, RT means room temperature.

HPLC-MS analyses were performed on Waters HPLC 2790 with Waters micromass ZQ 4000 (Model MAA050) as mass detector and Waters 2487 UV as detector. Column used was Phenomemex OOB-4605-E0 (5u-XB-C18-100A, 50×4.6 mm). The mobile phase consists eluent A (water, 0.05% TFA) and eluent B ($CH_3CN$, 0.05% TFA), and the elution proceeded at 1 mL/min. The initial conditions were 90% A for 1 min, then 90% A to 10% A linearly decreased within 5 min, then from 10% A to 90% A within 1 min. The total run time is 7 minutes.

All final compounds were purified by reverse phase preparative HPLC using Waters xbridge Prep C18 5 μm 19 mm×150 mm column. Preparation Temperature is r.t. mobile phase: A: 0.1% Trifluoroacetic acid in Water; B: Acetonitrile. Gradient: 2% to 50%. Elution rate: 15 mL/min. compound collection verified by MS.

The present invention will be more readily understood by referring to the following examples which are given to illustrate the invention rather than to limit its scope.

Example 1

(rac)trans-3-amino-4-(3-boronopropyl)-1-sulfamoylpyrrolidine-3-carboxylic acid, (1:1) 2,2,2-trifluoroacetic Acid Salt

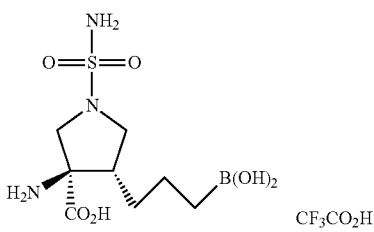 [SMILES: N[C@@]1(C(=O)O)CN(S(N)(=O)=O)C[C@@H]1CCCB(O)O ; "CF3CO2H"]

Step 1 (rac)benzyl trans-4-allyl-3-azido-1-sulfamoylpyrrolidine-3-carboxylate

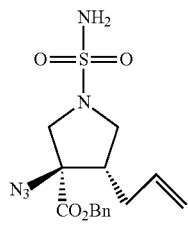 [SMILES: C=CC[C@H]1CN(S(N)(=O)=O)C[C@@]1(N=[N+]=[N-])C(=O)OCc1ccccc1]

A solution of (rac)benzyl trans-4-allyl-3-azidopyrrolidine-3-carboxylate (0.200 g, 0.698 mmol) and triethylamine (0.212 g, 2.095 mmol) in THF (5 mL) was added to the solution of sulfamoyl chloride (0.242 g, 2.095 mmol) in THF (5 mL) at r.t. and the reaction was stirred overnight. Then, the reaction mixture was concentrated and purified by silica gel flash chromatography (EA:PE=10 to 40%) to give 0.151 g of title compound as a yellow oil. Yield: 59%. MS (ES+): 366 [M+1]$^+$.

Step 2 (rac)benzyl trans-3-azido-1-sulfamoyl-4-(3-(4,4,5,5-tetramethyl-1,3,2-dioxaborolan-2-yl)propyl)pyrrolidine-3-carboxylate

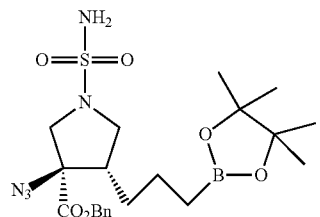

A solution of the product of Step 1 (0.151 g, 0.410 mmol), bis (1,5-cyclootadiene) diiridium dichloride (0.055 g, 0.082 mmol) and 1,2-bis (diphenyphosphino) ethane (0.065 g, 0.164 mmol) in DCM (2 mL) was stirred for 30 min under $N_2$ atmosphere. Then, a solution of 4,4,5,5-tetramethy [1,3,2]dioxaborolane (0.262 g, 2.050 mmol) in DCM (2 mL) was added dropwise at 0° C. The reaction mixture was allowed to warm to r.t. and stirred overnight. Then the mixture was concentrated and purified by silica gel flash chromatography (EA:PE=20 to 40%) to give 0.15 g of the title compound as a yellow oil. Yield: 75%. MS (ES+): 494 [M+1]$^+$.

Step 3 (rac)trans-3-amino-1-sulfamoyl-4-(3-(4,4,5,5-tetramethyl-1,3,2-dioxaborolan-2-yl)propyl)pyrrolidine-3-carboxylic Acid

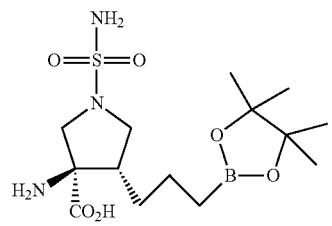

The product of step 2 (0.150 g, 0.410 mmol) was dissolved in a 1:1 mixture of ethyl acetate and ethanol (4 mL). 10% Pd—C (10 mg) was added and the solution was degassed under vacuum and purged with $H_2$. The solution was stirred at $H_2$ atmosphere at r.t. overnight. The reaction mixture was filtered through a 4 syringe filter to remove the palladium catalyst and concentrated to dryness under vacuum and used without further purification. MS (ES+): 378[M+1]$^+$.

Step 4 (rac)trans-3-amino-4-(3-boronopropyl)-1-sulfamoylpyrrolidine-3-carboxylic acid, (1:1) 2,2,2-trifluoroacetic Acid Salt

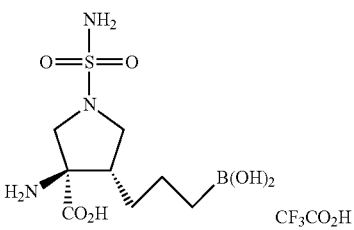 [SMILES: N[C@@]1(C(=O)O)CN(S(N)(=O)=O)C[C@@H]1CCCB(O)O ; "CF3CO2H"]

A suspension of the product from step 3 in 4 N hydrochloric acid (3 mL) was stirred at 50° C. overnight and then cooled to r.t. The solution was concentrated under vacuum and purified by reverse phase HPLC to give 0.020 g of the title compound. Yield: 17% over 2 steps. MS (ES+): 278 [M−18+1]$^+$.

$^1$HNMR Spectrum: (400 MHz, $D_2O$) δ 3.84 (d, J=12.0 Hz, 1H), 3.69 (m, 1H), 3.47 (d, J=12.0 Hz, 1H), 3.15-3.02 (m, 1H), 2.57-2.47 (m, 1H), 1.57-1.48 (m, 1H), 1.43-1.22 (m, 3H), 0.79-062 (m, 2H).

Example 2

(rac)trans-3-amino-4-(3-boronopropyl)-1-(N-methyl-sulfamoyl)pyrrolidine-3-carboxylic acid, (1:1) 2,2,2-trifluoroacetic Acid Salt

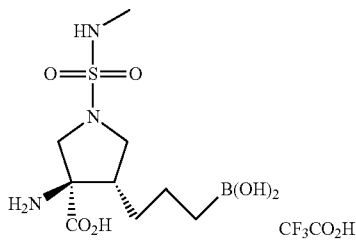 [SMILES: CNS(=O)(=O)N1C[C@H](CCCB(O)O)[C@](N)(C(=O)O)C1 ; "CF3CO2H"]

Using (rac)benzyl trans4-allyl-3-azidopyrrolidine-3-carboxylate and methylsulfamoyl chloride as starting materials, the title compound was prepared according to the same procedures described for Example 1.

MS (ESI, m/e): 292 [M-H$_2$O+1]$^+$.

$^1$HNMR Spectrum: (400 MHz, D$_2$O) δ 3.84 (d, J=12.0 Hz, 1H), 3.69 (m, 1H), 3.47 (d, J=12.0 Hz, 1H), 3.18-3.07 (m, 1H), 2.62 (s, 3H), 2.50-2.40 (m, 1H), 1.57-1.48 (m, 1H), 1.43-1.22 (m, 3H), 0.79-0.62 (m, 2H).

Example 3

(rac)trans-3-amino-1-(2-amino-3,4-dioxocyclobut-1-en-1-yl)-4-(3-boronopropyl)pyrrolidine-3-carboxylic Acid, (1:1) 2,2,2-trifluoroacetic Acid Salt

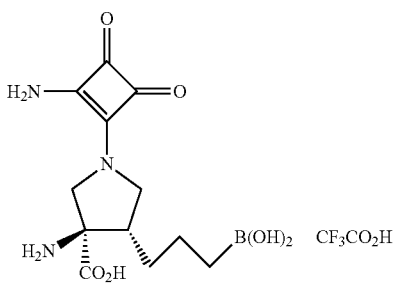 [SMILES: Nc1c(N2C[C@H](CCCB(O)O)[C@](N)(C(=O)O)C2)c(=O)c1=O ; "CF3CO2H"]

Step 1 3-amino-4-methoxycyclobut-3-ene-1,2-dione

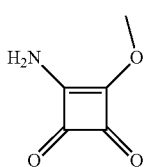

The 3,4-dimethoxycyclobut-3-ene-1,2-dione (3.000 g, 21.110 mmol) was dissolved in MeOH and NH$_3$ (7 M in MeOH) (3 mL, 21.000 mmol) was added dropwise at r.t. The reaction was stirred overnight at r.t. and concentrated, purified by silica gel flash chromatography (CH$_2$Cl$_2$:MeOH=0 to 30%) to give 1.0 g of the title compound. Yield: 37%. MS (ESI, m/e): 128 [M+1]$^+$.

Step 2 (rac)benzyl trans-4-allyl-1-(2-amino-3,4-dioxocyclobut-1-en-1-yl)-3-azidopyrrolidine-3-carboxylate

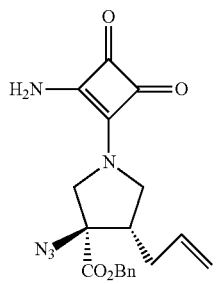 [SMILES: C=CC[C@H]1CN(c2c(N)c(=O)c2=O)C[C@@]1(N=[N+]=[N-])C(=O)OCc1ccccc1]

(rac)Benzyl trans-4-allyl-3-azidopyrrolidine-3-carboxylate (0.300 g, 1.222 mmol) and the product of step 1 (0.233 g, 1.833 mmol) was stirred in DMF (2 mL) for 5 h at 80° C. The reaction mixture was then concentrated and purified by silica gel flash chromatography (MeOH:DCM=0 to 5%) to give 0.14 g of the title compound. Yield: 30%. MS (ESI, m/e): 382 [M+1]$^+$.

Step 3 (rac)benzyl trans-1-(2-amino-3,4-dioxocyclobut-1-en-1-yl)-3-azido-4-(3-(4,4,5,5-tetramethyl-1,3,2-dioxaborolan-2-yl)propyl)pyrrolidine-3-carboxylate

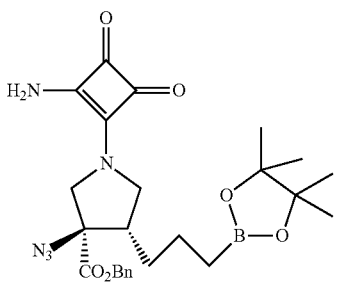 [SMILES: CC1(C)OB(CCC[C@H]2CN(c3c(N)c(=O)c3=O)C[C@@]2(N=[N+]=[N-])C(=O)OCc2ccccc2)OC1(C)C]

A solution of the product of Step 2 (0.140 g, 0.367 mmol), bis (1,5-cyclootadiene) diiridium dichloride (0.049 g, 0.073 mmol) and 1,2-bis (diphenyphosphino) enthane (0.059 g, 0.147 mmol) in DCM (2 mL) was stirred for 30 min under N$_2$ atmosphere. A solution of 4,4,5,5-tetramethy [1,3,2] dioxaborolane (0.235 g, 1.835 mmol) in DCM (2 mL) was then added dropwise a t 0° C. The reaction was allowed to warm to r.t. and stirred overnight. The reaction mixture was then concentrated and purified by silica gel flash chromatography (EA:PE=20-40%) to give 0.07 g of the title compound as a yellow oil. Yield: 37%. MS (ESI, m/e): 510 [M+1]$^+$.

Step 4 (rac)trans-3-amino-1-(2-amino-3,4-dioxocyclobut-1-en-1-yl)-4-(3-(4,4,5,5-tetramethyl-1,3,2-dioxaborolan-2-yl)propyl)pyrrolidine-3-carboxylic Acid

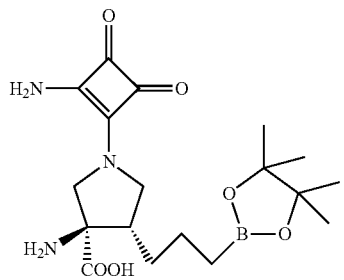 [SMILES: CC1(C)OB(CCC[C@H]2CN(c3c(N)c(=O)c3=O)C[C@@]2(N)C(=O)O)OC1(C)C]

The product of Step 3 (0.070 g, 0.137 mmol) was dissolved in a 1:1 mixture of ethyl acetate and ethanol (4 mL). 10% Pd—C (10 mg) was added and the solution was degassed under vacuum and purged with $H_2$. The solution was stirred at $H_2$ atmosphere at r.t. overnight. The solution was filtered through a 4 syringe filter to remove traces of palladium and concentrated under vacuum to give the crude title compound which was used without further purification. MS (ESI, m/e): 394[M+1]$^+$.

Step 5 (rac)trans-3-amino-1-(2-amino-3,4-dioxocyclobut-1-en-1-yl)-4-(3-boronopropyl)pyrrolidine-3-carboxylic Acid, (1:2) 2,2,2-trifluoroacetic Acid Salt

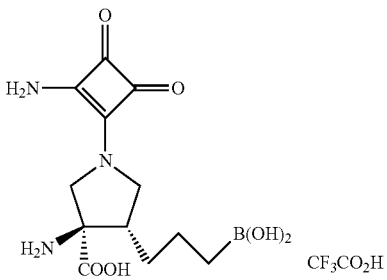 [SMILES: Nc1c(N2C[C@H](CCCB(O)O)[C@](N)(C(=O)O)C2)c(=O)c1=O ; "CF3CO2H"]

A suspension of the product of Step 4 in 4 N hydrochloric acid (1 mL) was stirred at 50° C. overnight and then cooled to r.t. The reaction mixture was then concentrated under vacuum and purified by reverse phase HPLC to give 0.004 g of title compound. Yield: 11% over 2 steps. MS (ESI, m/e): 294 [M-$H_2$O+1]$^+$.

$^1$HNMR Spectrum: (400 MHz, $D_2O$) δ 4.50-4.22 (m, 1H), 4.00-3.92 (m, 1H), 3.66-3.52 (m, 2H), 2.60-2.50 (m, 1H), 1.66-1.50 (m, 1H), 1.48-1.17 (m, 3H), 0.81-0.70 (m, 2H).

Example 4

(rac)trans-3-amino-4-(3-boronopropyl)-1-(N-(pyridin-2-yl)sulfamoyl)pyrrolidine-3-carboxylic Acid compound with 2,2,2-trifluoroacetic Acid (1:2)

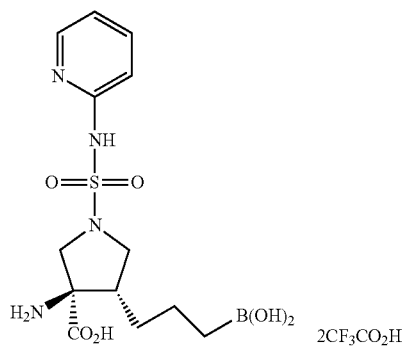

Step 1
2-oxo-N-(pyridin-2-yl)oxazolidine-3-sulfonamide

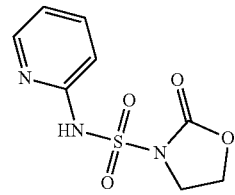 [SMILES: O=C1OCCN1S(=O)(=O)Nc1ccccn1]

In a glass vial-1, to a solution of sulfurisocyanatidic chloride (2.506 g, 17.708 mmol) in DCM (10 mL) was added 2-bromoethan-1-ol (2.213 g, 17.708 mmol) at 0° C. and stirred for 1 h. Simultaneously in glass vial-2, to a solution of pyridin-2-amine (2.000 g, 21.249 mmol) in DCM (10 mL) was added TEA (3.584 g, 35.416 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (50 mL) and extracted with DCM (2×50 mL). The combined organic phased was dried over anhydrous $Na_2SO_4$ and concentrated and purified by silica gel flash chromatography (EA:PE=0-100%) to give 0.3 g of the title compound. Yield: 6%. MS (ESI, m/e): 244 [M+1]$^+$.

Step 2 (rac)benzyl trans-4-allyl-3-azido-1-(N-(pyridin-2-yl)sulfamoyl)pyrrolidine-3-carboxylate

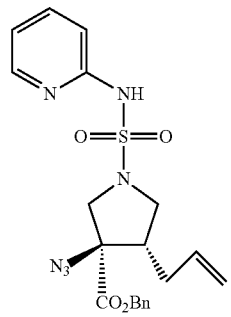 [SMILES: C=CC[C@H]1CN(S(=O)(=O)Nc2ccccn2)C[C@@]1(N=[N+]=[N-])C(=O)OCc1ccccc1]

To a solution of (rac) benzyl trans-4-allyl-3-azidopyrrolidine-3-carboxylate (0.110 g, 0.384 mmol) in MeCN (2 mL) was added TEA (0.155 g, 1.536 mmol) at r.t. The reaction mixture was stirred at r.t. for 15 min and then treated with 2-oxo-N-(pyridin-2-yl)oxazolidine-3-sulfonamide (0.280 g, 1.151 mmol). The reaction mixture was heated at 70° C. for 2 h. The resulting reaction mixture was poured into water and extracted with EA. The combined organic phase was dried over $Na_2SO_4$, concentrated and purified by silica gel flash chromatography (EA:PE=0 to 40%) to give 0.08 g of the title compound. Yield: 47%. MS (ESI, m/e): 443 [M+1]$^+$.

Step 3 (rac)benzyl trans-3-azido-1-(N-(pyridin-2-yl)sulfamoyl)-4-(3-(4,4,5,5-tetramethyl-1,3,2-dioxaborolan-2-yl)propyl)pyrrolidine-3-carboxylate

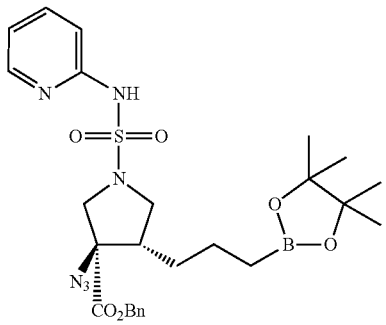 [SMILES: CC1(C)OB(CCC[C@H]2CN(S(=O)(=O)Nc3ccccn3)C[C@@]2(N=[N+]=[N-])C(=O)OCc2ccccc2)OC1(C)C]

A solution of the product of step 2 (0.08 g, 0.181 mmol), bis (1,5-cyclootadiene) diiridium dichloride (0.024 g, 0.036 mmol) and 1,2-bis (diphenyphosphino) enthane (0.029 g, 0.072 mmol) in DCM (2 mL) was stirred for 30 min under $N_2$ atmosphere. Then, the solution of 4,4,5,5-tetramethy [1,3,2]dioxaborolane (0.116 g, 0.905 mmol) in DCM (2 mL) was added dropwise at 0° C. The reaction was allowed to warm to r.t. and stirred overnight, then, concentrated and purified by silica gel flash chromatography (EA:PE=0 to 40%) to give 0.07 g of the title compound. Yield: 70%. MS (ESI, m/e): 571 [M+1]$^+$.

Step 4 (rac)trans-3-amino-1-(N-(pyridin-2-yl)sulfamoyl)-4-(3-(4,4,5,5-tetramethyl-1,3,2-dioxaborolan-2-yl)propyl)pyrrolidine-3-carboxylic Acid

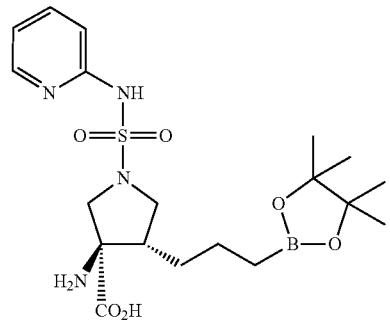 [SMILES: CC1(C)OB(CCC[C@H]2CN(S(=O)(=O)Nc3ccccn3)C[C@@]2(N)C(=O)O)OC1(C)C]

The product of step 3 (0.07 g, 0.123 mmol) was dissolved in a 1:1 mixture of ethyl acetate and ethanol (4 mL). 10% Pd—C (10 mg) was added and the solution was degassed under vacuum and purged with $H_2$. The solution was stirred at $H_2$ atmosphere at r.t. overnight. The reaction mixture was filtered through a 4 syringe filter to remove traces of palladium and concentrated to dryness under vacuum and used without further purification. MS (ESI, m/e): 455[M+1]$^+$.

Step 5 (rac)trans-3-amino-4-(3-boronopropyl)-1-(N-(pyridin-2-yl)sulfamoyl)pyrrolidine-3-carboxylic Acid Compound with 2,2,2-trifluoroacetic Acid (1:2)

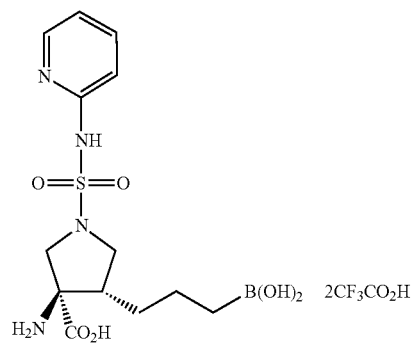 [SMILES: N[C@@]1(C(=O)O)CN(S(=O)(=O)Nc2ccccn2)C[C@@H]1CCCB(O)O ; "2CF3CO2H"]

A suspension of the product of step 4 in 4 N hydrochloric acid (2 mL) was stirred at 50° C. overnight and then cooled to r.t. The solution was concentrated under vacuum and purified by reverse phase HPLC to give 0.008 g of the title compound. Yield: 11% over 2 steps. MS (ESI, m/e): 355 [M-$H_2O$+1]$^+$.

$^1$HNMR Spectrum: (400 MHz, $D_2O$) δ 7.93-7.83 (m, 2H), 7.32 (d, J=9.2 Hz, 1H), 6.97 (t, J=5.6 Hz, 1H), 3.87 (d, J=11.2 Hz, 1H), 3.67 (t, J=7.6 Hz, 1H), 3.48 (d, J=11.2 Hz, 1H), 3.10 (t, J=7.6 Hz, 1H), 2.50-2.37 (m, 1H), 1.50-1.40 (m, 1H), 1.34-1.12 (m, 3H), 0.72-0.55 (m, 2H).

Example 5

(rac)trans-3-amino-1-(N-(2-aminoethyl)sulfamoyl)-4-(3-boronopropyl)pyrrolidine-3-carboxylic Acid Compound with 2,2,2-trifluoroacetic Acid (1:2)

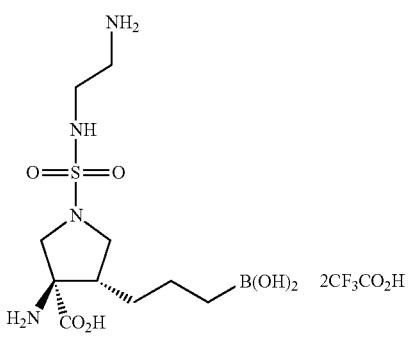 [SMILES: NCCNS(=O)(=O)N1C[C@H](CCCB(O)O)[C@](N)(C(=O)O)C1 ; "2CF3CO2H"]

Step 1 tert-butyl(2-((2-oxooxazolidine)-3-sulfonamido)ethyl)carbamate

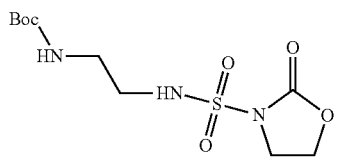

In a glass vial-1, to a solution of sulfurisocyanatidic chloride (0.736 g, 5.201 mmol) in DCM (5 mL) was added 2-bromoethan-1-ol (0.650 g, 5.201 mmol) at 0° C. and stirred for 1 h. Simultaneously in glass vial-2, to a solution of tert-butyl (2-aminoethyl)carbamate (1.000 g, 6.241 mmol) in DCM (5 mL) was added TEA (1.052 g, 10.402 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (25 mL) and extracted with DCM (2×25 mL). The combined organic phased was dried over anhydrous $Na_2SO_4$ and concentrated and purified by silica gel flash chromatography (EA:PE=0-60%) to give 0.324 g of the title compound. Yield: 17%. MS (ESI, m/e): 254 [M−56+1]$^+$.

Step 2 (rac)benzyl trans-4-allyl-3-azido-1-(N-(2-((tert-butoxycarbonyl)amino)ethyl)sulfamoyl) pyrrolidine-3-carboxylate

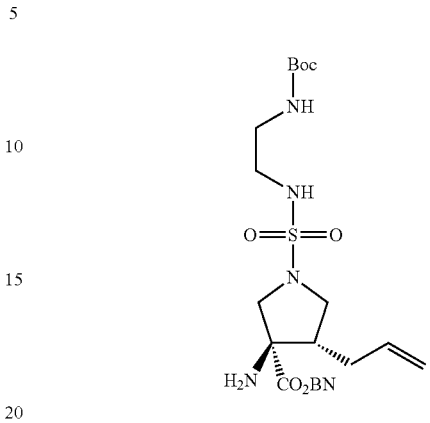

To a solution of (rac)benzyl trans-4-allyl-3-azidopyrrolidine-3-carboxylate (0.100 g, 0.349 mmol) in MeCN (3 mL) was added TEA (0.142 g, 1.396 mmol) at r.t. The reaction mixture was stirred at r.t. for 15 min and then treated with the product of Step 1 (0.324 g, 1.047 mmol). The reaction mixture was heated at 70° C. for 2 h. The resulting reaction mixture was poured into water and extracted with EA. The combined organic phase was dried over $Na_2SO_4$, concentrated and purified by silica gel flash chromatography (EA:PE=0 to 40%) to give 0.12 g of the title compound. Yield: 67%. MS (ESI, m/e): 453 [M−56+1]$^+$.

Step 3 (rac)benzyl trans-3-azido-1-(N-(2-((tert-butoxycarbonyl)amino)ethyl)sulfamoyl)-4-(3-(4,4,5,5-tetramethyl-1,3,2-dioxaborolan-2-yl)propyl)pyrrolidine-3-carboxylate

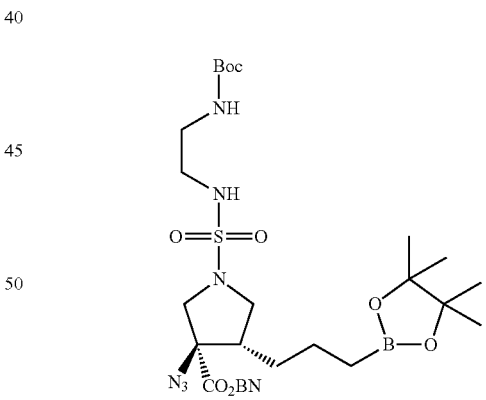

A solution of the product of step 2 (0.12 g, 0.236 mmol), bis (1,5-cyclootadiene) diiridium dichloride (0.032 g, 0.047 mmol) and 1,2-bis (diphenyphosphino) enthane (0.037 g, 0.094 mmol) in DCM (2 mL) was stirred for 30 min under $N_2$ atmosphere. Then, the solution of 4,4,5,5-tetramethy [1,3,2]dioxaborolane (0.151 g, 1.18 mmol) in DCM (2 mL) was added dropwise at 0° C. The reaction was allowed to warm to r.t. and stirred overnight, then, concentrated and purified by silica gel flash chromatography (EA:PE=0-40%) to give 0.09 g of the title compound as a yellow oil. Yield: 60%. MS (ESI, m/e): 636[M+1]$^+$.

Step 4 (rac)trans-3-amino-1-(N-(2-(((tert-butoxycarbonyl)amino)ethyl)sulfamoyl)-4-(3-(4,4,5,5-tetramethyl-1,3,2-dioxaborolan-2-yl)propyl)pyrrolidine-3-carboxylic Acid

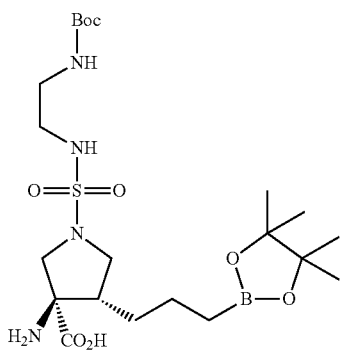 [SMILES: CC(C)(C)OC(=O)NCCNS(=O)(=O)N1C[C@H](CCCB2OC(C)(C)C(C)(C)O2)[C@](N)(C(=O)O)C1]

The product of step 3 (0.09 g, 0.141 mmol) was dissolved in a 1:1 mixture of ethyl acetate and ethanol (4 mL). 10% Pd—C (10 mg) was added and the reaction mixture was degassed under vacuum and purged with $H_2$. The solution was stirred at $H_2$ atmosphere at r.t. for overnight. The reaction mixture was filtered through a 4 syringe filter to remove traces of palladium and concentrated to dryness under vacuum and used without further purification.

MS (ESI, m/e): 520[M+1]$^+$.

Step 5 (rac)trans-3-amino-1-(N-(2-aminoethyl)sulfamoyl)-4-(3-boronopropyl)pyrrolidine-3-carboxylic Acid (1:2), 2,2,2-trifluoroacetic Acid Salt

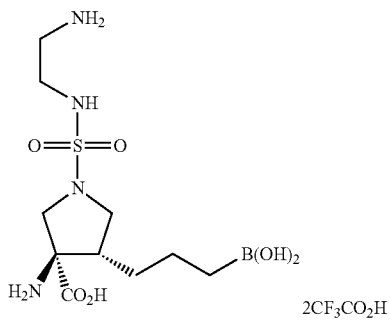 [SMILES: NCCNS(=O)(=O)N1C[C@H](CCCB(O)O)[C@](N)(C(=O)O)C1]

A suspension of the product of step 4 (from the previous step) in 4 N hydrochloric acid (2 mL) was stirred at 50° C. overnight and then cooled to r.t. The solution was concentrated under vacuum and purified by reverse phase HPLC to give 0.008 g of the title compound. Yield: 10% over 2 steps. MS (ESI, m/e): 321 [M−18+1]$^+$.

$^1$HNMR Spectrum: (400 MHz, $D_2O$) δ 3.94 (d, J=11.2 Hz, 1H), 3.75 (t, J=7.6 Hz, 1H), 3.53 (d, J=11.2 Hz, 1H), 3.39 (t, J=7.6 Hz, 2H), 3.17 (t, J=11.2 Hz, 1H), 3.10 (t, J=7.6 Hz, 2H), 2.59-2.49 (m, 1H), 1.60-1.50 (m, 1H), 1.44-1.18 (m, 3H), 0.80-0.65 (m, 2H).

Example 6

(rac)trans-1-(N-(1H-pyrazol-3-yl)sulfamoyl)-3-amino-4-(3-boronopropyl)pyrrolidine-3-carboxylic Acid, (1:2) 2,2,2-trifluoroacetic Acid Salt

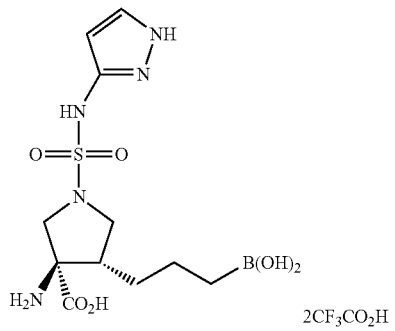 [SMILES: N[C@@]1(C(=O)O)CN(S(=O)(=O)Nc2cc[nH]n2)C[C@@H]1CCCB(O)O]

Step 1 3-nitro-1-((2-(trimethylsilyl)ethoxy)methyl)-1H-pyrazole

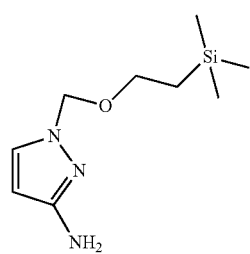

Sodium hydride (0.425 g of a 60% dispersion in mineral oil, 10.612 mmol) was added to a solution of 3-nitro-1H-pyrazole (1.000 g, 8.843 mmol) in 40 mL of THF at 0° C. and the mixture was stirred for 10 min. SEM-Cl (1.72 mL, 9.727 mmol) was added dropwise and the mixture was stirred at r.t. for 1 h. The reaction mixture was diluted ethyl acetate and washed with brine. The organic phase was dried over $Na_2SO_4$, concentrated and purified by silica gel flash chromatography (EA:PE=0 to 40%) to give 1.8 g of the title compound. Yield: 86%. MS (ESI, m/e): 244 [M+1]$^+$.

Step 2 1-((2-(trimethylsilyl)ethoxy)methyl)-1H-pyrazol-3-amine

Palladium on carbon (10%, 0.22 g) was added to a solution of the product of step 1 (1.8 g) in 20 mL of EA and the resulting suspension was stirred under H₂ for 2 h. The mixture was filtered through a pad of celite and the filtrate was concentrated under vacuum to give 1.5 g of the title compound. Yield: 95%. MS (ESI, m/e): 214 [M+1]⁺.

Step 3 2-oxo-N-(1-((2-(trimethylsilyl)ethoxy)methyl)-1H-pyrazol-3-yl)oxazolidine-3-sulfonamide

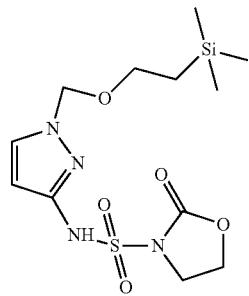 [SMILES: C[Si](C)(C)CCOCn1ccc(NS(=O)(=O)N2CCOC2=O)n1]

In a glass vial-1, to a solution of sulfurisocyanatidic chloride (0.829 g, 5.858 mmol) in DCM (10 mL) was added 2-bromoethan-1-ol (0.732 g, 5.858 mmol) at 0° C. and stirred for 1 h. Simultaneously in glass vial-2, to a solution of the product of step 2 (1.5 g, 7.03 mmol) in DCM (10 mL) was added TEA (1.186 g, 11.716 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (25 mL) and extracted with DCM (2×25 mL). The combined organic phased was dried over anhydrous Na₂SO₄ and concentrated and purified by silica gel flash chromatography (MeOH: DCM=0 to 10%) to give 0.6 g of the title compound. Yield: 24%. MS (ESI, m/e): 363 [M+1]⁺.

Step 4 (rac)benzyl trans-4-allyl-3-azido-1-(N-(1-((2-(trimethylsilyl)ethoxy)methyl)-1H-pyrazol-3-yl)sulfamoyl)pyrrolidine-3-carboxylate

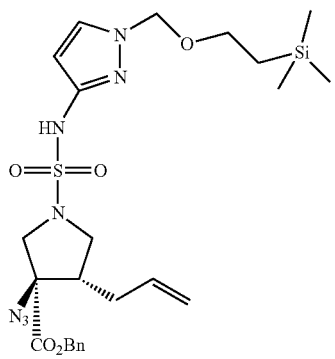 [SMILES: C=CC[C@H]1CN(S(=O)(=O)Nc2ccn(COCC[Si](C)(C)C)n2)C[C@@]1(N=[N+]=[N-])C(=O)OCc1ccccc1]

To a solution of (rac)benzyl trans-4-allyl-3-azidopyrrolidine-3-carboxylate (0.158 g, 0.552 mmol) in MeCN (5 mL) was added TEA (0.223 g, 2.208 mmol) at r.t. The reaction mixture was stirred at r.t. for 15 min and then treated with the product of step 3 (0.6 g, 1.655 mmol). The reaction mixture was heated at 70° C. overnight. The resulting reaction mixture was poured into water and extracted with EA. The combined organic phase was dried over Na₂SO₄, concentrated and purified by silica gel flash chromatography (EA:PE=0 to 40%) to give 0.1 g of the title compound. Yield: 32%. MS (ESI, m/e): 562 [M+1]⁺.

Step 5 (rac)benzyl trans-3-azido-4-(3-(4,4,5,5-tetramethyl-1,3,2-dioxaborolan-2-yl)propyl)-1-(N-(1-((2-(trimethylsilyl)ethoxy)methyl)-1H-pyrazol-3-yl)sulfamoyl)pyrrolidine-3-carboxylate

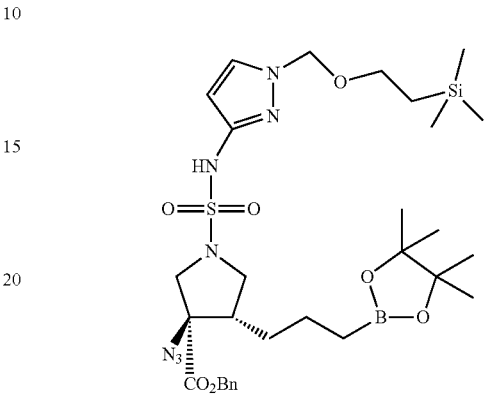

A solution of the product of step 4 (0.1 g, 0.178 mmol), bis (1,5-cyclootadiene) diiridium dichloride (0.024 g, 0.036 mmol) and 1,2-bis (diphenyphosphino) enthane (0.028 g, 0.071 mmol) in DCM (2 mL) was stirred for 30 min under N₂ atmosphere. Then, the solution of 4,4,5,5-tetramethy [1,3,2]dioxaborolane (0.114 g, 0.89 mmol) in DCM (2 mL) was added dropwise at 0° C. The reaction was allowed to warm to r.t. and stirred overnight, then, concentrated and purified by silica gel flash chromatography (EA:PE=20 to 40%) to give 0.1 g of the title compound as a yellow oil. Yield: 83%. MS (ESI, m/e): 690[M+1]⁺.

Step 6 (rac)trans-3-amino-4-(3-(4,4,5,5-tetramethyl-1,3,2-dioxaborolan-2-yl)propyl)-1-(N-(1-((2-(trimethylsilyl)ethoxy)methyl)-1H-pyrazol-3-yl)sulfamoyl)pyrrolidine-3-carboxylic Acid

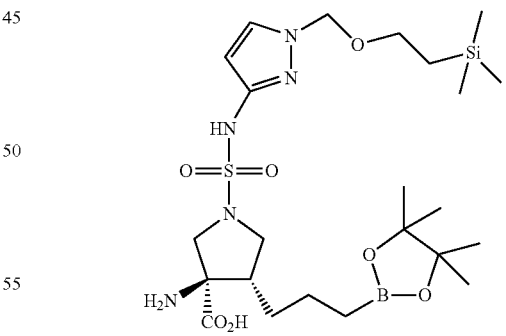

The product of step 5 (0.1 g, 0.145 mmol) was dissolved in a 1:1 mixture of ethyl acetate and ethanol (4 mL). 10% Pd—C (10 mg) was added and the solution was degassed under vacuum and purged with H₂. The solution was stirred at H₂ atmosphere at r.t. for overnight. The reaction mixture was filtered through a 4 syringe filter to remove traces of palladium and concentrated to dryness under vacuum and used without further purification. MS (ESI, m/e): 574[M+1]⁺.

Step 7 (rac)trans-1-(N-(1H-pyrazol-3-yl)sulfamoyl)-3-amino-4-(3-boronopropyl)pyrrolidine-3-carboxylic Acid (1:2), 2,2,2-trifluoroacetic Acid Salt

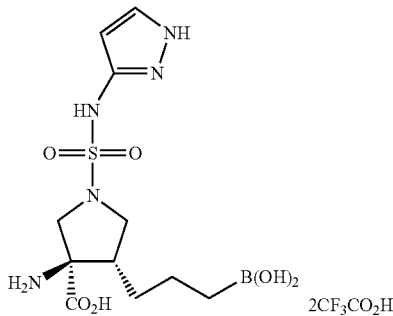 [SMILES: N[C@@]1(C(=O)O)CN(S(=O)(=O)Nc2cc[nH]n2)C[C@@H]1CCCB(O)O]

A suspension of the product of step 6 in 4 N hydrochloric acid (2 mL) was stirred at 50° C. for 6 hours and then cooled to r.t. The solution was concentrated under vacuum and purified by reverse phase HPLC to give 0.007 g of the title compound. Yield: 8% over 2 steps. MS (ESI, m/e): 344 [M-H$_2$O+1]$^+$.

$^1$HNMR Spectrum: (400 MHz, D$_2$O) δ 7.67 (s, 1H), 6.23 (s, 1H), 3.98 (d, J=7.2 Hz, 1H), 3.78 (t, J=9.2 Hz, 1H), 3.60 (d, J=7.2 Hz, 1H), 3.20 (t, J=9.2 Hz, 1H), 2.55-2.44 (m, 1H), 1.56-1.46 (m, 1H), 1.41-1.20 (m, 3H), 0.79-0.62 (m, 2H).

Example 7

(rac)trans-3-amino-1-(N-(2-amino-2-oxoethyl)sulfamoyl)-4-(3-boronopropyl)pyrrolidine-3-carboxylic Acid, (1:1) 2,2,2-trifluoroacetic Acid Salt

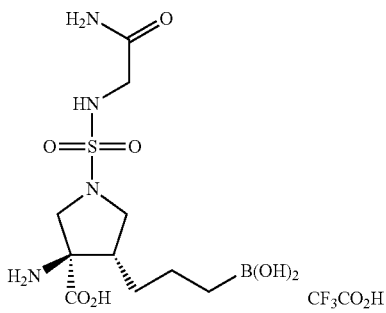 [SMILES: NC(=O)CNS(=O)(=O)N1C[C@H](CCCB(O)O)[C@](N)(C(=O)O)C1 ; "CF3CO2H"]

Step 1
2-((2-oxooxazolidine)-3-sulfonamido)acetamide

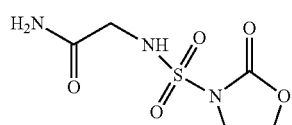

In a glass vial-1, to a solution of sulfurisocyanatidic chloride (1.067 g, 7.538 mmol) in DCM (10 mL) was added 2-bromoethan-1-ol (0.942 g, 7.538 mmol) at 0° C. and stirred for 1 h. Simultaneously in glass vial-2, to a solution of 2-aminoacetamide hydrochloride (1.000 g, 9.046 mmol) in DCM (10 mL) was added TEA (2.288 g, 22.614 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (25 mL) and extracted with DCM (2×25 mL). The combined organic phased was dried over anhydrous Na$_2$SO$_4$ and concentrated and purified by silica gel flash chromatography (MeOH:DCM=0 to 10%) to give 0.16 g of the title compound. Yield: 8%. MS (ESI, m/e): 224 [M+1]$^+$.

Step 2 (rac)trans-3-amino-1-(N-(2-amino-2-oxoethyl)sulfamoyl)-4-(3-boronopropyl)pyrrolidine-3-carboxylic Acid Compound with 2,2,2-trifluoroacetic Acid (1:1)

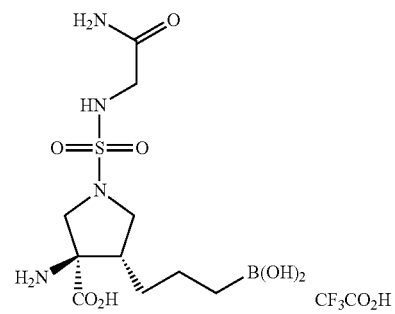 [SMILES: NC(=O)CNS(=O)(=O)N1C[C@H](CCCB(O)O)[C@](N)(C(=O)O)C1 ; "CF3CO2H"]

Starting with the product of Step 1 and (rac)benzyl trans-4-allyl-3-azidopyrrolidine-3-carboxylate, the title compound was prepared by using the same procedures described in Step 2 to Step 5 of Example 6. MS (ESI, m/e): 335 [M-H$_2$O+1]$^+$.

$^1$HNMR Spectrum: (400 MHz, D$_2$O) δ 3.90-3.84 (m, 3H), 3.72 (t, J=7.6 Hz, 1H), 3.51 (d, J=11.2 Hz, 1H), 3.16-3.08 (m, 1H), 2.51-2.41 (m, 1H), 1.56-1.46 (m, 1H), 1.42-1.17 (m, 3H), 0.77-0.67 (m, 2H).

Example 8

(rac)trans-3-amino-4-(3-boronopropyl)-1-(N-glycylsulfamoyl)pyrrolidine-3-carboxylic acid, (1:2) 2,2,2-trifluoroacetic Acid Salt

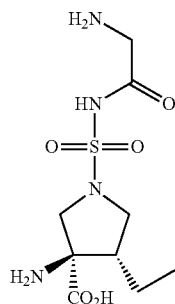

Step 1 (rac)benzyl trans-4-allyl-3-azido-1-(N-((tert-butoxycarbonyl)glycyl)sulfamoyl)pyrrolidine-3-carboxylate

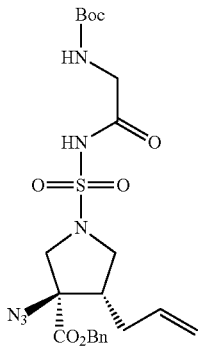 [SMILES: C=CC[C@H]1CN(S(=O)(=O)NC(=O)CNC(=O)OC(C)(C)C)C[C@@]1(N=[N+]=[N-])C(=O)OCc1ccccc1]

The tert-butoxycarbonyl glycine (0.144 g, 0.82 mmol) was dissolved in dichloroethane (2 mL) and CDI (0.2 g, 1.230 mmol) was added to the solution. The mixture was stirred for 1.5 hours at 50° C. The solution was then cooled down to ambient temperature and the product of step 1 of Example 2 (0.15 g, 0.410 mmol) and DBU (0.312 g, 2.050 mmol) were then added. The mixture was stirred at 50° C. overnight and concentrated, purified by silica gel flash chromatography (EA:PE=0 to 50%) to give 0.08 g of the title compound. Yield: 36%. MS (ESI, m/e): 423[M−100+1]$^+$.

Step 2 (rac)benzyl trans-3-azido-1-(N-((tert-butoxycarbonyl)glycyl)sulfamoyl)-4-(3-(4,4,5,5-tetramethyl-1,3,2-dioxaborolan-2-yl)propyl)pyrrolidine-3-carboxylate

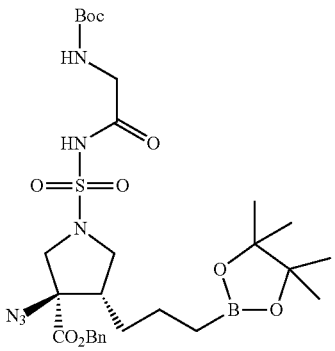 [SMILES: CC(C)(C)OC(=O)NCC(=O)NS(=O)(=O)N1C[C@H](CCCB2OC(C)(C)C(C)(C)O2)[C@](N=[N+]=[N-])(C(=O)OCc2ccccc2)C1]

The title compound was prepared by using the same procedure described in Step 3 of Example 5. MS (ESI, m/e): 551[M−100+1]$^+$.

Step 3 (rac)trans-3-amino-1-(N-((tert-butoxycarbonyl)glycyl)sulfamoyl)-4-(3-(4,4,5,5-tetramethyl-1,3,2-dioxaborolan-2-yl)propyl)pyrrolidine-3-carboxylic Acid

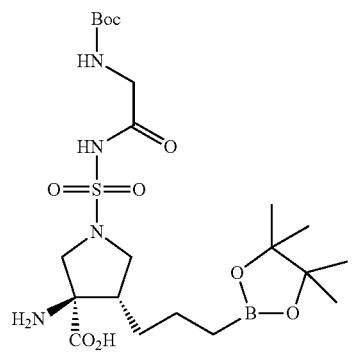 [SMILES: CC(C)(C)OC(=O)NCC(=O)NS(=O)(=O)N1C[C@H](CCCB2OC(C)(C)C(C)(C)O2)[C@](N)(C(=O)O)C1]

The title compound was prepared by using the same procedure described in Step 4 of Example 5. MS (ESI, m/e): 535[M+1]$^+$.

Step 4 (rac)trans-3-amino-4-(3-boronopropyl)-1-(N-glycylsulfamoyl)pyrrolidine-3-carboxylic Acid, (1:2) 2,2,2-trifluoroacetic Acid Salt

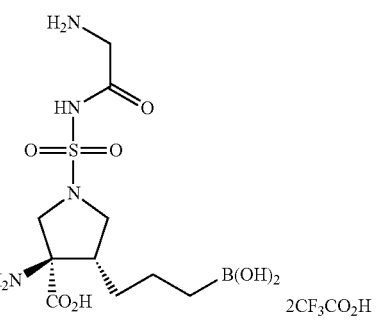

The title compound was prepared by using the same procedure described in Step 5 of Example 5. MS (ESI, m/e): 335 [M−H$_2$O+1]$^+$.

$^1$HNMR Spectrum: (400 MHz, D$_2$O) δ 4.06 (d, J=11.2 Hz, 1H), 3.88 (s, 2H), 3.88-3.80 (m, 1H), 3.60 (d, J=11.2 Hz, 1H), 3.31 (t, J=7.6 Hz, 1H), 2.56-2.46 (m, 1H), 1.57-1.47 (m, 1H), 1.42-1.22 (m, 3H), 0.80-0.62 (m, 2H).

Example 9

(rac)trans-3-amino-4-(3-boronopropyl)-1-(N-(2-hydroxy-2-methylpropyl)sulfamoyl)pyrrolidine-3-carboxylic Acid, (1:1) 2,2,2-trifluoroacetic Acid Salt

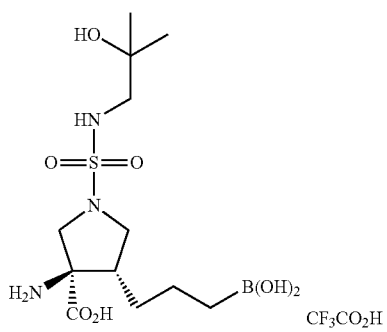 [SMILES: CC(C)(O)CNS(=O)(=O)N1C[C@H](CCCB(O)O)[C@](N)(C(=O)O)C1 ; "CF3CO2H"]

Step 1 N-(2-hydroxy-2-methylpropyl)-2-oxooxazolidine-3-sulfonamide

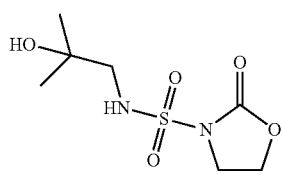

In a glass vial-1, to a solution of sulfurisocyanatidic chloride (0.662 g, 4.675 mmol) in DCM (5 mL) was added 2-bromoethan-1-ol (0.584 g, 4.675 mmol) at 0° C. and stirred for 1 h. Simultaneously in glass vial-2, to a solution of 1-amino-2-methylpropan-2-ol (0.5 g, 5.61 mmol) in DCM (5 mL) was added TEA (0.946 g, 9.35 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (25 mL) and extracted with DCM (2×25 mL). The combined organic phased was dried over anhydrous $Na_2SO_4$ and concentrated and purified by silica gel flash chromatography (EA:PE=0 to 60%) to give 0.3 g of the title compound. Yield: 22%. MS (ESI, m/e): 239 $[M+1]^+$.

Step 2 (rac)benzyl trans-4-allyl-3-azido-1-(N-(2-hydroxy-2-methylpropyl)sulfamoyl)pyrrolidine-3-carboxylate

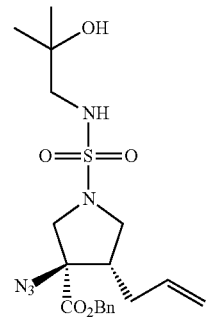 [SMILES: C=CC[C@H]1CN(S(=O)(=O)NCC(C)(C)O)C[C@@]1(N=[N+]=[N-])C(=O)OCc1ccccc1]

To a solution of (rac)benzyl trans-4-allyl-3-azidopyrrolidine-3-carboxylate (0.240 g, 0.840 mmol) in MeCN (3 mL) was added TEA (0.34 g, 3.36 mmol) at r.t. The reaction mixture was stirred at r.t. for 15 min and then treated with the product of step 1 (0.300 g, 1.260 mmol). The reaction mixture was heated at 70° C. overnight. The resulting reaction mixture was poured into water and extracted with EA. The combined organic phase was dried over $Na_2SO_4$, concentrated and purified by silica gel flash chromatography (MeOH:DCM=0 to 10%) to give 0.1 g of the title compound. Yield: 27%. MS (ESI, m/e): 438 $[M+1]^+$.

Step 3 (rac)benzyl trans-3-azido-1-(N-(2-hydroxy-2-methylpropyl)sulfamoyl)-4-(3-(4,4,5,5-tetramethyl-1,3,2-dioxaborolan-2-yl)propyl)pyrrolidine-3-carboxylate

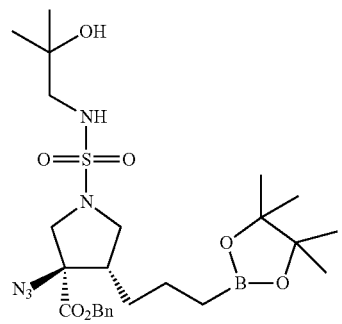 [SMILES: CC(C)(O)CNS(=O)(=O)N1C[C@H](CCCB2OC(C)(C)C(C)(C)O2)[C@](N=[N+]=[N-])(C(=O)OCc2ccccc2)C1]

Starting with the product of Step 2, the title compound was prepared by using the same procedure described in Step 3 of Example 5. MS (ESI, m/e): 566$[M+1]^+$.

Step 4 (rac)trans-3-amino-1-(N-(2-hydroxy-2-methylpropyl)sulfamoyl)-4-(3-(4,4,5,5-tetramethyl-1,3,2-dioxaborolan-2-yl)propyl)pyrrolidine-3-carboxylic Acid

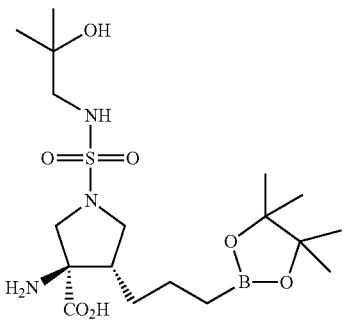 [SMILES: CC(C)(O)CNS(=O)(=O)N1C[C@H](CCCB2OC(C)(C)C(C)(C)O2)[C@](N)(C(=O)O)C1]

Starting with the product of Step 3, the title compound was prepared by using the same procedure described in Step 4 of Example 5. MS (ESI, m/e): 450[M+1]$^+$.

Step 5 (rac)trans-3-amino-4-(3-boronopropyl)-1-(N-(2-hydroxy-2-methylpropyl)sulfamoyl) pyrrolidine-3-carboxylic Acid, (1:1) 2,2,2-trifluoroacetic Acid Salt

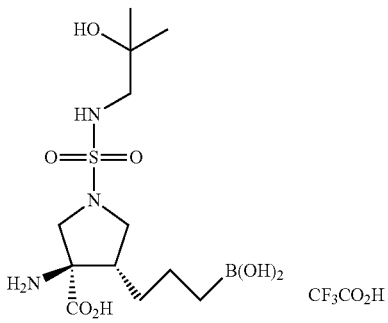 [SMILES: CC(C)(O)CNS(=O)(=O)N1C[C@H](CCCB(O)O)[C@](N)(C(=O)O)C1 ; "CF3CO2H"]

Starting with the product of Step 4, the title compound was prepared by using the same procedure described in Step 5 of Example 5. MS (ESI, m/e): 350 [M-H$_2$O+1]$^+$.

$^1$HNMR Spectrum: (400 MHz, D$_2$O) δ 3.84 (d, J=11.6 Hz, 1H), 3.68 (t, J=8.0 Hz, 1H), 3.47 (d, J=11.6 Hz, 1H), 3.11 (t, J=11.2 Hz, 1H), 3.02 (s, 2H), 2.47-2.38 (m, 1H), 1.54-1.44 (m, 1H), 1.38-1.16 (m, 3H), 0.96 (s, 6H), 0.74-0.64 (m, 2H).

Example 10

(rac)trans-3-amino-4-(3-boronopropyl)-1-(N-(2-hydroxyethyl)sulfamoyl)pyrrolidine-3-carboxylic Acid (1:1), 2,2,2-trifluoroacetic Acid Salt

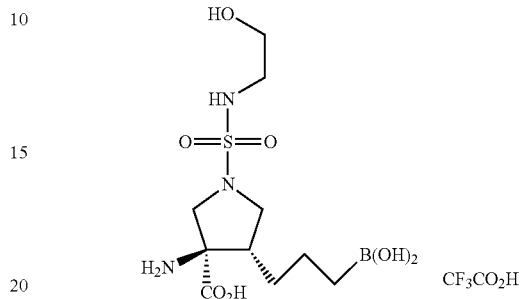

Step 1 N-(2-(benzyloxy)ethyl)-2-oxooxazolidine-3-sulfonamide

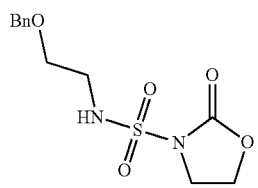

In a glass vial-1, to a solution of sulfurisocyanatidic chloride (0.628 g, 4.44 mmol) in DCM (5 mL) was added 2-bromoethan-1-ol (0.555 g, 4.44 mmol) at 0° C. and stirred for 1 h. Simultaneously in glass vial-2, to a solution of 2-(benzyloxy)ethan-1-amine hydrochloride (1.000 g, 5.33 mmol) in DCM (5 mL) was added TEA (1.57 g, 15.54 mmol) at 0° C. and stirred for 1 h. After 1 h, the reaction mixture of vial-2 was added to the reaction mixture in vial-1 at 0° C. The resulting reaction mixture was stirred at r.t. for 2 h. The resulting reaction mixture was poured into water (25 mL) and extracted with DCM (2×50 mL). The combined organic phased was dried over anhydrous Na$_2$SO$_4$ and concentrated and purified by silica gel flash chromatography (EA:PE=0 to 60%) to give 0.315 g of the title compound. Yield: 20%. MS (ESI, m/e): 301 [M+1]$^+$.

Step 2 (rac)benzyl trans-4-allyl-3-azido-1-(N-(2-(benzyloxy)ethyl)sulfamoyl)pyrrolidine-3-carboxylate

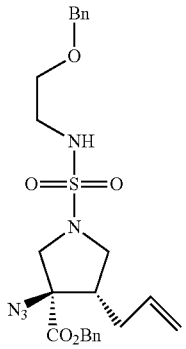 [SMILES: C=CC[C@H]1CN(S(=O)(=O)NCCOCc2ccccc2)C[C@@]1(N=[N+]=[N-])C(=O)OCc1ccccc1]

To a solution of (rac)benzyl trans-4-allyl-3-azidopyrrolidine-3-carboxylate (0.15 g, 0.524 mmol) in MeCN (3 mL) was added TEA (0.212 g, 2.096 mmol) at r.t. The reaction mixture was stirred at r.t. for 15 min and then treated with the product of step 1 (0.315 g, 1.048 mmol). The reaction mixture was heated at 70° C. overnight. The resulting reaction mixture was poured into water and extracted with EA. The combined organic phase was dried over $Na_2SO_4$, concentrated and purified by silica gel flash chromatography (MeOH:DCM=0 to 10%) to give 0.1 g of the title compound. Yield: 38%. MS (ESI, m/e): 500[M+1]$^+$.

Step 3 (rac)benzyl trans-3-azido-1-(N-(2-(benzyloxy)ethyl)sulfamoyl)-4-(3-(4,4,5,5-tetramethyl-1,3,2-dioxaborolan-2-yl)propyl)pyrrolidine-3-carboxylate

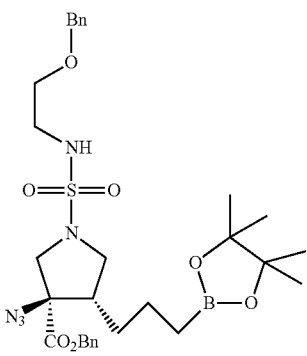 [SMILES: CC1(C)OB(CCC[C@H]2CN(S(=O)(=O)NCCOCc3ccccc3)C[C@@]2(N=[N+]=[N-])C(=O)OCc2ccccc2)OC1(C)C]

Starting with the product of Step 2, the title compound was prepared by using the same procedure described in Step 3 of Example 5. MS (ESI, m/e): 628[M+1]$^+$.

Step 4 (rac)trans-3-amino-1-(N-(2-hydroxyethyl)sulfamoyl)-4-(3-(4,4,5,5-tetramethyl-1,3,2-dioxaborolan-2-yl)propyl)pyrrolidine-3-carboxylic Acid

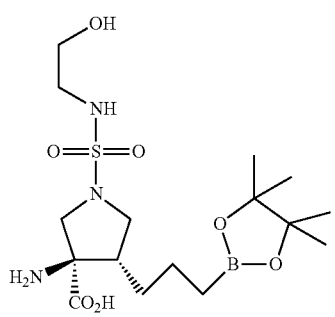 [SMILES: CC1(C)OB(CCC[C@H]2CN(S(=O)(=O)NCCO)C[C@@]2(N)C(=O)O)OC1(C)C]

Starting with the product of Step 3, the title compound was prepared by using the same procedure described in Step 4 of Example 5. MS (ESI, m/e): 422[M+1]$^+$.

Step 5 (rac)trans-3-amino-4-(3-boronopropyl)-1-(N-(2-hydroxyethyl)sulfamoyl)pyrrolidine-3-carboxylic Acid, (1:1) 2,2,2-trifluoroacetic Acid Salt

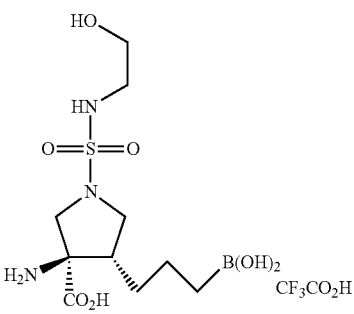 [SMILES: N[C@@]1(C(=O)O)CN(S(=O)(=O)NCCO)C[C@@H]1CCCB(O)O ; "CF3CO2H"]

Starting with the product of Step 4, the title compound was prepared by using the same procedure described in Step 5 of Example 5. MS (ESI, m/e): 322 [M-$H_2O$+1]$^+$.

$^1$HNMR Spectrum: (400 MHz, $D_2O$) δ 3.87 (d, J=12.4 Hz, 1H), 3.71 (t, J=8.0 Hz, 1H), 3.59 (t, J=6.0 Hz, 2H), 3.50 (d, J=12.4 Hz, 1H), 3.20-3.08 (m, 3H), 2.56-2.46 (m, 1H), 1.56-1.46 (m, 1H), 1.40-1.13 (m, 3H), 0.78-0.60 (m, 2H).

Example 11

(rac)trans-3-amino-4-(3-boronopropyl)-1-(N—((S)-1-carboxy-2-methylpropyl)sulfamoyl)pyrrolidine-3-carboxylic Acid (Diastereomer), (1:1) 2,2,2-trifluoroacetic Acid Salt

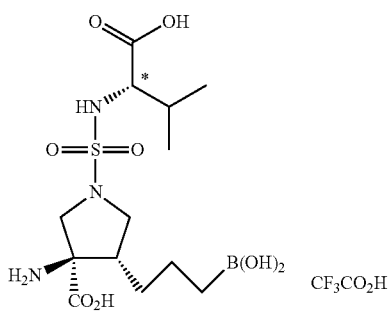 [SMILES: CC(C)[C@H](NS(=O)(=O)N1C[C@H](CCCB(O)O)[C@](N)(C(=O)O)C1)C(=O)O ; "CF3CO2H"]

Starting with tert-butyl L-valinate hydrochloride, the title compound was prepared by using the procedures described in Example 7. MS (ESI, m/e): 378 [M-H₂O+1]⁺.

¹HNMR Spectrum: (400 MHz, D₂O) δ 3.38 (dd, J=16.4, 11.2 Hz, 1H), 3.75-3.66 (m, 2H), 3.50 (dd, J=10.8, 6.8 Hz 1H), 3.15-3.03 (m, 1H), 2.47-2.37 (m, 1H), 2.08-1.96 (m, 1H), 1.54-1.45 (m, 1H), 1.43-1.18 (m, 3H), 0.94 (d, J=6.4 Hz, 3H), 0.90-0.86 (m, 3H), 0.76-0.64 (m, 2H).

Example 12

(rac)trans-3-amino-1-(N-(1-(aminomethyl)cyclopropyl)sulfamoyl)-4-(3-boronopropyl)pyrrolidine-3-carboxylic Acid, (1:2) 2,2,2-trifluoroacetic Acid Salt

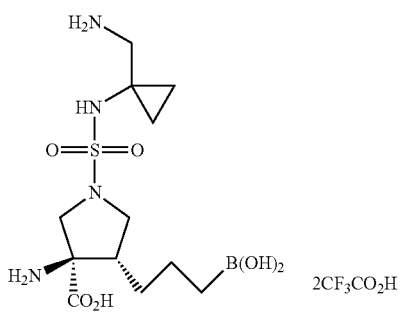 [SMILES: NCC1(NS(=O)(=O)N2C[C@H](CCCB(O)O)[C@](N)(C(=O)O)C2)CC1 ; "2CF3CO2H"]

Starting with tert-butyl ((1-aminocyclopropyl)methyl) carbamate and, the title compound was prepared by using the procedures described in Example 5. MS (ESI, m/e): 347 [M-H₂O+1]⁺.

¹HNMR Spectrum: (400 MHz, D₂O) δ 3.94-3.84 (m, 1H), 3.78-3.64 (m, 1H), 3.55-3.42 (m, 1H), 3.17-3.00 (m, 3H), 2.55-2.45 (m, 1H), 1.62-1.48 (m, 1H), 1.40-1.17 (m, 3H), 1.16-1.14 (m, 1H), 0.93-0.84 (m, 3H), 0.77-0.62 (m, 2H).

Example 13

(rac)trans-3-amino-1-(N-(2-aminophenyl)sulfamoyl)-4-(3-boronopropyl)pyrrolidine-3-carboxylic Acid, (1:2) 2,2,2-trifluoroacetic Acid Salt

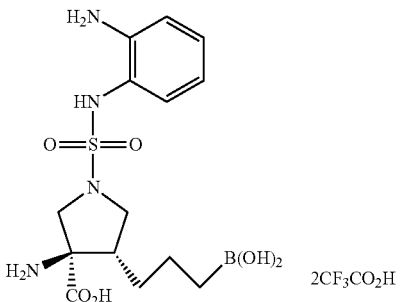

Starting with tert-butyl (2-aminophenyl)carbamate, the title compound was prepared by using the procedures described in Example 5. the title compound was prepared by using the procedures described in Example 6. MS (ESI, m/e): 369 [M-H₂O+1]⁺.

¹HNMR Spectrum: (400 MHz, D₂O) δ 7.53-7.50 (m, 1H), 7.46-7.41 (m, 2H), 7.40-7.37 (m, 1H), 3.92 (d, J=10.8 Hz, 1H), 3.63 (t, J=7.6 Hz, 1H), 3.51 (d, J=10.8 Hz, 1H), 3.10 (t, J=7.6 Hz, 1H), 2.45-2.35 (m, 1H), 1.52-1.42 (m, 1H), 1.33-1.10 (m, 3H), 0.71-0.61 (m, 2H).

Example 14

(rac)(3-(trans-4-amino-1-(N-(2-aminoethyl)sulfamoyl)-4-(ethoxycarbonyl)pyrrolidin-3-yl)propyl) boronic Acid, (1:2) 2,2,2-trifluoroacetic Acid Salt

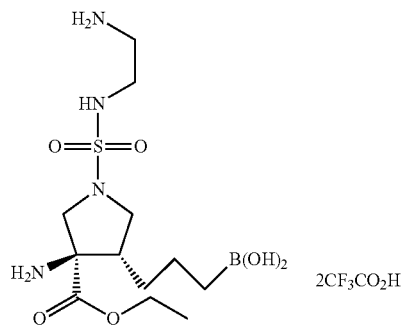 [SMILES: CCOC(=O)[C@]1(N)CN(S(=O)(=O)NCCN)C[C@@H]1CCCB(O)O ; "2CF3CO2H"]

Step 1 (rac)ethyl-trans-4-allyl-3-azido-1-(N-(2-((tert-butoxycarbonyl) amino) ethyl) sulfamoyl) pyrrolidine-3-carboxylate

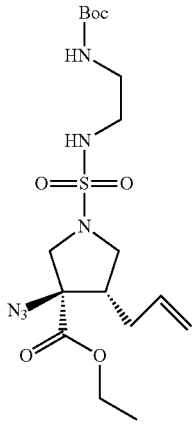 [SMILES: C=CC[C@H]1CN(S(=O)(=O)NCCNC(=O)OC(C)(C)C)C[C@@]1(N=[N+]=[N-])C(=O)OCC]

To a solution of (rac)-ethyl trans-4-allyl-3-azidopyrrolidine-3-carboxylate (0.400 g, 1.784 mmol) in MeCN (8 mL) was added TEA (1.083 g, 10.704 mmol) at r.t. The reaction mixture was stirred at r.t. for 15 min and then treated with the product of step 1 of Example 6 (1.104 g, 3.568 mmol). The reaction mixture was heated at 75° C. overnight. The resulting reaction mixture was poured into water and extracted with EA. The combined organic phase was dried over Na$_2$SO$_4$, concentrated and purified by silica gel flash chromatography (EA:PE=0 to 60%) to give 0.664 g of the title compound. Yield: 83%. MS (ESI, m/e): 347[M−100+1]$^+$.

Step 2 (rac)ethyl trans-3-azido-1-(N-(2-((tert-butoxycarbonyl)amino)ethyl)sulfamoyl)-4-(3-(4,4,5,5-tetramethyl-1,3,2-dioxaborolan-2-yl)propyl)pyrrolidine-3-carboxylate

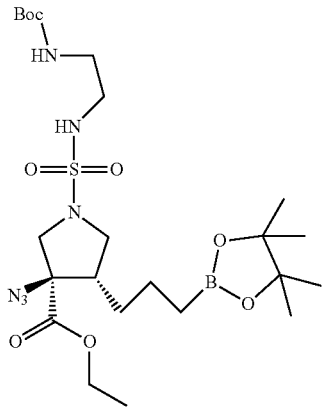 [SMILES: CCOC(=O)[C@]1(N=[N+]=[N-])CN(S(=O)(=O)NCCNC(=O)OC(C)(C)C)C[C@@H]1CCCB1OC(C)(C)C(C)(C)O1]

Starting with the product of Step 1, the title compound was prepared by using the same procedure described in Step 3 of Example 5. MS (ESI, m/e): 475[M−100+1]$^+$.

Step 3 (rac)ethyl trans-3-amino-1-(N-(2-((tert-butoxycarbonyl)amino)ethyl)sulfamoyl)-4-(3-(4,4,5,5-tetramethyl-1,3,2-dioxaborolan-2-yl)propyl)pyrrolidine-3-carboxylate

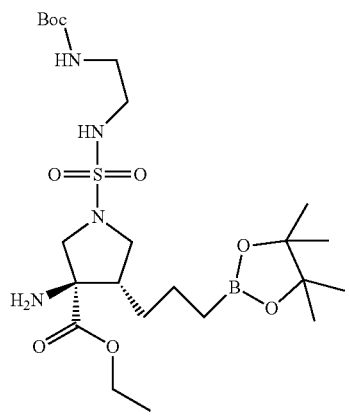 [SMILES: CCOC(=O)[C@]1(N)CN(S(=O)(=O)NCCNC(=O)OC(C)(C)C)C[C@@H]1CCCB1OC(C)(C)C(C)(C)O1]

Starting with the product of Step 2, the title compound was prepared by using the same procedure described in Step 4 of Example 5. MS (ESI, m/e): 549 [M+1]$^+$.

Step 4 (rac)(3-(trans-4-amino-1-(N-(2-aminoethyl)sulfamoyl)-4-(ethoxycarbonyl)pyrrolidin-3-yl)propyl)boronic Acid, (1:2) 2,2,2-trifluoroacetic Acid Salt

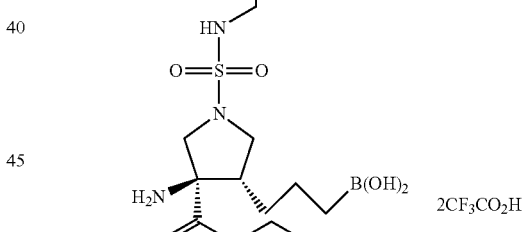

The product of step 3 (0.400 g, 0.730 mmol) was dissolved in a biphasic mixture of methanol (10 ml) and hexane (20 ml). The isobutylboronic acid (0.260 g, 2.555 mmol) and TFA (4 mL) was added. The reaction mixture was stirred vigorously at room temperature for 6 h. The methanol phase was separated and washed with hexane (3×20 ml), concentrated and purified by reverse phase HPLC to give the title compound. Yield: 25%. MS (ESI, m/e): 349 [M-H$_2$O+1]$^+$.

$^1$HNMR Spectrum: (400 MHz, D$_2$O) δ 4.37-4.27 (m, 2H), 3.95 (d, J=12 Hz, 1H), 3.77 (t, J=13.2 Hz, 1H), 3.53 (d, J=12 Hz, 1H), 3.70 (t, J=5.6 Hz, 2H), 3.16 (t, J=13.2 Hz, 1H), 3.10 (t, J=5.6 Hz, 2H), 2.68-2.59 (m, 1H), 1.59-1.49 (m, 1H), 1.40-1.26 (m, 3H), 1.26 (t, J=8.0 Hz, 3H), 0.80-0.63 (m, 2H).

Example 15

(3R,4S)-3-amino-1-(N-((rac)trans-2-aminocyclopropyl)sulfamoyl)-4-(3-boronopropyl)pyrrolidine-3-carboxylic Acid (Diastereomers), (1:2) 2,2,2-trifluoroacetic Acid Salt

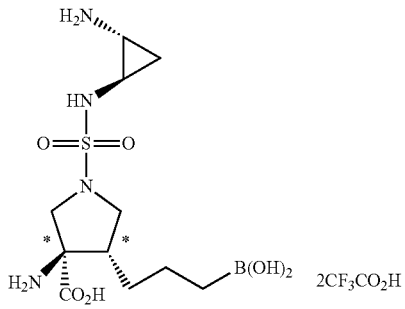 [SMILES: N[C@@H]1C[C@H]1NS(=O)(=O)N1C[C@H](CCCB(O)O)[C@](N)(C(=O)O)C1]

Step 1 (rac)tert-butyl (trans-2-((2-oxooxazolidine)-3-sulfonamido)cyclopropyl)carbamate

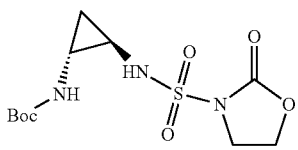 [SMILES: CC(C)(C)OC(=O)N[C@@H]1C[C@H]1NS(=O)(=O)N1CCOC1=O]

In a glass vial-1, to a solution of sulfurisocyanatidic chloride (0.206 g, 1.452 mmol) in DCM (2 mL) was added 2-bromoethan-1-ol (0.181 g, 1.452 mmol) at 0° C. and stirred for 1 h. Simultaneously in glass vial-2, to a solution of (rac) tert-butyl trans-2-aminocyclopropyl)carbamate (0.300 g, 1.742 mmol) in DCM (2 mL) was added TEA (0.440 g, 4.356 mmol) at 0° C. and stirred for 1 h. After 1 h, the reaction mixture of vial-2 was added to the reaction mixture in vial-1 at 0° C. The resulting reaction mixture was stirred at r.t. overnight. The resulting reaction mixture was poured into water (25 mL) and extracted with DCM (2×50 mL). The combined organic phased was dried over anhydrous $Na_2SO_4$ and concentrated and purified by silica gel flash chromatography (EA:PE=0-50%) to give 0.39 g of the title compound. Yield: 70%. MS (ESI, m/e): 222 [M−100+1]$^+$.

Step 2 (R)-1-phenylethyl (3R,4S)-4-allyl-3-azido-1-(N-((rac)trans-2-((tert-butoxycarbonyl)amino) cyclopropyl)sulfamoyl)pyrrolidine-3-carboxylate (diastereomers)

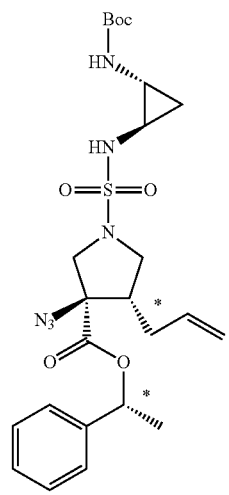 [SMILES: C=CC[C@H]1CN(S(=O)(=O)N[C@@H]2C[C@H]2NC(=O)OC(C)(C)C)C[C@@]1(N=[N+]=[N-])C(=O)O[C@H](C)c1ccccc1]

To a solution of (R)-1-phenylethyl (3S,4R)-4-allyl-3-azidopyrrolidine-3-carboxylate (0.350 g, 1.165 mmol) in MeCN (5 mL) was added TEA (0.707 g, 7 mmol) at r.t. The reaction mixture was stirred at r.t. for 15 min and then treated with the product of step 1 (0.39 g, 1.214 mmol). The reaction mixture was heated at 70° C. overnight. The resulting reaction mixture was poured into water and extracted with EA. The combined organic phase was dried over $Na_2SO_4$, concentrated and purified by silica gel flash chromatography (EA:PE=0 to 60%) to give 0.265 g of the title compound. Yield: 43%. MS (ESI, m/e): 435[M−100+1]$^+$.

Step 3 (R)-1-phenylethyl (3R,4S)-3-azido-1-(N-(rac)trans-2-((tert-butoxycarbonyl)amino) cyclopropyl)sulfamoyl)-4-(3-(4,4,5,5-tetramethyl-1,3,2-dioxaborolan-2-yl)propyl)pyrrolidine-3-carboxylate (Diastereomers)

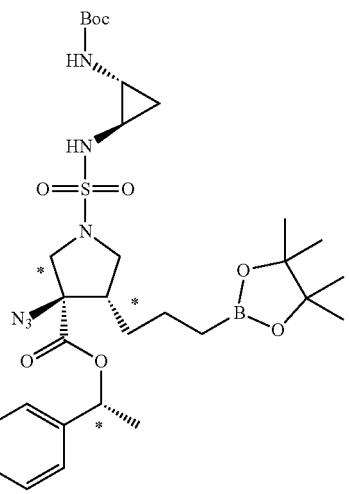

A solution of the product of step 2 ((0.265 g, 0.496 mmol), bis (1,5-cyclootadiene) diiridium dichloride (0.067 g, 0.1 mmol) and 1,2-bis (diphenyphosphino) enthane (0.080 g, 0.200 mmol) in DCM (2 mL) was stirred for 30 min under $N_2$ atmosphere. Then, the solution of 4,4,5,5-tetramethy [1,3,2]dioxaborolane (0.317 g, 2.48 mmol) in DCM (2 mL) was added dropwise at 0° C. The reaction was allowed to warm to r.t. and stirred overnight, then, concentrated and purified by silica gel flash chromatography (EA:PE=0 to 50%) to give 0.35 g of the title compound as a yellow oil. Yield: 93%. MS (ESI, m/e): 607[M−56+1]$^+$.

Step 4 (3R,4S)-3-amino-1-(N-((rac)trans-2-((tert-butoxycarbonyl)amino)cyclopropyl)sulfamoyl)-4-(3-(4,4,5,5-tetramethyl-1,3,2-dioxaborolan-2-yl)propyl)pyrrolidine-3-carboxylic Acid (Diastereomers)

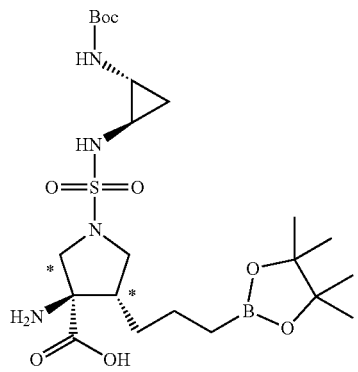 [SMILES: CC(C)(C)OC(=O)N[C@@H]1C[C@H]1NS(=O)(=O)N1C[C@H](CCCB2OC(C)(C)C(C)(C)O2)[C@](N)(C(=O)O)C1]

The product of step 3 (0.350 g, 0.528 mmol) was dissolved in a 1:1 mixture of ethyl acetate and ethanol (4 mL). 10% Pd—C(30 mg) was added and the reaction mixture was degassed under vacuum and purged with $H_2$. The solution was stirred at $H_2$ atmosphere at r.t. overnight. The solution was filtered through a 4 syringe filter to remove traces of palladium and concentrated to dryness under vacuum and used without further purification. MS (ESI, m/e): 533[M+1]$^+$.

Step 5 (3R,4S)-3-amino-1-(N-((rac)trans-2-aminocyclopropyl)sulfamoyl)-4-(3-boronopropyl) pyrrolidine-3-carboxylic Acid (Diastereomers), (1:2) 2,2,2-trifluoroacetic Acid Salt (Diastereomers)

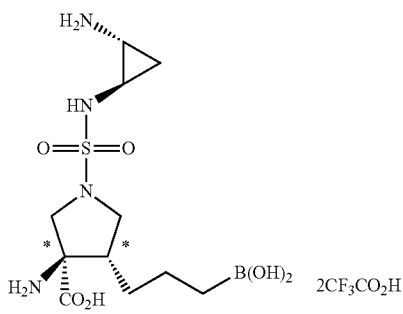 [SMILES: N[C@@H]1C[C@H]1NS(=O)(=O)N1C[C@H](CCCB(O)O)[C@](N)(C(=O)O)C1]

The product of step 4 (0.280 g, 0.527 mmol) was dissolved in a biphasic mixture of methanol (1.3 mL) and hexane (2.6 mL). Isobutylboronic acid (0.375 mg, 3.68 mmol) and TFA (1 mL) was added. The reaction mixture was stirred vigorously at room temperature for 6 h. The methanol phase was separated and washed with hexane (3×2 mL), concentrated and purified by reverse phase HPLC to give 0.060 g of the title compound as a mixture of diastereomers. Yield: 20%. MS (ESI, m/e): 333 [M-$H_2$O+1]$^+$.

$^1$HNMR Spectrum: (400 MHz, $D_2$O) δ 3.97-3.90 (m, 1H), 3.78-3.70 (m, 1H), 3.55-3.48 (m, 1H), 3.23-3.14 (m, 1H), 2.99-2.92 (m, 1H), 2.86-2.78 (m, 1H), 2.60-2.48 (m, 1H), 1.60-1.42 (m, 1H), 1.40-1.16 (m, 5H), 0.77-0.62 (m, 2H)

Example 16

(rac)trans-3-amino-1-(N—((R)-1-aminopropan-2-yl)sulfamoyl)-4-(3-boronopropyl)pyrrolidine-3-carboxylic Acid (Diastereomers), 2,2,2-trifluoroacetic Acid Salt (1:2)

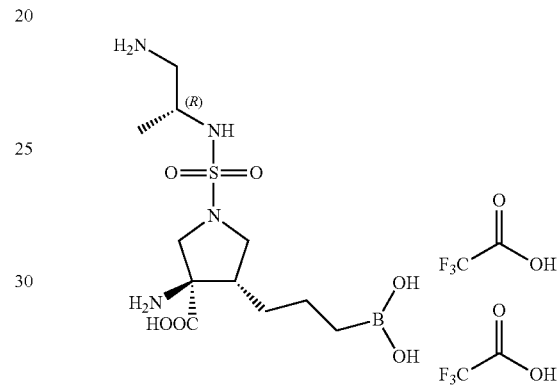

Step 1 tert-butyl (R)-(2-((2-oxooxazolidine)-3-sulfonamido)propyl)carbamate

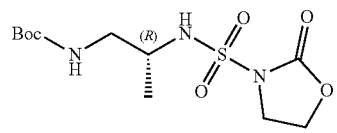

To a 25 mL 3-neck-flask initially charged with dichloromethane (5 mL) was added chlorosulfonyl isocyanate (0.89 g, 6.31 mmol) at room temperature and under a nitrogen atmosphere. The reaction mixture was cooled to about 0-5° C., and a solution of 2-bromoethanol (0.79 g, 6.31 mmol, 1.2 equiv.) in dichloromethane (5 mL) was slowly added over 20 min to keep the reaction temperature between 0 and 10° C. Stirring of the reaction mixture was continued at the same temperature for a minimum of 30 min. A mixture of compound tert-butyl (R)-(2-aminopropyl)carbamate (1.00 g, 5.74 mmol, 1.0 equiv.) and triethylamine (1.74 g, 1.72 mmol) in dichloromethane (1 mL) was then added at such an addition rate that the reaction temperature was maintained between 0 and 10° C. The reaction mixture was heated to room temperature. Aqueous hydrochloric acid (0.2 N, 50 mL) was then added and stirred for 30 min. The reaction mixture was decanted and the separated organic layer washed with aqueous hydrochloric acid (10 mL×2, 0.05 N). Then organic layer was washed with NaCl (10 mL) and water (10 mL). The organic layer was placed under vacuum to distill the DCM at 40° C. Then concentrated to purified by flash chromatography (EA:PE=0-80%) to give 1.51 g of the title product. Yield: 81.4%. MS (ES+): 324 [M+1]+.

1H NMR Spectrum: 1H NMR (400 MHz, CDCl$_3$) δ 5.98 (d, 1H), 5.05 (s, 1H), 4.50-4.38 (m, 2H), 4.11-4.04 (m, 2H), 3.73 (dd, 1H), 3.34-3.23 (m, 1H), 3.20-3.10 (m, 1H), 1.47 (s, 9H), 1.32-1.22 (t, 3H).

Step 2 (rac)benzyl trans-4-allyl-3-azido-1-(N—((R)-1-((tert-butoxycarbonyl)amino)propan-2-yl)sulfamoyl)pyrrolidine-3-carboxylate (Diastereomers)

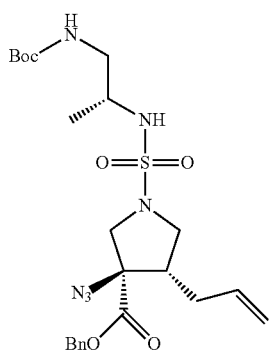 [SMILES: C=CC[C@H]1CN(S(=O)(=O)N[C@H](C)CNC(=O)OC(C)(C)C)C[C@@]1(N=[N+]=[N-])C(=O)OCc1ccccc1]

To a solution of the product of step 1 (0.050 g, 0.17 mmol) in MeCN (3 mL) was added Et$_3$N (0.071 g, 0.70 mmol) at r.t. The reaction mixture was stirred at r.t. for 15 min and then treated with (rac)-benzyl trans-4-allyl-3-azidopyrrolidine-3-carboxylate (0.056 g, 0.17 mmol). Stirred for 16 hrs at 70° C., then heated to 70° C. for 8 hrs. The reaction mixture diluted with DCM. Concentrated and purified by flash column chromatography (EA:PE=0-100%) to give 0.63 g of the title product. yield 90.0%. MS (ES+): 523 [M+1]+.

Step 3 (rac)benzyl trans-3-azido-1-(N—((R)-1-((tert-butoxycarbonyl)amino)propan-2-yl)sulfamoyl)-4-(3-(4,4,5,5-tetramethyl-1,3,2-dioxaborolan-2-yl)propyl)pyrrolidine-3-carboxylate, (Diastereomers)

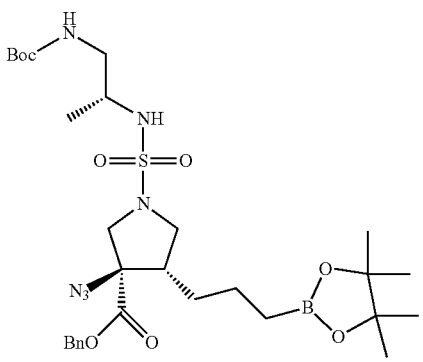 [SMILES: C[C@H](CNC(=O)OC(C)(C)C)NS(=O)(=O)N1C[C@H](CCCB2OC(C)(C)C(C)(C)O2)[C@](N=[N+]=[N-])(C(=O)OCc2ccccc2)C1]

A solution of the product of step 3 (0.094 g, 0.169 mmol), bis (1,5-cyclootadiene) diiridium dichloride (0.023 g, 0.034 mmol) and 1,2-bis (diphenyphosphino) enthane (0.027 g, 0.068 mmol) in DCM (2 mL) was stirred for 30 min under N$_2$ atmosphere. Then, the solution of 4,4,5,5-tetramethy[1,3,2]dioxaborolane (0.108 g, 0.845 mmol) in DCM (2 mL) was added dropwise at 0° C. The reaction was allowed to warm to r.t. and stirred overnight. Concentrated and purified by flash chromatography (EA:PE=20-40%) to give the title product (0.067 g, 57.0% yield) as a yellow oil. Yield: 57.0%. MS (ES+): 651 [M+1]+.

Step 5 (rac)trans-3-amino-1-(N—((R)-1-((tert-butoxycarbonyl)amino)propan-2-yl)sulfamoyl)-4-(3-(4,4,5,5-tetramethyl-1,3,2-dioxaborolan-2-yl)propyl)pyrrolidine-3-carboxylic Acid (Diastereomers)

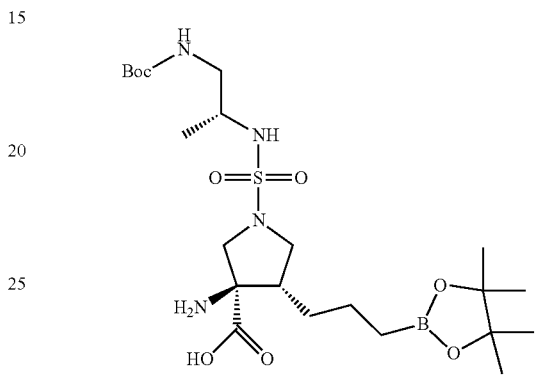

The product of step 4 (0.180 g, 0.410 mmol) was dissolved in a 1:1 mixture of ethyl acetate and ethanol (4 mL). 10% Pd—C(10 mg) was added and the solution was degassed under vacuum and purged with H$_2$. Stirred for 5 hrs at RT. The solution was filtered through a 4 u syringe filter to remove traces of palladium and concentrated to the title product. MS (ES+): 535 [M+1]+.

Step 6 (rac)trans-3-amino-1-(N—((R)-1-aminopropan-2-yl)sulfamoyl)-4-(3-boronopropyl)pyrrolidine-3-carboxylic Acid (Diastereomers), 2,2,2-trifluoroacetic Acid Salt (1:2)

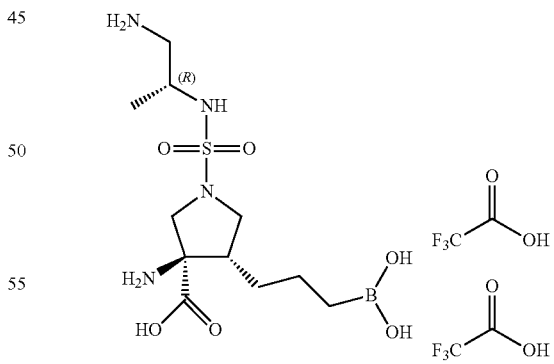

A suspension of the product of step 5 in 4 N hydrochloric acid (3 mL) was stirred at 50° C. for 2 hrs and then cooled to r.t. The solution was concentrated under vacuum and purified by reverse phase HPLC to give the title product (94.0 mg, 28.5% yield over 2 steps) as a pale solid (94.0 mg). Yield: 28.5%. MS (ES+): 335 [M-H$_2$O+1]+.

1H NMR Spectrum: 1H NMR (400 MHz, D$_2$O) δ 3.87 (dd, J=11.0, 3.6 Hz, 1H), 3.71 (dt, J=8.4, 5.8 Hz, 2H), 3.49

(t, J=10.4 Hz, 1H), 3.17-3.01 (m, 2H), 2.87 (dd, J=13.2, 9.3 Hz, 1H), 2.62 (s, 1H), 2.53-2.38 (m, 1H), 1.52 (d, J=5.9 Hz, 1H), 1.42-1.26 (m, 2H), 1.22 (dd, J=13.2, 6.6 Hz, 3H+1H), 0.70 (dd, J=15.6, 8.7 Hz, 2H).

Example 17

(rac)trans-3-amino-1-(N—((R)-2-aminopropyl)sulfamoyl)-4-(3-boronopropyl)pyrrolidine-3-carboxylic Acid (Diastereomers), 2,2,2-trifluoroacetic Acid Salt(1:2) (Diasteromers)

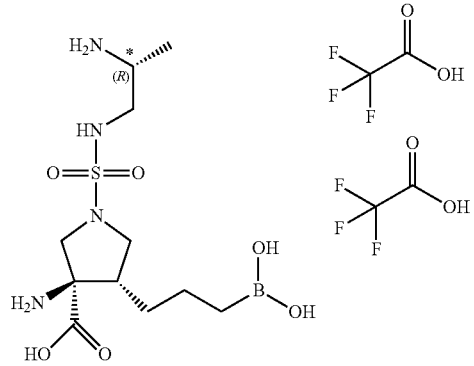

Starting with (R)-tert-butyl (1-aminopropan-2-yl)carbamate and (rac)-3-benzyl 1-(tert-butyl) trans-4-allyl-3-azidopyrrolidine-1,3-dicarboxylate, the title compound was prepared as a mixture of diastereomers by the same procedures described for Example 16. MS (ES+): 335 [M-H₂O+1]+.

¹H NMR Spectrum: ¹H NMR (400 MHz, D₂O) δ 3.87 (d, J=11.2 Hz, 1H), 3.73 (t, J=8.4 Hz, 1H), 3.46 (d, J=11.2 Hz, 1H), 3.41-3.30 (m, 2H), 3.21-3.10 (m, 2H), 2.53-2.48 (m, 1H), 1.54-1.48 (m, 1H), 1.37-1.27 (m, 2H), 1.21 (d, J=6.8 Hz 3H), 0.74-0.66 (m, 2H).

Example 18

(rac)trans-3-amino-1-(N—((S)-2-aminopropyl)sulfamoyl)-4-(3-boronopropyl)pyrrolidine-3-carboxylic Acid (Diasteromers), 2,2,2-trifluoroacetic Acid Salt (1:2)

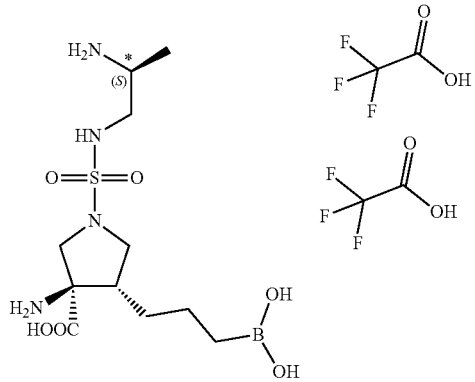

Starting with (S)-tert-butyl (1-aminopropan-2-yl)carbamate and (rac)-3-benzyl 1-(tert-butyl) trans-4-allyl-3-azidopyrrolidine-1,3-dicarboxylate, the title compound was prepared as a mixture of diastereomers by the same procedures described for Example 16. MS (ES+): 349 [M−18+1]+.

¹HNMR Spectrum: ¹H NMR (400 MHz, D₂O) δ 4.05 (d, J=10.8 Hz, 1H), 3.66 (t, J=8.4 Hz, 1H), 3.43 (d, J=11.2 Hz, 1H), 3.35-3.25 (m, 2H), 3.16-3.06 (m, 2H), 2.48-2.44 (m, 1H), 1.48-1.46 (m, 1H), 1.36-1.16 (m, 3H), 1.14 (d, J=6.8 Hz, 3H), 0.67-0.61 (m, 2H).

Example 19

(rac)-(trans)3-amino-1-(N-((1-aminocyclopropyl)methyl)sulfamoyl)-4-(3-boronopropyl)pyrrolidine-3-carboxylic Acid, 2,2,2-trifluoroacetic Acid Salt (1:2)

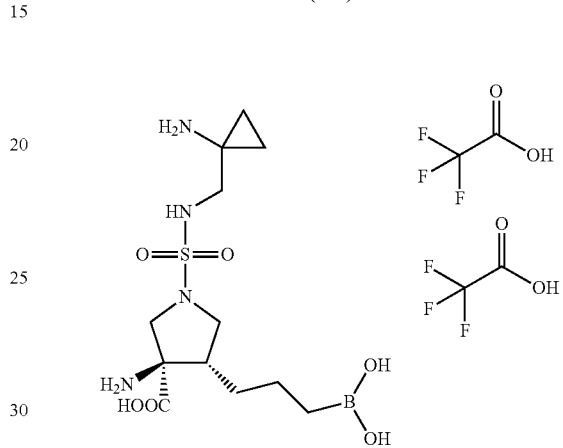

Starting with tert-butyl (1-(aminomethyl)cyclopropyl) carbamate and 1-(tert-butyl) 3-(1-phenyl-1λ³-ethyl) (rac)-trans-4-allyl-3-azidopyrrolidine-1,3-dicarboxylate, the title compound was prepared by the same procedures described for Example 16. MS (ES+): 347 [M-H₂O+1]+.

¹H NMR Spectrum: ¹H NMR (400 MHz, D₂O) δ 3.89 (d, J=10.8 Hz, 1H), 3.73 (t, J=8.4 Hz, 1H), 3.50 (d, J=10.8 Hz, 1H), 3.35 (s, 2H), 3.17-3.12 (m, 1H), 2.49-2.46 (m, 1H), 1.57-1.51 (m, 2H), 1.37-1.27 (m, 2H), 1.01 (t, J=7.6 Hz, 2H), 0.89 (t, J=7.6 Hz, 2H), 0.76-0.66 (m, 2H).

Example 20

(rac)trans-3-amino-1-(N-((rac)cis-2-aminocyclohexyl)sulfamoyl)-4-(3-boronopropyl)pyrrolidine-3-carboxylic Acid (Diastereomers), 2,2,2-trifluoroacetic Acid Salt (1:2)

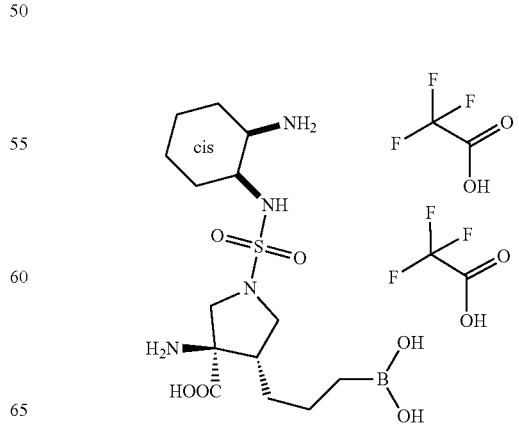

Starting with (rac)-cis-(2-Amino-cyclohexyl)-carbamic acid tert-butyl ester and (rac)-3-benzyl 1-(tert-butyl) trans-4-allyl-3-azidopyrrolidine-1,3-dicarboxylate, the title compound was prepared as a mixture of diastereomers by the same procedures described for Example 16. MS (ES$^+$): 375 [M-H$_2$O+1]$^+$.

$^1$H NMR Spectrum: $^1$H NMR (400 MHz, D$_2$O) δ 3.83 (dd, J=10.4, 6.4 Hz, 1H), 3.75 (s, 1H), 3.64-3.61 (m, 1H), 3.41-3.36 (m, 2H), 3.25-3.22 (m, 1H), 2.49-2.39 (m, 1H), 1.80-1.76 (m, 2H), 1.68-1.65 (m, 2H), 1.55-1.51 (m, 2H), 1.41-1.23 (m, 6H), 0.84 (t, J=5.6 Hz, 2H).

Example 21

(rac)-trans-3-amino-1-(N-(3-aminopropyl)sulfamoyl)-4-(3-boronopropyl)pyrrolidine-3-carboxylic Acid (diastereomers), 2,2,2-trifluoroacetic Acid Salt (1:2)

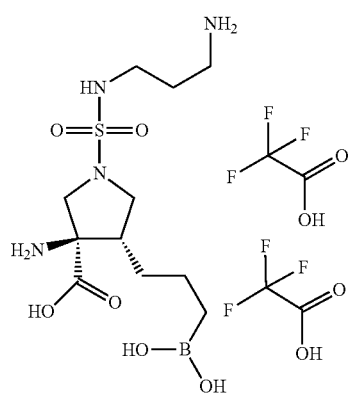

Starting with tert-butyl (3-aminopropyl)carbamate and (rac)-3-benzyl 1-(tert-butyl) trans-4-allyl-3-azidopyrrolidine-1,3-dicarboxylate, the title compound was prepared by the same procedures described for Example 16. MS (ES+): 335 [M-H$_2$O+1]$^+$.

$^1$H NMR Spectrum: $^1$H NMR (400 MHz, D$_2$O) δ 3.81 (d, J=10.8 Hz, 1H), 3.63 (t, J=8.4 Hz, 1H), 3.41 (d, J=10.8 Hz, 1H), 3.10-3.01 (m, 4H), 2.99-2.91 (m, 2H), 2.42-2.39 (m, 1H), 1.80-1.73 (m, 2H), 1.29-1.26 (m, 1H), 1.23-1.10 (m, 4H), 0.67-0.61 (m, 2H).

Example 22

(rac)-trans-3-amino-1-(N-(trans-2-aminocyclohexyl)sulfamoyl)-4-(3-boronopropyl)pyrrolidine-3-carboxylic Acid (Diastereomers), 2,2,2-trifluoroacetic Acid Salt (1:2)

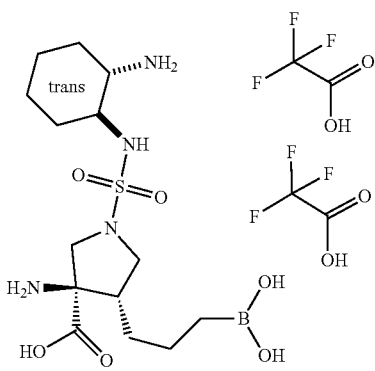

Starting with (rac)trans-(2-Amino-cyclohexyl)-carbamic acid tert-butyl ester and (rac)-3-benzyl 1-(tert-butyl) trans-4-allyl-3-azidopyrrolidine-1,3-dicarboxylate, the title compound was prepared as a mixture of diastereomers by the same procedures described for Example 16. MS (ES$^+$): 375 [M-H$_2$O+1]$^+$.

$^1$H NMR Spectrum: $^1$H NMR (400 MHz, D$_2$O) δ 3.88-3.85 (m, 1H), 3.74-3.70 (m, 1H), 3.52-3.45 (m, 1H), 3.25-3.10 (m, 2H), 2.50-2.40 (m, 1H), 2.14-2.10 (m, 1H), 2.10-2.01 (m, 1H), 1.51-1.11 (m, 10H), 0.75-0.68 (m, 2H).

Example 23

(rac)-trans-3-amino-1-(N-((rac)cis-4-aminotetrahydrofuran-3-yl)sulfamoyl)-4-(3-boronopropyl)pyrrolidine-3-carboxylic Acid (Diastereomers), 2,2,2-trifluoroacetic Acid Salt (1:2)

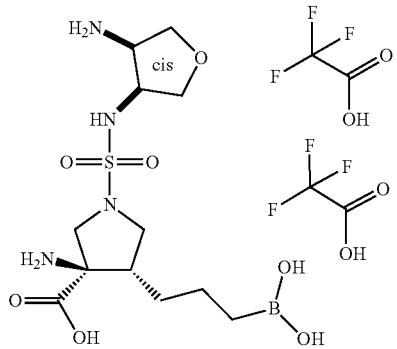

Step 1 (cis)di-tert-butyl (tetrahydrofuran-3,4-diyl)dicarbamate

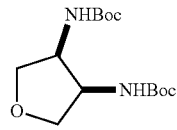 [SMILES: CC(C)(C)OC(=O)N[C@H]1COC[C@H]1NC(=O)OC(C)(C)C]

To the solution of tetrahydrofuran-3,4-diamine (500 mg, 4.9 mmol, 1.0 equiv.) in DCM (10 mL) was added TEA (1.48 g, 14.7 mmol, 3.0 equiv.) and (Boc)₂O (2.12 g, 9.8 mmol, 2.0 equiv.) at RT. the mixture was stirred for overnight at this temperature. The solution was quenched with 50 mL of HCl (0.1 M). the organic phase was separated and washed with brine, dried over sodium sulfate, concentrated under vacuum to give 880 mg of the title product as white solid, Yield: 59%. MS (ES+): 303 [M+1]⁺.

Step 2 (rac)cis-tert-butyl (4-aminotetrahydrofuran-3-yl)carbamate

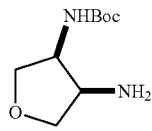

A solution of the product of step 1 (880 mg, 2.9 mmol, 1 equiv.) in DCM (5 mL) was added acetyl chloride (226 mg, 2.9 mmol, 1 equiv.) at RT. The resulting mixture was stirred for overnight at this temperature. The mixture was concentrated to afford the title product as white solid 500 mg. Yield: 85%. MS (ES+): 203 [M+1]⁺.

Step 3 (rac)trans-3-amino-1-(N-((rac)cis-4-aminotetrahydrofuran-3-yl)sulfamoyl)-4-(3-boronopropyl)pyrrolidine-3-carboxylic Acid (Diastereomers), 2,2,2-trifluoroacetic Acid Salt (1:2)

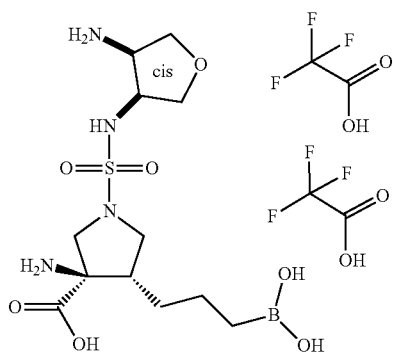

Starting with (rac)cis-tert-butyl (4-aminotetrahydrofuran-3-yl)carbamate and (rac)-3-benzyl 1-(tert-butyl) trans-4-allyl-3-azidopyrrolidine-1,3-dicarboxylate, the title compound was prepared as a mixture of diastereomers by the same procedures described for Example 16. MS (ES⁺): 363 [M-H₂O+1]⁺.

¹H NMR Spectrum: ¹H NMR (400 MHz, D₂O) δ 4.29 (s, 1H), 4.01-3.91 (m, 4H), 3.81-3.67 (m, 3H), 3.48-3.44 (m, 1H), 3.06-3.01 (m, 1H), 2.48 (s, 1H), 1.48-1.46 (m, 1H), 1.26 (m, 1H), 1.24-1.10 (m, 5H), 0.65-0.63 (m, 2H).

Example 24

(rac)-trans-3-amino-1-(N-((rac)trans-3-aminocyclobutyl)sulfamoyl)-4-(3-boronopropyl)pyrrolidine-3-carboxylic Acid Compound with 2,2,2-trifluoroacetic Acid (1:2)

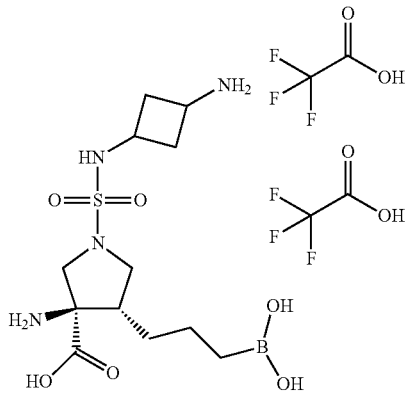

Step 1 tert-butyl (3-(benzylamino)cyclobutyl)carbamate

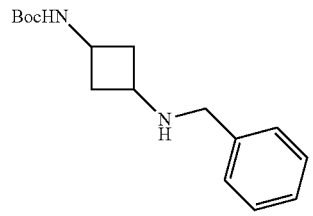 [SMILES: CC(C)(C)OC(=O)NC1CC(NCc2ccccc2)C1]

To the solution of (3-Oxo-cyclobutyl)-carbamic acid tert-butyl ester (1.2 g, 6.4 mmol, 1.0 equiv.) in methanol (50 mL) was added benzylamine (760 mg, 7.1 mmol, 1.1 equiv) at room temperature. The solution was stirred for 10 min at room temperature, and then NaBH₃CN (806 mg, 12.8 mmol, 2 equiv.) was added. After stirring for 30 min, AcOH (12 mL) was added to the mixture carefully. The reaction solution was stirred overnight. The resulting solution was concentrated and the residue was purified through silica column chromatography (PE:EA=5:1 to 1:1) to afford 920 mg of the title product as white solid. Yield=51%. MS (ES⁺): 277 [M+1]⁺.

Step 2 cis/trans-tert-butyl (3-aminocyclobutyl)carbamate

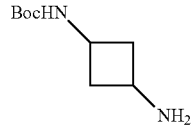

A solution of the product of step 1 (1.1 mg, 4.0 mmol, 1 equiv.) in methanol (25 mL) was added Pd(OH)$_2$/C (200 mg, 20%). the resulting mixture was degassed with hydrogen. The reaction was stirred for overnight at room temperature. The mixture was filtrated and the mother liquid was concentrated to afford a white solid 500 mg. which was purified with reverse phase HPLC (5%, 10 min; 5-10% 20 min, MeCN:water) to give 400 mg of the title product as white solid. Yield: 54%. MS (ES$^+$): 187 [M+1]$^+$.

$^1$H NMR Spectrum: $^1$H NMR (400 MHz, D$_2$O) δ 4.63 (br, 1H), 3.71 (m, 1H), 3.14-3.10 (m, 2H), 2.72-2.70 (m, 2H), 1.49 (s, 9H).

Step 3 (rac)-trans-3-amino-1-(N-((rac)trans-3-aminocyclobutyl)sulfamoyl)-4-(3-boronopropyl)pyrrolidine-3-carboxylic Acid, 2,2,2-trifluoroacetic Acid Salt (1:2)

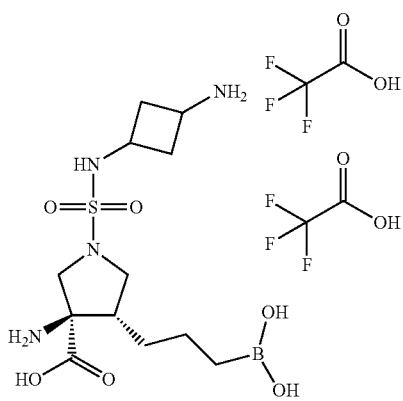

Starting with cis/trans-tert-butyl (3-aminocyclobutyl)carbamate and 1-(tert-butyl) 3-(1-phenyl-1λ$^3$-ethyl) (rac)-trans-4-allyl-3-azidopyrrolidine-1,3-dicarboxylate, the title compound was prepared as a mixture of isomers by the same procedures described for Example 16. MS (ES$^+$): 463 [M-H$_2$O+1]$^+$.

$^1$H NMR Spectrum: $^1$H NMR (400 MHz, D$_2$O) δ 3.88-3.82 (m, 1H), 3.75-3.68 (m, 2H), 3.58-3.47 (m, 2H), 3.11-3.06 (m, 1H), 2.77-2.71 (m, 2H), 2.52-2.50 (m, 1H), 2.15-2.08 (m, 2H), 1.36-1.34 (m, 1H), 1.32-1.16 (m, 3H), 0.75-0.69 (m, 2H).

Example 25

(rac)-trans-3-amino-1-(N-(2-amino-2-methylpropyl)sulfamoyl)-4-(3-boronopropyl)pyrrolidine-3-carboxylic Acid, (1:2) 2,2,2-trifluoroacetic Acid Salt

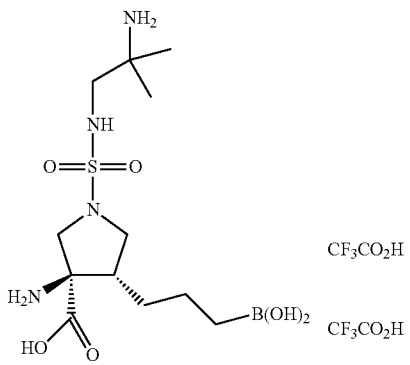 [SMILES: CC(C)(N)CNS(=O)(=O)N1C[C@H](CCCB(O)O)[C@](N)(C(=O)O)C1 ; "CF3CO2H" ; "CF3CO2H"]

Starting with tert-butyl (1-amino-2-methylpropan-2-yl)carbamate and (rac)-3-benzyl 1-(tert-butyl) trans-4-allyl-3-azidopyrrolidine-1,3-dicarboxylate, the title compound was prepared by the same procedures described for Example 17. MS (ES+): 349 [M-H$_2$O+1]$^+$.

$^1$HNMR Spectrum: (400 MHz, D$_2$O) δ 3.94 (d, J=11.2 Hz, 1H), 3.75 (t, J=7.6 Hz, 1H), 3.53 (d, J=11.2 Hz, 1H), 3.23 (s, 2H), 3.10 (t, J=7.6 Hz, 1H), 2.59-2.49 (m, 1H), 1.60-1.50 (m, 1H), 1.44-1.18 (m, 3H), 1.20 (s, 6H), 0.80-0.65 (m, 2H).

Example 26

(rac)-trans-3-amino-1-(N-(1-amino-2-methylpropan-2-yl)sulfamoyl)-4-(3-boronopropyl)pyrrolidine-3-carboxylic Acid, (1:2) 2,2,2-trifluoroacetic Acid Salt

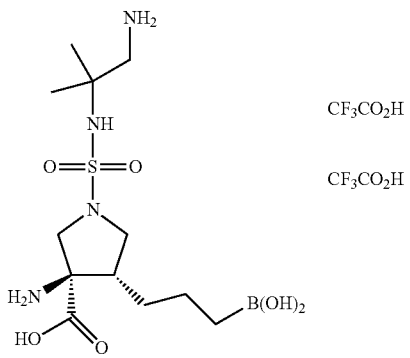 [SMILES: CC(C)(CN)NS(=O)(=O)N1C[C@H](CCCB(O)O)[C@](N)(C(=O)O)C1 ; "CF3CO2H" ; "CF3CO2H"]

Starting with tert-butyl (2-amino-2-methylpropyl)carbamate and (rac)-3-benzyl 1-(tert-butyl) trans-4-allyl-3-azidopyrrolidine-1,3-dicarboxylate, the title compound was prepared by the same procedures described for Example 17. MS (ES+): 349 [M-H$_2$O+1]$^+$.

$^1$HNMR Spectrum: (400 MHz, D$_2$O) δ 3.94 (d, J=11.2 Hz, 1H), 3.75 (t, J=7.6 Hz, 1H), 3.53 (d, J=11.2 Hz, 1H), 3.39 (t, J=7.6 Hz, 1H), 3.17 (s, 2H), 2.59-2.49 (m, 1H), 1.60-1.50 (m, 1H), 1.45 (s, 6H), 1.44-1.18 (m, 3H), 0.80-0.65 (m, 2H).

Example 27

(3R,4S)-3-amino-1-(N-(2-aminoethyl)-N-methylsulfamoyl)-4-(3-boronopropyl)pyrrolidine-3-carboxylic Acid, 2,2,2-trifluoroacetic Acid Salt (1:2)

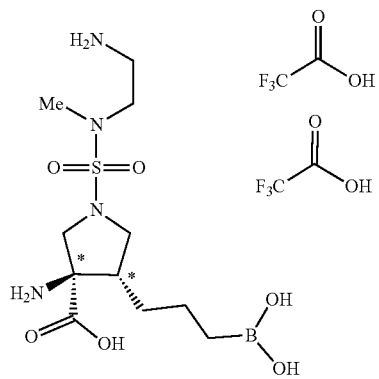

Step 1 tert-butyl (2-((chlorosulfonyl)(methyl)amino)ethyl)carbamate

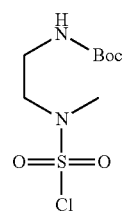

To the solution of tert-butyl (2-(methylamino)ethyl)carbamate (210 mg, 1.2 mmol, 1.0 equiv.) and pyridine (284 mg, 3.6 mmol, 3.0 equiv.) in DCM (5 mL) was added sulfuryl dichloride (194 mg, 1.44 mmol, 1.2 equiv.) carefully under $N_2$ at 5° C., the mixture was stirred for 3 h at room temperature. The title product was obtained and the reaction mixture was used in the next step directly. MS (ES+): 273 [M+1]$^+$.

Step 2 (R)-1-phenylethyl (3R,4S)-4-allyl-3-azido-1-(N-(2-((tert-butoxycarbonyl)amino)ethyl)-N-methylsulfamoyl)pyrrolidine-3-carboxylate

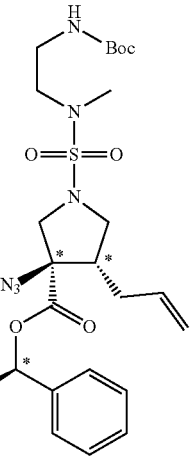

To the solution of the product of step 1 (414 mg, 1.0 mmol, 1.0 equiv.) and $Et_3N$ (303 mg, 3.0 mmol, 3.0 equiv.) in DCM (5 mL) was added Intermediate 4 (301 mg, 1.0 mmol, 1.0 equiv.) in DCM (5 ml) at 5° C. The resulted mixture was degassed with $N_2$ and stirred overnight. The mixture was concentrated and the residue was purified through silica gel chromatography (EA/PE=0-50%) to afford the title product as white solid 300 mg. Yield: 56%. MS (ES+):538 [M+1]$^+$.

Step 3 (R)-1-phenylethyl (3R,4S)-3-azido-1-(N-(2-((tert-butoxycarbonyl)amino)ethyl)-N-methylsulfamoyl)-4-(3-(4,4,5,5-tetramethyl-1,3,2-dioxaborolan-2-yl)propyl)pyrrolidine-3-carboxylate

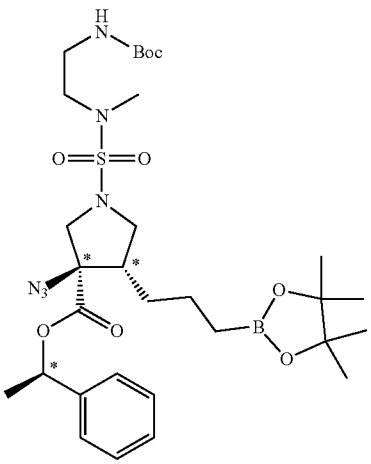 [SMILES: C[C@@H](OC(=O)[C@]1(N=[N+]=[N-])CN(S(=O)(=O)N(C)CCNC(=O)OC(C)(C)C)C[C@@H]1CCCB1OC(C)(C)C(C)(C)O1)c1ccccc1]

A solution of the product of step 2 (300 mg, 0.56 mmol, 1.0 equiv.), DPPE (89 mg, 0.22 mmol, 0.4 equiv.) and [IrCODCl]$_2$ (150 mg, 0.22 mmol, 0.4 equiv.) in DCM (3 mL) was degassed with $N_2$ three times and stirred at room temperature for 30 min, and then the resulted solution was cooled to 0° C. with an ice/water bath. A solution of tetramethyl-[1,3,2]dioxaborolane (359 mg, 2.80 mmol, 5.0 equiv.) in 2 mL of DCM was added dropwise, after addition the reaction was allowed to be stirred at r.t. for 5 hours. The solution was purified by silica gel column chromatography (EA:PE=5:1 to 2:1) and 300 mg of title product as white solid was obtained. Yield: 92%. MS: (ES+): 665 [M+1]+.

Step 4 (3R,4S)-3-amino-1-(N-(2-((tert-butoxycarbonyl)amino)ethyl)-N-methylsulfamoyl)-4-(3-(4,4,5,5-tetramethyl-1,3,2-dioxaborolan-2-yl)propyl)pyrrolidine-3-carboxylicacid

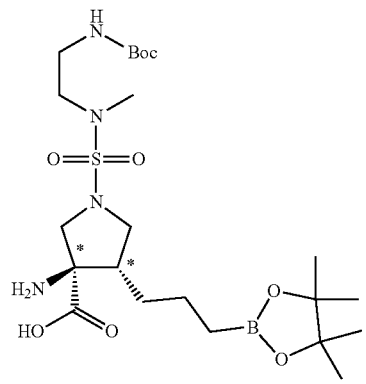 [SMILES: CN(CCNC(=O)OC(C)(C)C)S(=O)(=O)N1C[C@H](CCCB2OC(C)(C)C(C)(C)O2)[C@](N)(C(=O)O)C1]

To the solution of the product of step 3 (300 mg, 0.45 mmol, 1.0 equiv.) in 4 mL of EtOH/EA was added 40 mg of 10% Pd/C, the resulted mixture was degassed under vacuum and purged with hydrogen. The mixture was stirred under hydrogen atmosphere for overnight. The solution was filtered through a syringe filter to remove Pd/C, the solution was concentrated to afford 241 mg of the title product as colorless oil. Yield: 100%. MS (ES+): 535 [M+1]+.

Step 5 (3R,4S)-3-amino-1-(N-(2-aminoethyl)-N-methylsulfamoyl)-4-(3-boronopropyl)pyrrolidine-3-carboxylic Acid, 2,2,2-trifluoroacetic Acid Salt (1:2)

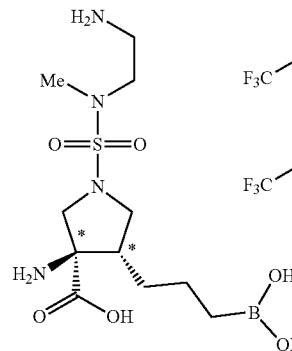

To the solution of the product of step 4 in 2 mL of DCM was added 1 mL of TFA, the solution was stirred for 1 h, the mixture was concentrated to afford a brown oil which was charged in 3 mL of water, and then 1 mL of TFA was added and the mixture was stirred for 30 min. the mixture was extracted with MTBE, The water phase was concentrated and the residue was purified by reversed phase Prep-HPLC to give 15 mg of the title product as white solid. Yield: 9.4%, MS (ES+): 335 [M-H$_2$O+1]+.

$^1$HNMR (400 MHz, D$_2$O) S 3.94 (d, J=10.8 Hz, 1H), 3.70 (t, J=16.0 Hz, 1H), 3.49 (d, J=10.8 Hz, 1H), 3.43 (t, J=16 Hz, 2H), 3.15 (t, J=20 Hz, 1H), 3.08 (t, J=11.2 Hz, 2H), 2.80 (s, 3H), 2.54-2.52 (m, 1H), 1.50-1.47 (m, 1H), 1.29-1.12 (m, 3H), 0.68-0.61 (m, 2H).

Example 28

(3R,4S)-3-amino-1-(2-((2-aminoethyl)amino)-3,4-dioxocyclobut-1-en-1-yl)-4-(3-boronopropyl)pyrrolidine-3-carboxylic Acid, 2,2,2-trifluoroacetic Acid Salt (1:2)

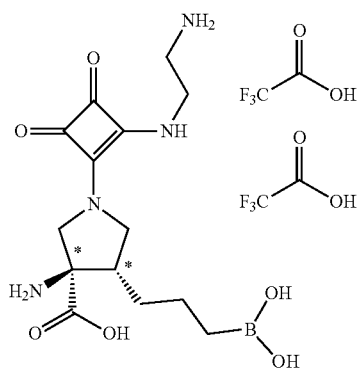

Step 1 [2-(2-Methoxy-3,4-dioxo-cyclobut-1-enylamino)-ethyl]-carbamic Acid Tert-Butyl Ester

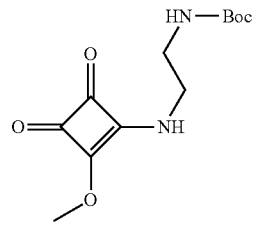

To the solution of 3,4-Dimethoxy-cyclobut-3-ene-1,2-dione (4.26 g, 3 mmol, 1.0 equiv.) in methanol (30 mL) was added (2-Amino-ethyl)-carbamic acid tert-butyl ester (4.8 g, 3 mmol, 1.0 equiv.) at room temperature. The solution was stirred overnight, and then was concentrated under vacuum. The residues were purified by silica gel column chromatography (PE:EA=5:1 to 1:1) to afford 6 g of the title product as white solid. Yield: 79%. MS (ES+): 215 [M+1−56]+.

Step 2 (R)-1-phenylethyl (3R,4S)-4-allyl-3-azido-1-(2-((2-((tert-butoxycarbonyl)amino)ethyl)amino)-3,4-dioxocyclobut-1-en-1-yl)pyrrolidine-3-carboxylate

Step 3 (R)-1-phenylethyl (3R,4S)-3-azido-1-(2-((2-((tert-butoxycarbonyl)amino)ethyl)amino)-3,4-dioxocyclobut-1-en-1-yl)-4-(3-(4,4,5,5-tetramethyl-1,3,2-dioxaborolan-2-yl)propyl)pyrrolidine-3-carboxylate

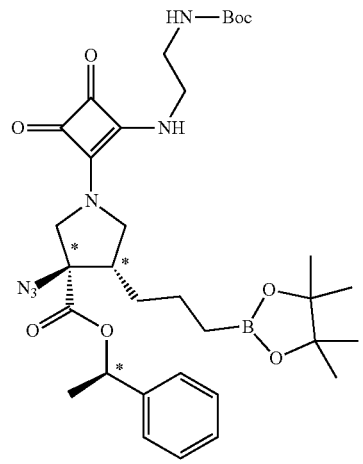

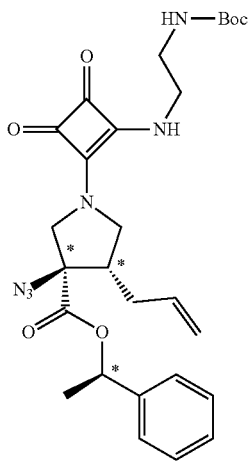 [SMILES: C=CC[C@H]1CN(c2c(NCCNC(=O)OC(C)(C)C)c(=O)c2=O)C[C@@]1(N=[N+]=[N-])C(=O)O[C@H](C)c1ccccc1]

To the solution of the product of the step 1 (300 mg, 1.1 mmol, 1.1 equiv.) in DMF (2 mL) was added the Intermediate 4 (1.0 mmol, 1.0 equiv.) and Et$_3$N (200 mg, 2 mmol, 2 equiv.). The resulted mixture was heated to 100° C. under N$_2$ for 2 hours. After cooling to room temperature, the mixture was poured into water (5 mL), and then extracted with EA (3×5 mL). The organic phase was combined and washed with brine, concentrated under vacuum to afford the crude product which was purified through silica gel column chromatography to give 140 mg of the title product as colorless oil. Yield: 16%. MS (ES+): 483 [M+1−56]$^+$.

A solution of the product of the step 2 (140 mg, 0.26 mmol, 1 equiv.), DPPE (44 mg, 0.10 mmol, 0.4 equiv.) and [IrCODCl]$_2$ (33 mg, 0.05 mmol, 0.2 equiv.) in DCM (5 mL) was degassed with N$_2$ three times and stirred at room temperature for 30 min, and then the resulted mixture was cooled to 0° C. with an ice/water bath. A solution of -Tetramethyl-[1,3,2]dioxaborolane (150 mg, 1.1 mmol, 5 equiv.) in 1 mL of DCM was added dropwise, the solution was allowed to warm to r.t. for 4 hours. The solution was purified by silica gel column chromatography (PE:EA=10: to 1:1, gradient) to give 74 mg of the title product as colorless oil. Yield: 71%. MS: (ES+): 667 [M+1]$^+$.

Step 4 (3R,4S)-3-amino-1-(2-((2-((tert-butoxycarbonyl)amino)ethyl)amino)-3,4-dioxocyclobut-1-en-1-yl)-4-(3-(4,4,5,5-tetramethyl-1,3,2-dioxaborolan-2-yl)propyl)pyrrolidine-3-carboxylic Acid

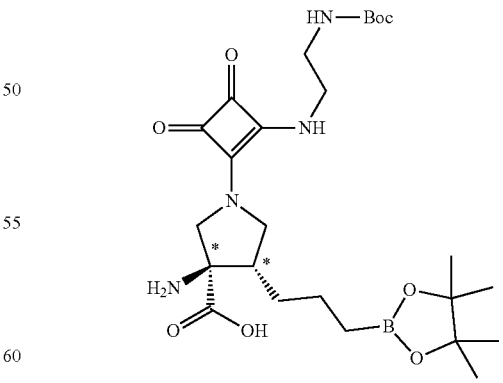

$^1$HNMR (400 MHz, CDCl$_3$) δ 7.37-7.26 (m, 5H), 6.53-6.47 (br, 1H), 5.97-6.03 (m, 1H), 5.65-5.55 (m, 1H), 5.10-4.90 (m, 3H), 4.25-4.20 (br, 1H), 4.03-3.97 (br, 1H), 3.90-3.63 (m, 4H), 3.40-3.25 (m, 2H), 2.60-2.50 (m, 1H), 2.10-2.00 (m, 1H), 1.8-1.78 (m, 1H), 1.67 (d, J=5.6 Hz, 3H), 1.40 (s, 9H).

To the solution of the product of step 3 (74 mg, 0.1 mmol, 1 equiv.) in 4 mL of EtOH/EA (1:1) was added 15 mg of Pd/C (10%), the resulted mixture was degassed under vacuum and purged with hydrogen. The mixture was stirred under hydrogen atmosphere for 3 hours. The solution was filtered through a syringe filter to remove Pd/C, the solution was concentrated to afford 55 mg of the title product as gray oil. MS (ES⁺): 537 [M+1]⁺.

Step 5 (3R,4S)-3-amino-1-(2-((2-aminoethyl)amino)-3,4-dioxocyclobut-1-en-1-yl)-4-(3-boronopropyl)pyrrolidine-3-carboxylic Acid, 2,2,2-trifluoroacetic Acid Salt (1:2)

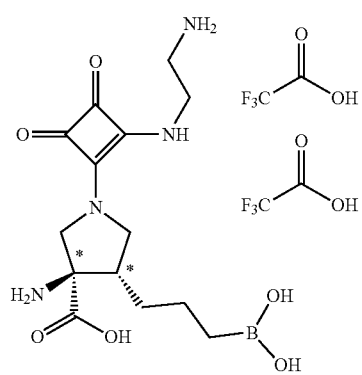

To the solution of the product of step 4 in 3 mL of DCM was added 1 mL of TFA, the solution was stirred for 30 min, the mixture was concentrated to afford brown oil which was charged in 3 mL of water, and then 1 mL of TFA was added and the mixture was stirred for 2 hours. The mixture was extracted with MTBE, the water phase was concentrated and the residue was purified by reversed phase Prep-HPLC to give 44 mg of the title product as white solid. Yield: 68%, MS (ES⁺): 337 [M-H₂O+1]⁺.

¹HNMR (400 MHz, D₂O) δ 4.50-4.20 (m, 2H), 3.93 (d, J=12.4 Hz, 2H), 3.70-3.40 (br, 2H), 3.54 (t, J=9.6 Hz, 1H), 3.16 (t, J=5.6 Hz, 2H), 2.60-2.50 (m, 1H), 1.60-1.50 (m, 1H), 1.37-1.20 (m, 3H), 0.72-0.58 (m, 2H).

Example 29

(3R,4S)-3-amino-1-(2-((2-aminoethyl)(methyl)amino)-3,4-dioxocyclobut-1-en-1-yl)-4-(3-boronopropyl)pyrrolidine-3-carboxylic Acid, 2,2,2-trifluoroacetic Acid Salt (1:2)

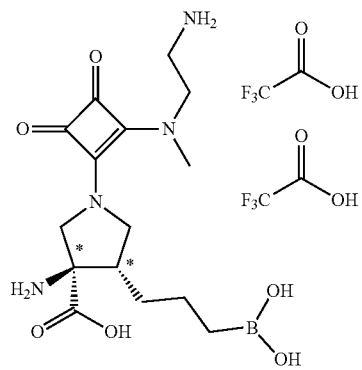

Step 1 tert-butyl (2-((2-methoxy-3,4-dioxocyclobut-1-en-1-yl)(methyl)amino)ethyl)carbamate

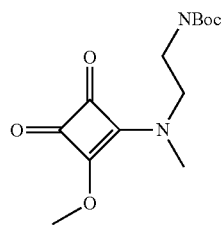

To the solution of 3,4-Dimethoxy-cyclobut-3-ene-,2-dione (4.26 g, 3 mmol, 1.0 equiv.) in methanol (30 mL) was added tert-butyl (2-(methylamino)ethyl)carbamate (5.21 g, 3 mmol, 1.0 equiv.) at room temperature. The solution was stirred overnight, and then was concentrated under vacuum. The residues were purified by silica gel column chromatography (PE:EA=5:1 to 1:1, gradient) to afford 6.3 g of the title product as pale green solid. Yield: 80%. MS (ES+): 229 [M+1−56]⁺.

Step 2 (R)-1-phenylethyl (3R,4S)-4-allyl-3-azido-1-(2-((2-((tert-butoxycarbonyl)amino)ethyl)(methyl)amino)-3,4-dioxocyclobut-1-en-1-yl)pyrrolidine-3-carboxylate

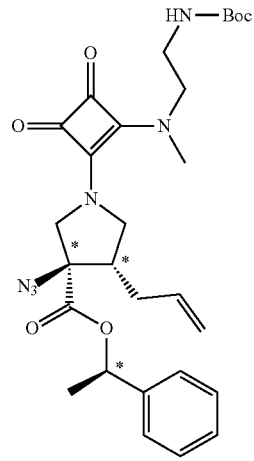 [SMILES: C=CC[C@H]1CN(c2c(N(C)CCNC(=O)OC(C)(C)C)c(=O)c2=O)C[C@@]1(N=[N+]=[N-])C(=O)O[C@H](C)c1ccccc1]

To the solution of the product of the step 1 (620 mg, 2.4 mmol, 1.2 equiv.) in DMF (5 mL) was added the Intermediate 4 (301 mg, 1.0 mmol, 1.0 equiv.) and Et₃N (400 mg, 4.0 mmol, 2 equiv.). The resulted mixture was heated to 100° C. under N₂ for 2 hours. After cooling to room temperature, the mixture was poured into water (5 mL), and then extracted with EA (5 mL*3). The organic phase was combined and washed with brine, concentrated under vacuum to afford the crude product which was purified by silica gel column chromatography to give 130 mg of the title product as a white solid. Yield: 12%. MS (ES+): 497 [M+1−56]⁺.

Step 3 (R)-1-phenylethyl (3R,4S)-3-azido-1-(2-((2-((tert-butoxycarbonyl)amino)ethyl)(methyl)amino)-3,4-dioxocyclobut-1-en-1-yl)-4-(3-(4,4,5,5-tetramethyl-1,3,2-dioxaborolan-2-yl)propyl)pyrrolidine-3-carboxylate

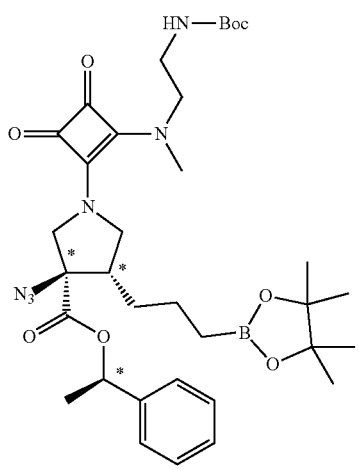 [SMILES: C[C@@H](OC(=O)[C@]1(N=[N+]=[N-])CN(c2c(N(C)CCNC(=O)OC(C)(C)C)c(=O)c2=O)C[C@@H]1CCCB1OC(C)(C)C(C)(C)O1)c1ccccc1]

A solution of the product of the step 2 (130 mg, 0.20 mmol, 1.0 equiv.), DPPE (44 mg, 0.10 mmol, 0.4 equiv.) and [IrCODCl]$_2$ (33 mg, 0.05 mmol, 0.2 equiv.) in DCM (5 mL) was degassed with N$_2$ three times and stirred at room temperature for 30 min, and then the resulted mixture was cooled to 0° C. with an ice/water bath. A solution of tetramethyl-[1,3,2]dioxaborolane (150 mg, 1.1 mmol, 5 equiv.) in 1 mL of DCM was added dropwise, after addition the reaction was allowed to warm to r.t. for 4 hours. The solution was purified by silica gel column chromatography (PE:EA=10:1 to 1:1, gradient) to give 110 mg of the title product as colorless oil. Yield: 71%. MS: (ES+): 681 [M+1]$^+$.

Step 4 (R)-3-amino-1-(2-((2-(((tert-butoxycarbonyl)amino)ethyl)(methyl)amino)-3,4-dioxocyclobut-1-en-1-yl)-4-(3-(4,4,5,5-tetramethyl-1,3,2-dioxaborolan-2-yl)propyl)-4l3-pyrrolidine-3-carboxylic Acid

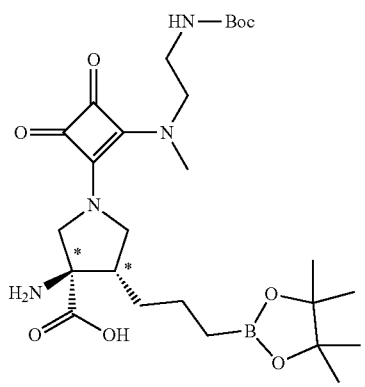 [SMILES: CN(CCNC(=O)OC(C)(C)C)c1c(N2C[C@H](CCCB3OC(C)(C)C(C)(C)O3)[C@](N)(C(=O)O)C2)c(=O)c1=O]

To the solution of the product of step 3 (110 mg, 0.16 mmol, 1.0 equiv.) in 4 mL of EA/EtOH (1:1) was added 15 mg of Pd/C, (10%), the resulted mixture was degassed under vacuum and purged with hydrogen. The mixture was stirred under Hydrogen atmosphere for 6 hours. The solution was filtered through a syringe filter to remove Pd/C, the solution was concentrated to afford 100 mg of the title product as gray oil. MS (ES$^+$): 551 [M+1]$^+$.

Step 5 (3R,4S)-3-amino-1-(2-((2-aminoethyl)(methyl)amino)-3,4-dioxocyclobut-1-en-1-yl)-4-(3-boronopropyl)pyrrolidine-3-carboxylic Acid, 2,2,2-trifluoroacetic Acid Salt (1:2)

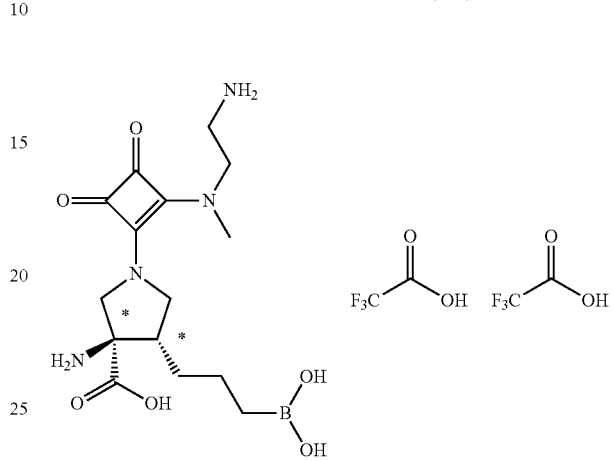

To the solution of the product of step 4 in 3 mL of DCM was added 1 mL of TFA, the solution was stirred overnight, the mixture was concentrated to afford brown oil which was charged in 3 mL of water, and then 1 mL of TFA was added and the mixture was stirred for 1 hour. The mixture was extracted with MTBE, the water phase was concentrated and the residue was purified by reversed phase Prep-HPLC to give 12.6 mg of title product as white solid. Yield: 13%, MS (ES$^+$): 351 [M-H$_2$O+1]$^+$.

$^1$HNMR (400 MHz, D$_2$O) δ 4.48 (d, J=12.0 Hz 1H), 4.13 (t, J=9.6 Hz, 1H), 4.06-3.90 (m, 3H), 3.54 (t, J=9.6 Hz, 1H), 3.18 (t, J=6.0 Hz, 2H), 3.07 (s, 3H), 2.68-2.53 (m, 1H), 1.62-1.52 (m, 1H), 1.37-1.14 (m, 3H), 0.73-0.58 (m, 2H).

SYNTHESIS OF INTERMEDIATES

Intermediate 1

(rac)trans-1-(tert-butyl)3-((R)-1-phenylethyl)-4-allyl-3-azidopyrrolidine-1,3-dicarboxylate (diastereomers)

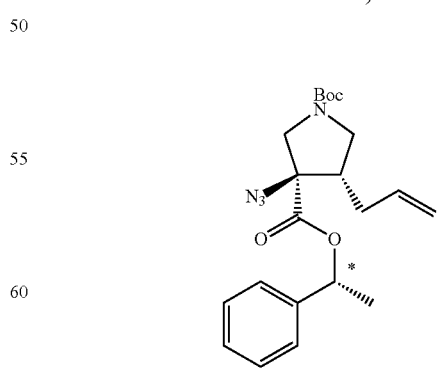

To a stirred solution of (rac)-4-allyl-3-azido-1-(tert-butoxycarbonyl)pyrrolidine-3-carboxylic acid (150.0 g, crude) from literature procedure in DCM (2200 mL) was added DMAP (6.2 g) and (R)-(+)-1-Phenylethanol (50.0 g). The above solution was added EDCI (116.5 g) in portions. The result mixture was stirred at r.t. for 8 hours. LCMS showed phenylethanol consumed completely. The reaction mixture was washed with water (3×2.0 L). The organic layer was dried over anhydrous sodium sulfate, concentrated under vacuum and purified by silica gel flash chromatography (EA:PE=0% to 20%) to give the title product as yellow oil, 112.6 g, yield 54%. MS (ESI, m/e): 301 [M−100+1]⁺.

Intermediate 2

1-(tert-butyl) 3-((R)-1-phenylethyl) (3R,4S)-4-allyl-3-azidopyrrolidine-1,3-dicarboxylate Enantiomer

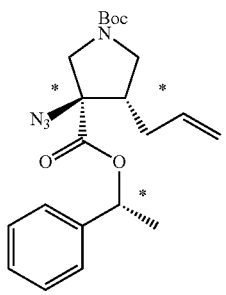

Intermediate 1 was separated using Chiracel OD-H 5 μm, 20 mm×250 mm column at r.t., using Hex:IPA=98:2 as eluent. Flow rate 15 mL/min. The sample was analyzed using Chiracel OD-H 5 μm, 4.6 mm×250 mm column using Hex:IPA=98:2 as eluent. The peak at 6.73 min was the title compound and the other enantiomer appears at 8.47 min. MS (ESI, m/e): 301 [M−100+1]⁺.

Intermediate 3

(R)-1-phenylethyl (rac)trans-4-allyl-3-azidopyrrolidine-3-carboxylate diastereomers

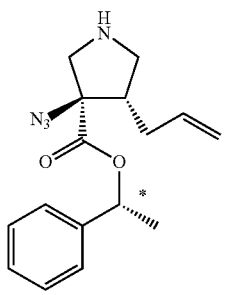 [SMILES: C=CC[C@H]1CNC[C@@]1(N=[N+]=[N-])C(=O)O[C@H](C)c1ccccc1]

Trifluoroacetic acid (4 mL) was added dropwise to the solution of the product of Intermediate 1 (4.0 g) in CH₂Cl₂ (30 mL) at 0° C. and the reaction was stirred for 2 h at r.t. Then, 30% sodium bicarbonate aqueous solution (50 mL) was added and extracted with CH₂Cl₂ (50 mL×3). The combined organic layer was washed with saturated aqueous NaCl, dried over anhydrous Na₂SO₄ and concentrated. The reaction proceeded to next step without further purification. MS (ESI, m/e): 301 [M+1]⁺.

Intermediate 4

(R)-1-phenylethyl (3R,4S)-4-allyl-3-azidopyrrolidine-3-carboxylate

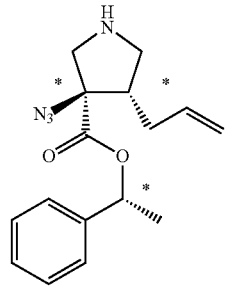 [SMILES: C=CC[C@H]1CNC[C@@]1(N=[N+]=[N-])C(=O)O[C@H](C)c1ccccc1]

Intermediate 4 was prepared from Intermediate 2 by the same procedure described for Intermediate 3. MS (ESI, m/e): 301 [M+1]⁺.

Intermediate 5

(rac)trans-1-(tert-butyl)3-ethyl-4-allyl-3-azidopyrrolidine-1,3-dicarboxylate

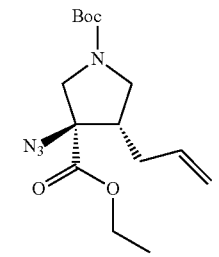 [SMILES: C=CC[C@H]1CN(C(=O)OC(C)(C)C)C[C@@]1(N=[N+]=[N-])C(=O)OCC]

To a stirred solution of (rac)-4-allyl-3-azido-1-(tert-butoxycarbonyl)pyrrolidine-3-carboxylic acid (0.56 g) from literature procedure in DMF (7 mL) was added K₂CO₃ (0.78 g). The above solution was added EtBr (0.31 g) in dropwise. The result mixture was stirred at r.t. for 2 hours. The reaction mixture was washed with water and extracted with MTBE. The organic layer was dried over anhydrous sodium sulfate, concentrated under vacuum and purified by silica gel flash chromatography (DCM:PE=0% to 100%) to give the title product as yellow oil, 0.61 g, yield 79%. MS (ESI, m/e): 325 [M+1]⁺.

Intermediate 6 ethyl (3R,4S)-4-allyl-3-azidopyrrolidine-3-carboxylate

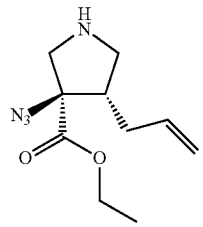 [SMILES: C=CC[C@H]1CNC[C@@]1(N=[N+]=[N-])C(=O)OCC]

Intermediate 6 was prepared from Intermediate 5 by the same procedure described for Intermediate 3. MS (ESI, m/e): 225 [M+1]$^+$.

Intermediate 7 tert-butyl (trans-2-aminocyclopropyl)carbamate

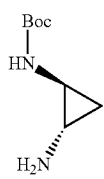

Step 1 diethyl (trans)-cyclopropane-1,2-dicarboxylate

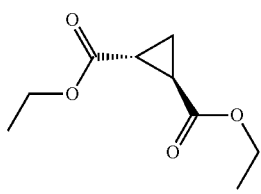

Ethyl 2-chloroacetate (200 g, 1.6 mol) was added to a stirred solution of ethyl acrylate (204 g, 2.04 mol) in DMF (550 ml) at 0° C. Sodium hydride (65.4 g, 2.725 mol) was added portion-wise to the reaction mixture at 0° C. over a period of 2 h. The reaction mixture was allowed to warm to room temperature and stirred for 16 h. The reaction mixture was quenched with ice (700 g) and extracted with EA. The organic layer was washed with water (500 ml), brine (500 ml) and dried over Na$_2$SO$_4$. The solution was filtered, concentrated and purified by silica gel column chromatography (EA:PE=10 to 30%) to give 170 g of title product.

Step 2 (trans)-cyclopropane-1,2-dicarboxylic Acid

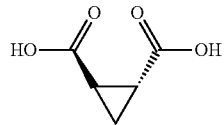

NaOH (73 g, 1.82 mol) in water (850 ml) was add dropwise to a stirred solution of the product in step 1 (170 g, 0.91 mol) in ethanol at 0° C. The reaction mixture was allowed to warm to room temperature. After 16 h, the reaction mixture was concentrated under reduced pressure. The residue was quenched with water and extracted with EA. The aqueous layer was adjusted to pH=2 using 1N HCl. The aqueous layer was extracted with EA. The organic layer was washed with water, brine and dried over Na$_2$SO$_4$. The solution was filtered, concentrated under reduced pressure to afford 88.4 g of title product.

Step 3 (trans)-cyclopropane-1,2-dicarbonyl Dichloride

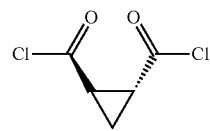

To a stirred solution of the product of step 2 (88 g, 677 mmol) in DCM (880 ml) was added oxalyl chloride (214 g, 1.69 mol) at 0° C. DMF (2.64 ml) was added drop wise at 0° C. The resulting mixture was stirred at room temperature for 2 h. The mixture was concentrated to dryness under vacuum. The material was used without further purification.

Step 4 (trans)-cyclopropane-1,2-dicarbonyl Diazide

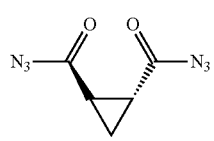

To a stirred solution of the product of step 3 (112 g, 677 mmol) in DCM (220 ml), sodium azide (154 g, 2.37 mmol) in water (440 ml) was added drop wise at −5° C. and stirred for 1 h. Then the mixture was warmed to room temperature and stirred for 2 h. The mixture was extracted with DCM. The organic layer was washed with water, brine and dried over Na$_2$SO$_4$. The solution was filtered, concentrated to half-volume. The residue was diluted with toluene (500 mL), and then partially concentrated under reduced pressure to remove DCM. The crude solution of the title compound was used in the next step without further purification.

Step 5 di-tert-butyl ((trans)-cyclopropane-1,2-diyl)dicarbamate

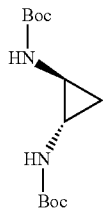

Crude product solution of step 4 in toluene was heat to 70° C. and stirred for 1 h. t-BuOH (100 g, 1.35 mol) was added drop wise at 70° C.~80° C. and stirred for 2 h. The reaction mixture was cooled to r.t. and concentrated to dryness under vacuum. The residue was diluted with ice water and extracted with EA. The organic layer was washed with water, brine and dried over $Na_2SO_4$. The solution was filtered, concentrated and purified by silica gel column chromatography (EA:PE=0-20%) to give 13.45 g of the title product.

Step 6 (trans)-cyclopropane-1,2-diamine.2HCl Salt

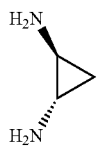

The product of step 5 (13.45 g, 49.45 mmol) in 4N HCl/EA (130 ml) was stirred at RT for 2 h. The solution was filtered and collected solids were washed with EA and dried to give 3.1 g of title product.

Step 7 tert-butyl ((trans)-2-aminocyclopropyl)carbamate

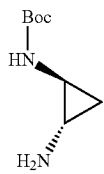

A solution of the product of step 6 (3.1 g, 21.53 mmol) in EtOH/$H_2O$ (164 ml/41 ml) was added $NaHCO_3$ (1.8 g, 21.53 mmol) and $(Boc)_2O$ (4.69 g, 21.53 mmol). After stirring for 16 h at r.t., the reaction mixture was diluted with water. The mixture was adjusted to pH=2 using 1N HCl and extracted with EA. The aqueous layer was adjusted to pH=8 using $Na_2CO_3$ and extracted with 10% iPrOH/DCM (2×150 ml). The organic layer was washed with water, brine and dried over $Na_2SO_4$. The solution was filtered, concentrated under reduced pressure to afford 2 g of pure product. MS (ES+): 367 [2M+23]$^+$. $^1$HNMR Spectrum: (400 MHz, DMSO-$d_6$) δ8.36 (bs, 3H), 7.14 (s, 1H), 2.87-2.86 (m, 1H), 2.50-2.49 (m, 1H), 1.39 (s, 9H) 1.09-1.02 (m, 1H), 0.92-0.86 (m, 1H).

Intermediate 8 tert-butyl((1-aminocyclopropyl)methyl)carbamate

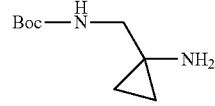 [SMILES: CC(C)(C)OC(=O)NCC1(N)CC1]

Step 1 1-((diphenylmethylene)amino)cyclopropane-1-carbonitrile

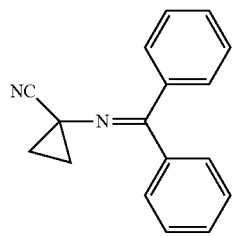 [SMILES: N#CC1(N=C(c2ccccc2)c2ccccc2)CC1]

To a stirred solution of 1-aminocyclopropane-1-carbonitrile HCl salt (16.17 g, 137 mmol) in DCM (330 ml), diphenylmethanimine (16.60 g, 91.21 mmol) was added. The resulting mixture was stirred at room temperature for 2 days. After the reaction was complete, the mixture was filtered to remove the precipitated ammonium chloride. The filtrate was evaporated to dryness in vacuo and purified by column chromatography (EA:PE=0-5%) to give 18 g of pure product. MS (ES+): 247 [M+1]$^+$.

Step 2 (1-((diphenylmethylene)amino)cyclopropyl) methanamine

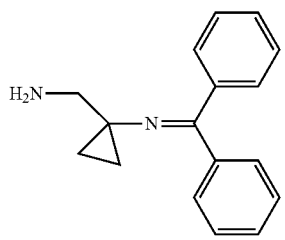 [SMILES: NCC1(N=C(c2ccccc2)c2ccccc2)CC1]

To a stirred solution of NaOH (5.8 g, 73.17 mmol) in EtOH (240 ml) were added the product of step 1 (18 g, 73.17 mmol) and Raney Nickel (4 g). The reaction mixture was stirred under $H_2$ overnight. After the reaction was complete, the solution was filtered through a layer of celite. The filtrate was concentrated to dryness under vacuum and purified by silica gel column chromatography (MeOH:EA: $NH_3H_2O$=9.7:0.3:0.15) to give 4.8 g of 1-(((diphenylmethylene)amino)methyl)cyclopropan-1-amine {MS (ES+): 251 [M+1]$^+$}, followed by 6 g of the title product {MS (ES+): 251 [M+1]$^+$}.

Step 3 tert-butyl ((1-((diphenylmethylene)amino) cyclopropyl)methyl)carbamate

Step 1 tert-butyl (1-(((diphenylmethylene)amino) methyl)cyclopropyl)carbamate

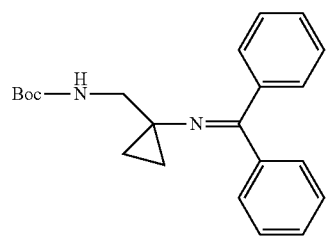 [SMILES: CC(C)(C)OC(=O)NCC1(N=C(c2ccccc2)c2ccccc2)CC1]

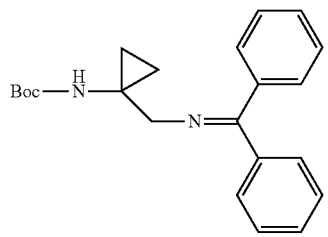

To a stirred solution of the product of step 2 (6 g, 23.81 mmol) in DCM (60 ml) were added triethylamine (2.88 g, 28.51 mmol) and (Boc)$_2$O (6.2 g, 28.44 mmol) at RT. The mixture was stirred for 1 h. The reaction mixture was quenched with water and extracted with EA. The organic layer was washed with brine and dried over Na$_2$SO$_4$. The solution was filtered, concentrated and purified by silica gel column chromatography (EA:PE=0 to 10%) to give 7 g of the title product. MS (ES+): 251 [M−100+1]$^+$.

To a stirred solution of 1-(((diphenylmethylene)amino) methyl)cyclopropan-1-amine (by-product in step 2 of Intermediate 8, 4.8 g, 23.81 mmol) in DCM (48 ml) were added triethylamine (2.3 g, 22.85 mmol) and (Boc)$_2$O (5 g, 22.85 mmol) at RT. The mixture was stirred for 1 h. The reaction mixture was quenched with water and extracted with EA. The organic layer was washed with brine and dried over Na$_2$SO$_4$. The solution was filtered, concentrated and purified by column chromatography (EA:PE=0-10%) to give 3.7 g of title product. MS (ES+): 251 [M−100+1]$^+$.

Step 4 tert-butyl ((1-aminocyclopropyl)methyl)carbamate

Step 2 tert-butyl (1-(aminomethyl)cyclopropyl)carbamate

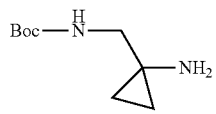 [SMILES: CC(C)(C)OC(=O)NCC1(N)CC1]

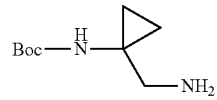

The product of Step 3 (7 g, 20 mmol) was dissolved in MeOH (150 ml). Pd(OH)$_2$/C (3.5 g) was added to the mixture and stirred under H$_2$ overnight. The solution was filtered through a layer of celite. The filtrate was concentrated to dryness under vacuum to give 3.1 g of crude product and purified by silica gel column chromatography (MeOH:DCM=0-10%) to give 2.25 g of the title product. MS (ES+): 187 [M+1]$^+$.

The product of step 1 (3.7 g, 10.57 mmol) was dissolved in MeOH (70 ml). Pd(OH)$_2$/C (1.8 g) was added to the mixture and stirred under H$_2$ overnight. The solution was filtered through a layer of celite. The filtrate was concentrated to dryness under vacuum to give 3.6 g of crude product and purified by column chromatography (MeOH: DCM=0-10%) to give 1.8 g of title product. MS (ES+): 187 [M+1]$^+$.

Intermediate 9 tert-butyl (1-(aminomethyl)cyclopropyl)carbamate

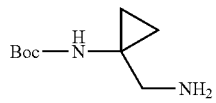

Intermediate 10 tert-butyl (1-amino-2-methylpropan-2-yl)carbamate

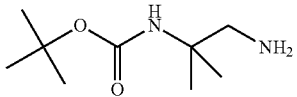

Step 1 tert-butyl (1-amino-2-methyl-1-oxopropan-2-yl)carbamate

The invention claimed is:
1. A compound represented by Formula (I), or a pharmaceutically acceptable salt, stereoisomer or tautomer thereof:

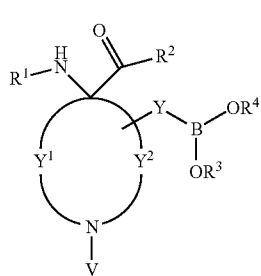

Formula (I)

or a pharmaceutically acceptable salt, stereoisomer, tautomer, or prodrug thereof,
wherein
$R^1$ is selected from H, straight or branched $(C_{1-6})$alkyl, $(C_{3-6})$cycloalkyl, $(C_{3-10})$ cycloalkyl-$(C_{1-6})$alkylene-, $(C_{5-10})$aryl-$(C_{1-12})$alkylene-, $(C_{1-10})$heteroaryl-$(C_{1-12})$alkylene-, $(C_{3-10})$heterocycloalkyl-$(C_{1-12})$alkylene- and $(C_{1-6})$alkyl-C(O)-;
$R^2$ is selected from $OR^a$, and $NR^bR^c$;
$R^a$, $R^b$, $R^c$ is selected from hydrogen, straight or branched $(C_{1-12})$ alkyl, $(C_{3-12})$ cycloalkyl, $(C_{3-10})$ cycloalkyl-$(C_{1-12})$alkylene-, $(C_{5-10})$aryl-$(C_{1-12})$alkylene-, $(C_{1-})$heteroaryl-$(C_{1-12})$alkylene-, $(C_{3-10})$ heterocycloalkyl-$(C_{1-12})$alkylene-, $R^a$, $R^b$, $R^c$ is optionally substituted with $R^5$;
$R^3$ and $R^4$ are independently selected from hydrogen, straight or branched $(C_{1-6})$alkyl, $(C_{3-8})$cycloalkyl, $(C_{3-8})$cycloalkyl$(C_{1-6})$alkylene, substituted $(C_{3-8})$cycloalkyl$(C_{1-6})$alkylene, $(C_{5-12})$aryl; $R^3$ and $R^4$ can be connected with one or two bonds, when it is connected by two bonds, it form another ring other than the ring containing B and O;
Y, $Y^1$ and $Y^2$ forming a ring structure having 1 to 10 carbon atoms, wherein each of Y, $Y^1$ and $Y^2$ is independently selected from substituted or unsubstituted alkylene, alkenylene, alkynylene, arylene, and cycloalkylene, wherein one or more —$CH_2$— groups in Y are optionally and independently replaced with a moiety Q that is selected from O, $NR^i$, S, S(O), $S(O)_2$, and $CR^5R^6$; or wherein any two adjacent —$CH_2$— groups optionally are replaced by a cycloalkylene group, provided that Y does not contain two adjacent Q moieties selected from O, $NR^i$, S, S(O), and $S(O)_2$;
$R^5$ and $R^6$ are independently chosen from halogen, $C_{1-12}$ alkyl, $C_{2-12}$ alkenyl, $C_{2-12}$ alkynyl, $C_{3-12}$ cycloalkyl, $C_{6-12}$ aryl, $C_{3-12}$ heterocyclyl, $C_{1-12}$ heteroaryl, —$S(O)_mR^7$, —$S(O)_2NR^jR^k$, —$S(O)_2OR^7$, —$NO_2$, —$NR^jR^k$, —$(CR^8R^9)_nOR^7$, —CN, —C(O)$R^7$, —OC(O)$R^7$, —$O(CR^8R^9)_nR^7$, —$NR^7C(O)R^{10}$, —$(CR^8R^9)_nC(O)OR^7$, —$(CR^8R^9)_nC(O)NR^jR^k$, —$(CR^8R^9)_nNR^jR^k$, —$C(=NR^j)NR^jR^k$, —$NR^7C(O)NR^jR^k$, —$NR^7S(O)_2R^{10}$ or $SF_5$, $R^i$, $R^j$ and $R^k$ are defined as the same as for $R^b$ and $R^c$ and each hydrogen in $R^5$ and $R^6$ may be unsubstituted or substituted by $R^{10}$, and wherein $R^5$ and $R^6$ on adjacent atoms are uncombined or combine to form a $C_{6-12}$ aryl, 5-12 membered heteroaryl, $C_{3-12}$ cycloalkyl or 3-12 membered heteroalicyclyl;
m is 0, 1 or 2;
n selected from 0 to 10;
$R^7$, $R^8$ and $R^9$ are independently chosen from hydrogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclyl, 5-12 membered heteroaryl; $R^8$ and $R^9$ together with the carbon atom to which they are bound form a 3-, 4-, 5- or 6-membered ring that is fully saturated, or partially saturated and that optionally contains 1-3 additional heteroatom ring members selected from O, S, and NR, wherein the ring is optionally fused with a cycloalkyl, heterocyclic or aromatic ring; $R^7$, $R^8$ and $R^9$ are optionally substituted with $R^{10}$;
$R^{10}$ may be chosen from halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heterocyclic ring, 5-12 membered heteroaryl ring, —$NH_2$, —CN, —OH, —O—$C_{1-12}$alkyl, —O—$(CH_2)_nC_{3-12}$ cycloalkyl, —O—$(CH_2)_nC_{6-12}$ aryl, —O—$(CH_2)_n$(3-12 membered heterocyclyl) or —O—$(CH_2)_n$(5-12 membered heteroaryl); and each hydrogen in $R^{10}$ may be unsubstituted or substituted by $R^{11}$;
$R^{11}$ may be chosen from halogen, $C_{1-12}$ alkyl, $C_{1-12}$ alkoxy, $C_{3-12}$ cycloalkyl, $C_{6-12}$ aryl, 3-12 membered heterocyclyl, 5-12 membered heteroaryl, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heterocyclyl), —O—$(CH_2)_n$(5-12 membered heteroaryl) or —CN, and each hydrogen in $R^{11}$ may be unsubstituted or substituted by halogen, —OH, —CN, —$C_{1-12}$ alkyl which may be unsubstituted, or partially halogenated or fully halogenated, —O—$C_{1-12}$ alkyl which may be unsubstituted or partially halogenated or fully halogenated, or substituted with —C(O) $R^a$;
V is selected from —$S(O)_2NR^jR^k$, —$S(O)_2OR^7$ or

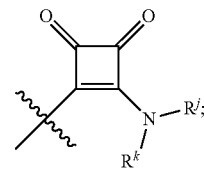

$R^7$, $R^i$, $R^j$ and $R^k$ are defined as the same as for $R^b$ and $R^c$ and each hydrogen in $R^7$ may be unsubstituted or substituted by $R^{10}$.

2. The compound according to claim 1, the compound represented by Formula (II),

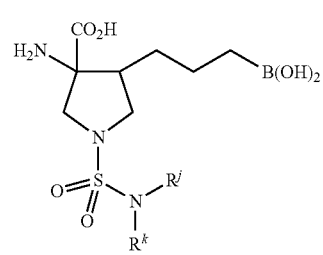

(II)

$R^j$ and $R^k$ are defined as above.

3. The compound according to claim 1, the compound represented by Formula (III),

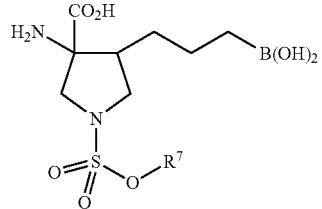

(III)

R[7] is defined as above.

4. The compound according to claim 1, the compound represented by Formula (IV),

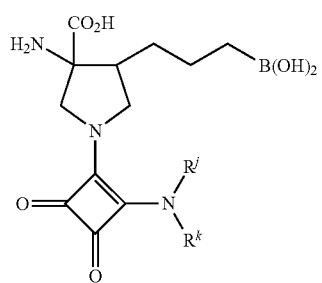

(IV)

R[j] and R[k] are defined as above.

5. A pharmaceutical composition comprising: the compound represented by Formula (I) to Formula (XII):

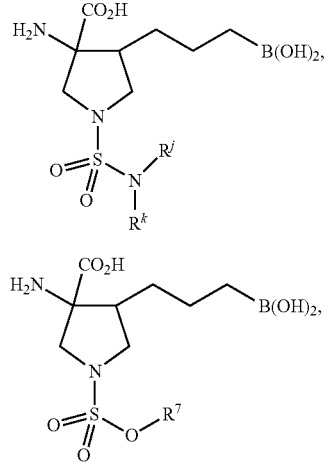

Formula (II)

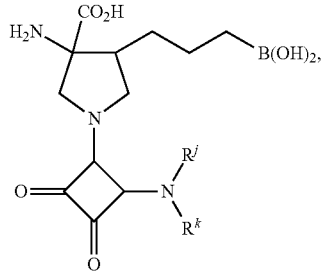

Formula (III)

Formula (IV)

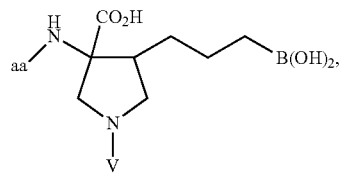

Formula (V)

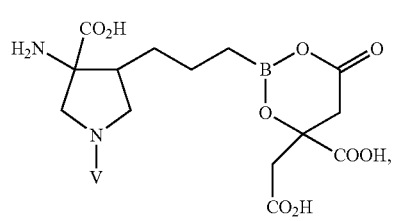

Formula (VI)

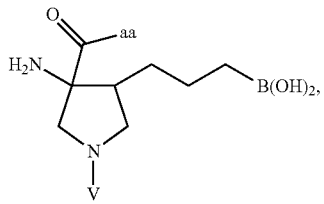

Formula (VII)

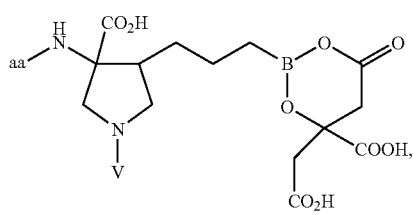

Formula (VIII)

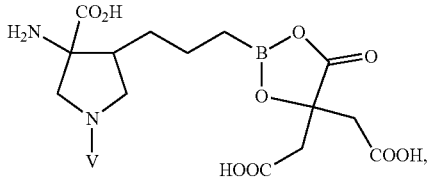

Formula (IX)

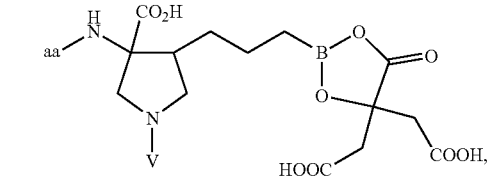

Formula (X)

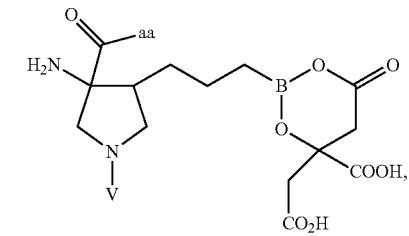

Formula (XI)

Formula (XII)

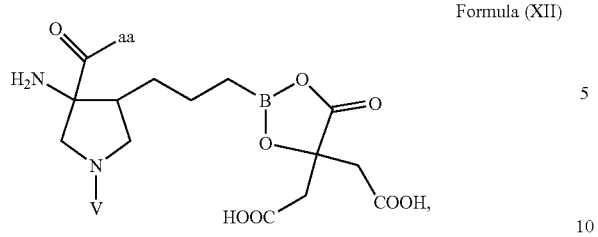

or a pharmaceutically acceptable salt, stereoisomer or tautomer thereof according to claim 1; and a pharmaceutically acceptable carrier, an antineoplastic agent, cancer vaccines, adoptive cell transfer immunotherapy, and radiation therapy, or a combination thereof.

6. The pharmaceutical composition of claim 5 wherein the neoplastic agent is one or more of IDO inhibitors, TDO inhibitors, IDO/TDO dual inhibitors, EP4 antagonists, angiogenesis inhibitors, cell proliferation and survival signal inhibitors, apoptosis inducers and agents, STING agonists, CTLA4 antibody, PD-1 antibody, PD-L1 antibody, LAG-3 antibody, and TIM-3.

* * * * *